(12) United States Patent
Kauffman et al.

(10) Patent No.: US 8,849,580 B2
(45) Date of Patent: Sep. 30, 2014

(54) USES OF SYSTEMS WITH DEGREES OF FREEDOM POISED BETWEEN FULLY QUANTUM AND FULLY CLASSICAL STATES

(75) Inventors: Stuart Kauffman, Santa Fe, NM (US); Samuli Niiranen, Tampere (FI); Gábor Vattay, Budapest (HU)

(73) Assignees: The University of Vermont, Burlington, VT (US); Tampere University of Technology, Tampere (FI)

( * ) Notice: Subject to any disclaimer, the term of this patent is extended or adjusted under 35 U.S.C. 154(b) by 0 days.

(21) Appl. No.: 13/187,257

(22) Filed: Jul. 20, 2011

(65) Prior Publication Data
US 2012/0071333 A1  Mar. 22, 2012

Related U.S. Application Data

(60) Provisional application No. 61/367,781, filed on Jul. 26, 2010, provisional application No. 61/367,779, filed on Jul. 26, 2010, provisional application No. 61/416,723, filed on Nov. 23, 2010, provisional application No. 61/420,720, filed on Dec. 7, 2010, provisional application No. 61/431,420, filed on Jan. 10, 2011.

(51) Int. Cl.
| | | |
|---|---|---|
| *G01N 33/48* | (2006.01) | |
| *G06F 19/00* | (2011.01) | |
| *G06N 99/00* | (2010.01) | |
| *C40B 30/02* | (2006.01) | |
| *B82Y 10/00* | (2011.01) | |

(52) U.S. Cl.
CPC ............ *G06N 99/002* (2013.01); *G06F 19/706* (2013.01); *C40B 30/02* (2013.01); *B82Y 10/00* (2013.01)
USPC .......................................................... 702/19

(58) Field of Classification Search
CPC ...... G06F 9/4843; G06F 19/06; G06N 99/002
See application file for complete search history.

(56) References Cited

U.S. PATENT DOCUMENTS

| 6,605,822 B1 * | 8/2003 | Blais et al. ...................... 257/34 |
| 7,904,283 B2 | 3/2011 | Merz, Jr. et al. |

OTHER PUBLICATIONS

Ashkenasy et al., Boolean Logic Functions of a Synthetic Peptide Network, JACS Aug. 19, 2004, 126(36): 11140-11141.
Ashkenasy et al., Design of a directed molecular network, PNAS, Jul. 27, 2004, 101(30): 10872-10877.
Bachmann et al., Autocatalytic self-replicating micelles as models for prebiotic structures, Nature, May 7, 1992, 357: 57-59.
Bachmann et al., Self-Replicating Reverse Micelles and Chemical Autopoiesis, J Am Chem Soc. 1990, 112: 8200-8201.
Bieberich, Erhard, Non-local Quantum evolution of entangled ensemble states in neural nets and its significance for brain function and a theory of consciousness; revised Version Jul. 26, 1999; retrieved Oct. 11, 2013 from http://arxiv.org/html/quant-ph/9906011v2; 15 pages.
Bliokh et al., Tunable electronic transport and unidirectional quantum wires in graphene subjected to electric and magnetic fields; Phys Review 2010; B81: 075410-1-075410-9.
Caivano et al., Feshbach resonance and mesoscopic phase separation near a quantum critical point in multiband FeAs-based superconductors, Supercond Sci Technol., 2008, preprint from arXiv0809.4865; 31 pages.
Cao et al., Optimization of Exciton Trapping in Energy Transfer Processes, J Phys Chem A, Dec. 17, 2009, 113(50): 13825-13838.
Cartlidge, Edwin, Physicists create a living laser; physicsworld.com Jun. 12, 2011, retrieved Oct. 11, 2013 from http://physicsworld.com/cws/article/news/2011/jun/12/physicists-create-a-living-laser; 2 pages.
Chan, Sunney I., Exciton Interation. Hypo- and Hyper-chromism; Biophyscial Chemistry 24a, Winter Term 2009/10, Feb. 1, 2010; PowerPointPresentation, 10 pages.
Collini et al., Coherent Intrachain Energy Migration in a Conjugated Polymer at Room Temperature, Science 2009, 323: 369-373.
Collini et al., Coherently wired light-harvesting in photosynthetic marine algae at ambient temperature, Nature Feb. 4, 2010, 463: 644-647.
Cormick et al., Observing different phases for the dynamics of entanglement in an ion trap, Phys Rev A, 2010, 81: 022306-1 to 022306-5.
Day, Charles, Month-long calculation resolves 82-year-old quantum paradox; Search & Discovery, Physics Today Sep. 2009, pp. 16-17.
de la Lande et al., Transmission Coefficients for Chemical Reactions with Multiple States: Role of Quantom Decoherence; JACS 2011, 133: 3883-3894.
de Oliveira et al., Probing of the quantum dot size distribution in CdTedoped glasses by photoluminexcence excitation spectroscopy, Appl Phys Lett. 1995, 66: 439.
Dotta et al., Photon emissions from human brain and cell culture exposed to distally rotating magnetic fields shared by separate light-stimulated brains and cells; Brain Research, 2011, 1388: 77-88.

(Continued)

*Primary Examiner* — Eric S Dejong

(74) *Attorney, Agent, or Firm* — Knobbe, Martens, Olson & Bear LLP

(57) ABSTRACT

Disclosed herein are systems and uses of systems operating between fully quantum coherent and fully classical states. Such systems operate in what is termed the "Poised realm" and exhibit unique behaviors that can be applied to a number of useful applications. Non-limiting examples include drug discovery, computers, and artificial intelligence.

10 Claims, 10 Drawing Sheets

(56) References Cited

OTHER PUBLICATIONS

Driel et al., Frequency-Dependent Spontaneous Emission Rate from CdSe and CdTe nanocrystals: Influence of Dark States; Phys Review Ltts; 2005, 95: 236804-1 to 236804-4.
Fischer et al., Observation of the Quantum Zeno and Anti-Zeno Effects in an Unstable System, Phys Rev Lett. Jul. 23, 2001, 85(4): 040402-1 to 040402-4.
Franson et al., Generation of entangled ancilla states for use in linear optics quantum computing, Phys Rev A, 2004, 69: 052328-1 to 052328-7.
Fratini et al., Scale-free structural organization of oxygen interstitials in La2CuO4+y, Nature, Aug. 12, 2010, 466: 841-844.
Galve et al., Bringing Entanglement to the High Temperature Limit, Phys Rev Lett Oct. 29, 2010, 105: 180501-1 to 180501-4.
Gauger et al., Sustained Quantum Coherence and Entanglement in the Avian Compass, Phys Rev Lett. Jan. 28, 2011, 106: 040503-1 to 040503.
Ihexis LLC, Programmable Matter Super-Turing Hypercomputers; Dec. 1, 2008, 13 pages.
Itano et al., Quantum Zeno effect, Phys Review A, Mar. 1, 1990, 41(5): 2295-2300.
Kauffman, Stuart, Agents, or How Doing Leads to Values, Blog posted May 10, 2010; retrieved Oct. 10, 2013 from http://www.npr.org/blogs/13.7/2010/05/10/126714358/agency-doing-values-and-ought; 4 pages.
Kauffman, Stuart, Beyond Einstein and Schrodinger? The Quantum Mechanics of Closed Quantum Systems; Blog posted Nov. 22, 2010; retrieved Oct. 10, 2013 from http://www.nprorg/blogs/13.7/2010/11/22/131510041/beyond-einstein-and-schrodinger-the-quantum-mechanics-of-closed-quantum-systems; 4 pages.
Kauffman, Stuart, Can a Changing Adjacent Possible Acausally Change History? The Open Universe IV, Bog posted Feb. 25, 2010; retrieved Oct. 10, 2013 from http://www.npr.org/blogs/13.7/2010/02/can_a_changing_adjacent_possib.html; 9 pages.
Kauffman, Stuart, Can We Have a Responsible Free Will? Blog posted Jan. 31, 2011; retrieved Oct. 10, 2013 from http://www.npr.org/blogs/13.7/2011/01/31/133319117/can-we-have-a-responsible-free-will; 3 pages.
Kauffman, Stuart, Complexity Theory: Normal Science and Frontiers Classical and Quantum, Private Paper Nov. 6, 2010; 49 pages.
Kauffman, Stuart, Contemporary Work on the Origin of Life, Blog posted May 17, 2010; retrieved Oct. 10, 2013 from http://www.npr.org/blogs/13.7/2010/05/05/126532686/contemporary-work-on-the-origin-of-life; 6 pages.
Kauffman, Stuart, Free Will: There Are No Easy Answers; Blog posted Aug. 23, 2010; retrieved Oct. 10, 2013 from http://www.npr.org/blogs/13.7/2011/02/18/129375622/free-will; 6 pages.
Kauffman, Stuart, How Can Mind Act on Matter? Blog posted Mar. 22, 2010; retrieved Oct. 10, 2013 from http://www.nprorg/blogs/13.7/2010/03/how_can_mind_act_on_matter.html; 9 pages.
Kauffman, Stuart, How Mind Can Act Acausally on Brain? Blog posted Dec. 27, 2010; retrieved Oct. 10, 2013 from http://www.npr.org/blogs/13.7/2010/12/27/132361145/how-mind-can-act-acausally-on-brain; 4 pages.
Kauffman, Stuart, Is the Human Mind Algorithmic? Blog posted Mar. 15, 2010; retrieved Oct. 10, 2013 from http://www.npr.org/blogs/13.7/2010/03/is_the_human_mind_algorithmic_1.html; 6 pages.
Kauffman, Stuart, Is There a 'Poised Realm' Between the Quantum and Classical Worlds? Blog posted Mar. 3, 2010; retrieved Oct. 10, 2013 from http://www.npr.org/blogs/13.7/2010/03/is_there_a_poised_realm_betwee.html; 7 pages.
Kauffman, Stuart, Res Extensa, Res Potentia and the Poised Realm; Blog posted Aug. 17, 2010; retrieved Oct. 10, 2013 from http://www.npr.org/blogs/13.7/2010/08/17/129250892/res-extensa-res-potentia-and-the-poised-realm; 7 pages.
Kauffman, Stuart, Standing the Brain on Its Head; Blog posted Jan. 30, 2011; retrieved Oct. 10, 2013 from http://www.npr.org/blogs/13.7/2011/01/30/133319070/standing-the-brain-on-its-head; 5 pages.
Kauffman, Stuart, The Hard Problem: Consciousness; Blog posted Mar. 30, 2010; retrieved Oct. 10, 2013 from http://www.npr.org/blogs/13.7/2010/03/the_hard_problem_conscousness.html; 8 pages.
Kauffman, Stuart, The Non-Algorithmic Trans-Turing System; Blog posted Dec. 14, 2010; retrieved Oct. 10, 2013 from http://www.npr.org/blogs/13.7/2010/12/14/132039092/the-non-algorithmic-trans-turing-system; 4 pages.
Kauffman, Stuart, The 'Poised Realm' Is Real; Blog posted Dec. 6, 2010; retrieved Oct. 10, 2013 from http://www.npr.org/blogs/13.7/2010/12/06/131846605/the-poised-ream-is-real; 4 pages.
Kauffman, Stuart, The Quantum Mechanics of Open Quantum Systems; Blog posted Nov. 29, 2010; retrieved Oct. 10, 2013 from http://www.npr.org/blogs/13.7/2010/11/24/131567335/the-quantum-mechanics-of-open-quantum-systems; 4 pages.
Kauffman, Stuart, To Be Is to Be Perceived: A Clue to the Observer Quantum Measurement Problem; Blog posted Apr. 7, 2010; retrieved Oct. 10, 2013 from http://www.npr.org/blogs/13.7/2010/04/to_be_is_to_be_perceived_the_q.html; 6 pages.
Kauffman, Stuart, Toward a Responsible Free Will; Blog posted Mar. 26, 2010; retrieved Oct. 10, 2013 from http://www.npr.org/blogs/13.7/2010/03/towards_a_responsible_free_wil_1.html; 7 pages.
Kauffman, Stuart, We Seem to Be Zombies; Blog posted Dec. 20, 2010; retrieved Oct. 10, 2013 from http://www.npr.org/blogs/13.7/2010/12/20/132203880/we-seem-to-be-zombies; 5 pages.
Kauffman, Stuart, What Is Consciousness? A Hypothesis; Blog posted Jan. 19, 2011; retrieved Oct. 10, 2013 from http://www.npr.org/blogs/13.7/2011/01/29/133318986/what-is-consciousness-a-hypothesis; 4 pages.
Kaulakys et al., Quantum anti-Zeno effect, Phys Rev A, Aug. 1997, 56(2): 1131-1137.
Kocherzhenko et al., Charge Transfer Through Molecules with Multiple Pathways: Quantum Interference and Dephasing, J Phys Chem C. 2010, 114(17): 7973-7979.
Kotter et al., Solar Nantenna Electromagnetic Collectors; 2nd International Conference on Energy Sustainability Aug. 2008; Idaho National Laboratory ES 2008-54016; 8 pages.
Kottos et al., Periodic Orbit Theory and Spectral Statistics for Quantum Graphs, Annals Phys. 1999, 274: 76-124.
Kurzweil Accelerating Intelligence, Researchers use high magnetic fields to suppress decoherence, paving the way for quantum computing; Jul. 21, 2011, retrieved Oct. 11, 2013 from http://physicsworld.com/cws/article/news/2011/jun/12/physicists-create-a-living-laser; 1 page.
Lincoln et al., Self-Sustained Replication of an RNA Enzyme, Science, Feb. 27, 2009, 323: 1229-1232.
Luisi et al., A Possible Route to Prebiotic Vesicle Reproduction, MIT; Artificial Life 2004, 10: 297-308.
Luisi et al., Self-Replicating Micelles—A Chemical Version of a Minimal Autopoietic System, Origins of Life and Evolution of the Biosphere, 1989, 19: 633-643.
Lukk et al., A global map of human gene expression, Correspondence to Editor; Nature Biotech. Apr. 2010, 28(4): 322-324.
Nayakar et al., Quantum randomness and free will, Poornaprajna Institute of Scientific Research, Sadashivnagar, Bangalore; Nov. 22, 2010, 11 pages.
Nazarkin et al., Electromagnetically Induced Quantum Memory, Phys Rev Lett. Jan. 30, 2004, 92(4): 043002-1 to 043002-4.
Palla et al., Spectral transitions in networks, New J Phys. Dec. 6, 2006, 8: 307-317.
Pattanayak et al., Exponentially Rapid Decoherence of Quantum Chaotic Systems, Phys Rev Lett. Nov. 24, 1997, 79(21): 4131-4134.
Pattanayak, Arjendu K., Lyapunov Exponents, Entropy Producation, and Decoherence, Phys Rev Lett. Nov. 29, 1999, 83(22): 4526-4529.
Paz et al., Dynamics of the Entanglement between Two Oscialltors in the Same Environment, Phys Rev Lett. Jun. 6, 2008, 100: 220401-1 to 220401-4.
Paz et al., Entanglement dynamics during decoherence, Quantum Inf Process-Springer Science + Business Media, 2009, 8: 535-548.
Paz et al., Redundancy of classical and quantum correlations during decoherence, Phys Rev A, 2009, 80: 042111-1 to 042111-6.

(56) References Cited

OTHER PUBLICATIONS

PCE Stamp, Decoherence: Fact & Fiction, presented at Orcas Island on Jul. 19, 2010 by faculty of UBC Vancouver, Physics & Astronomy Department et al., PowerPoint Presentation, 46 pages.
Pessa, Eliano, Phase Transitions in Biological Matter, Università di Pavia, Udine, Italy, Research Paper Sep. 2007, 64 pages.
Prezhdo, Oleg V., Quantum Anti-Zeno Acceleration of a Chemical Reaction, Phys Rev Lett. Nov. 20, 2000, 85(21): 4413-4417.
Reich, Eugenie Samuel, Quantum theorem shakes foundations—The wavefunction is a real physical object after all, say researchers; Nature/News Nov. 17, 2011; retrieved Oct. 11, 2013 from http://www.nature.com/news/quantum-theorem-shakes-foundations-1.9392; 3 pages.
Rigaud et al., Reconstitution of membrane proteins into liposomes: application to energy transducing membrane proteins; Biochim Biophys Acta, 1995, 1231: 223-246.
Ruyant, Quentin, Quantum Physics and the Ontology of Mind—Focus Issue, J Conscious Expl Res. Nov. 2010, 1(8): 1027-1047.
Sanders, Laura, Everyday entanglement: Physicists take quantum weirdness out of the lab; Science News, Nov. 20, 2010, 178(11): 22-29.
Sanderson, Katharine, A demon of a device—Light makes molecular machines perform trick; Nature/News Jan. 31, 2007; retrieved Oct. 11, 2013 from http://www.nature.com/news/2007/070129/full/news070129-10.html; 2 pages.
Sargent, Edward H., Infrared Optoelectronics You Can Apply With a Brush; IEEE Spectrum Feb. 2010; 5 pages.
Sargent, Edward H., Infrared photovoltaics made by solution processing, Nature Photonics May 28, 2009; 3: 325-331.
Scholes, Gregory D., Quantum-Coherent Electronic Energy Transfer: Did Nature Think of It First? J Phys Chem Lett. Jan. 7, 2010, 1: 2-8.
Scholes, Gregory D., Quantum-Mechanical Optimization of Light-Harvesting in Photosynthesis, Lecture Outline, Fall 2010 University of Vermont, Theoretical and Applied Physics; 1 page [Abstract Only].
Susumu et al., Conjugated Chromophore Arrays with Unusually Large Hole Polaron Delocalization Lengths; JACS Jun. 9, 2006, 128: 8380-8381.
Tiwari et al., Electronic resonance with anticorrelated pigment vibrations drives photosynthetic energy transfer outside the adiabatic framework, PNAS Jan. 22, 2013, 110(4): 1203-1208.
Vattay et al., Quantum biology on the edge of quantum chaos; Feb. 29, 2012; arXiv:1202.6433v1; 5 pages.
Viola et al., Dynamical suppression of decoherence in two-state quantum systems, Phys Review Oct. 1998, 58(4): 2733-2744.
Wagner et al., Systems Chemistry: Logic Gates, Arithmetic Units, and Network Motifs in Small Networks, Chem Eur J. 2009 (online: Dec. 23, 2008), 15: 1765-1775.
Wang et al., Vibrationally coherent photochemistry in the femtosecond primary event of vision, Science, New Series, Oct. 21, 1994, 266(5184): 422-424.
Weinstein et al., The Edge of Quantum Chaos, MIT Paper #206039, Version 2, Oct. 3, 2002, 4 pages.
Weizmann Institute of Science, Biological molecules select their spin; Phys.org Mar. 31, 2011, retrieved Oct. 11, 2013 from http://phys.org/news/2011-03-biological-molecules.html; 1 page.
Wilkinson et al., Experimental evidence for non-exponential decay in quantum tunnelling, Nature Jun. 5, 1997, 387: 575-549.
Wolynes, Peter G., Some quantum weirdness in physiology, Commentary, PNAS Oct. 13, 2009, 106(41): 17247-17248.
Womick et al., Toward the origin of exciton electronic structure in phycobiliproteins, J Chem Phys. Jul. 14, 2010, 133: 024507-1 to 024507-10.
Zhu et al., Closed loop learning control to suppress the effects of quantum decoherence, J Chem Phys. Apr. 15, 2003, 118(15): 6751-6757.
Zhu et al., Pure phase decoherence in a ring geometry; Phys Review Jun. 25, 2010; A81: 16 pages.
Zyga, Lisa, Quantum explanation for how we smell gets new support; Phys.org Mar. 28, 2011, retrieved Oct. 11, 2013 from http://phys.org/news/2011-03-quantum-explanation.html; 2 pages.
Zyga, Lisa, Quantum mechanics may explain how humans smell; Phys.org Feb. 1, 2007, retrieved Oct. 11, 2013 from http://phys.org/news89542035.html; 2 pages.

* cited by examiner

USES OF SYSTEMS WITH DEGREES OF FREEDOM POISED BETWEEN FULLY QUANTUM AND FULLY CLASSICAL STATES

CROSS-REFERENCE TO RELATED APPLICATIONS

This application claims the benefit of U.S. Provisional Application Nos. 61/367,781, filed Jul. 26, 2010; 61/367,779, filed Jul. 26, 2010; 61/416,723, filed Nov. 23, 2010; 61/420,720, filed Dec. 7, 2010; and 61/431,420, filed Jan. 10, 2011, all of which are incorporated herein by reference in their entirety.

BACKGROUND

1. Field of the Invention

The present invention relates to systems and uses of systems operating between fully quantum coherent and fully classical states. Non-limiting applications include drug discovery, computers, and artificial intelligence.

2. Background Description

Many physical systems having quantum degrees of freedom quickly decohere to classicity for all practical purposes. Thus, many designed systems consider only classical behaviors. One example is in the field of drug discovery where traditional approaches to drug design considers the lock-and-key fitting of a molecule into an enzyme or receptor. Other designed systems are carefully setup to maintain full quantum coherence, for example, the qubits in a quantum computer. However, recent discoveries have indicated several systems in nature that have relatively slow decoherence. Birds are able to see magnetic field lines due to a quantum coherent chemical reaction in their retina. Light harvesting molecules are able to maintain quantum coherent electron transport for times much longer than the expected coherence time at room temperatures. The existence of such cases demonstrates that quantum coherence can exist at room temperature and at the presence of water bath and evolution can 'design' quantum coherent structures to play certain biological roles. Thus, there is a need for new systems that utilize the unique properties that exist between full quantum coherence and classicity.

SUMMARY OF THE INVENTION

Disclosed herein are various methods of classifying the state of a system, such as a molecule interacting with its environment, in terms of its degree of order, its degree of coherence, and/or its rate of coherence decay. Some embodiments include classifying only a single one of these variables whereas other embodiments include classifying two or all three of the variables. These methods include classifying the system in the course of creating systems that exist and/or operate at a specific point or region of a classification space described the variables discussed above and all practical outcomes of such creation.

Disclosed herein is a quantum reservoir computer that includes a plurality of nodes, each node comprising at least one quantum degree of freedom that is coupled to at least one quantum degree of freedom in each other node; at least one input signal generator configured to produce at least one time-varying input signal that couples to the quantum degree of freedom; and a detector configured to receive a plurality of time-varying output signals that couple to the quantum degree of freedom.

Also disclosed herein is a method of drug discovery that includes selecting a biological target; screening a library of candidate molecules to identify a first subset of candidate molecules that bind to the biological target; determining the energy level spacing distribution of a quantum degree of freedom in each of the candidate molecules in the first subset; comparing the energy level spacing distribution to at least one pre-determined reference function; and selecting a second subset of molecules from the first subset as drug candidates based on the comparison.

Further disclosed herein is a method of drug discovery that includes selecting a biological target; screening a library of candidate molecules to identify a first subset of candidate molecules that bind to the biological target; determining the energy level spacing distribution of a quantum degree of freedom in each of the candidate molecules in the first subset; conducting an in vitro or in vivo assay for biological activity on each of the candidate molecules in the first subset; correlating the energy level spacing distribution with activity determined from the in vitro or in vivo assay; determining the energy level spacing distributions of a quantum degree of freedom in a new set of candidate molecules; comparing the energy level spacing distributions of the new set of candidate molecules with energy level spacing distributions that correlate with biological activity; and select as drug candidates from the new set of candidate molecules those molecules whose energy level spacing distributions exhibit a pre-determined level of similarity to the energy level spacing distributions that correlate with biological activity.

Further disclosed herein is a method of drug discovery that includes selecting a biological target; screening a library of candidate molecules to identify a first subset of candidate molecules that bind to the biological target; measuring decoherence decay of a quantum degree of freedom in each of the candidate molecules in the first subset; comparing the decoherence decay to at least one pre-determined reference function; and selecting a second subset of molecules from the first subset as drug candidates based on the comparison.

Further disclosed herein is a method of drug discovery that includes selecting a biological target; screening a library of candidate molecules to identify a first subset of candidate molecules that bind to the biological target; measuring decoherence decay of a quantum degree of freedom in each of the candidate molecules in the first subset; conducting an in vitro or in vivo assay for biological activity on each of the candidate molecules in the first subset; correlating the decoherence decay with activity determined from the in vitro or in vivo assay; measuring decoherence decay of a quantum degree of freedom in a new set of candidate molecules; comparing the decoherence decay of the new set of candidate molecules with the decoherence decay that correlate with biological activity; and select as drug candidates from the new set of candidate molecules those molecules whose decoherence decay exhibit a pre-determined level of similarity to the decoherence decay that correlate with biological activity.

Further disclosed herein is a Trans-Turing machine that includes a plurality of nodes, each node comprising at least one quantum degree of freedom that is coupled to at least one quantum degree of freedom in another node and at least one classical degree of freedom that is coupled to at least one classical degree of freedom in another node, wherein the nodes are configured such that the quantum degrees of freedom decohere to classicity and thereby alter the classical degrees of freedom, which then alter the decoherence rate of remaining quantum degrees of freedom; at least one input signal generator configured to produce an input signal that recoheres classical degrees of freedom to quantum degrees of freedom; and a detector configured to receive quantum or classical output signals from the nodes.

Further disclosed herein a method of measuring the state of a physical system that includes determining the degree of quantum coherence of at least one degree of freedom in the system; determining the degree of order of the system; and classifying the system based on the determined degree of quantum coherence and the determined degree of order.

In one embodiment, determining the degree of order comprises measuring decoherence decay of a quantum degree of freedom in the system. In one embodiment, determining the degree of order comprises determining the energy level spacing distribution of a quantum degree of freedom in the system. In one embodiment, the system is a molecule.

DETAILED DESCRIPTION OF THE PREFERRED EMBODIMENT

Described herein are several new systems and uses of systems operating in what is termed herein as the "Poised Realm." By "Poised Realm," it is meant a physical system that does not exhibit fully quantum behavior nor exhibits fully classical behavior. In this sense, the system is "poised", or even can "hover" between the quantum and classical worlds. By Poised Realm, we mean any physical means or procedure to achieve such a system poised between quantum and classical behavior, including as bounding limits, fully quantum coherent behavior and fully classical behavior.

In one characterization of the Poised Realm, we use two independent features of, without loss of generality, open quantum systems. The degree of decoherence and/or recoherence is one feature. In addition to their quantum, decohering, recohering, or classical behavior, physical systems may also be classified according to the degree of order or chaotic behavior that they exhibit along an order-criticality-chaos spectrum. Systems within the Poised Realm may be characterized by any degree of order along this spectrum. In some embodiments, the physical systems described herein do not exhibit full order or chaos and are thus also "poised" between order and chaos. Below we describe new theorems which establish that WITHIN the poised realm itself, ie not classical, critical poised realm systems in the presence of decoherence lose coherence most slowly, that is in a power law fashion, while ordered or chaotic Poised Realm systems lose coherence exponentially, hence decohere much faster in the absence of recoherence.

As used herein, "recoherence" refers to a system entering again into a superposition state after it once lost its coherence. The term "recoherence" commonly refers to the re-emergence of some initial quantum state during coherent quantum evolution, which is different from the meaning used herein.

Figure 1:
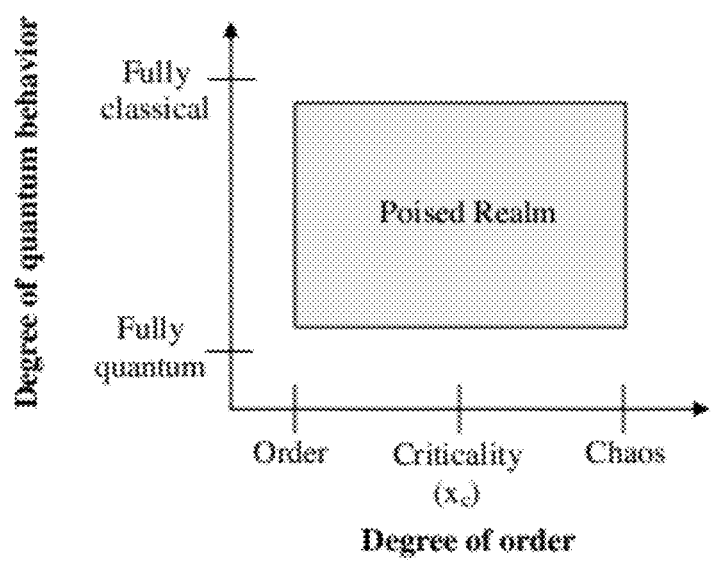
FIG. 1 is graph depicting the boundaries of the Poised Realm.

Thus in at least one characterization of the Poised Realm, the Poised Realm may be illustrated by a two-dimensional coordinate system having as its y-axis (the vertical) the degree of quantum behavior, stretching from fully quantum behavior at the "origin" to fully classical behavior "up" the y axis, typically by decoherence and movement down the Y axis toward quantum behavior via recoherence, and on the x-axis (the horizontal) the degree of order, stretching from full order to full chaos (see FIG. 1). The area on the graph between fully quantum and fully classical behavior is at least one definition of the "Poised Realm." The y axis in FIG. 1 can be infinite in that classical behavior in some circumstances, in particular via increasing quantum decoherence, can be approached as closely as wished, i.e., achieved "For All Practical Purposes" (FAPP).

Thus, as used herein, a "fully classical" system or a system that is "classical for all practical purposes" is a probabilistic mixture of single amplitudes. A "fully quantum" system is one in which all or at least one of quantum degrees of freedom comprise a superposition of possibility waves. Other possibilities or amplitudes may have lost superposition and be comprised by one "pure state" amplitude or a set of pure state amplitudes called a "mixed state". These terms may be understood by the classical double slit experiment, where photons in coherent fully quantum states exhibit an interference pattern. If a detector is used at one or more of the slits, interaction with the detector causes the photons' wave functions to collapse such that they are no longer quantum coherent (i.e., they exhibit classical behavior), resulting in loss of the interference pattern.

Degree of Order

The system in general can be described by its Hamiltonian H. Classical trajectories of the system can be calculated from the Hamiltonian via solving its Hamiltonian equations. Quantization of the Hamiltonian results in the Hamiltonian operator $\hat{H}$, which fully describes the system's quantum dynamics via the Schrodinger equation. The Hamiltonian may depend on several parameters of the system. By changing the parameters of the system we can change the form of its Hamiltonian. Later we refer to this as "changing the Hamiltonian".

By changing the Hamiltonian we can change the degree of chaos in the system. Degree of chaos of trajectories can be characterized by their Lyapunov exponents. One can assign a Lyapunov exponent to each point in the phase space by calculating the Lyapunov exponent of the trajectory initiated in the point. In the phase space one can find connected areas where the Lyapunov exponent is positive and characterized by the same value within the patch. These chaotic patches are separated by regular areas, where the Lyapunov exponent is zero. The degree of chaos in the system can be characterized by the relative proportion of the volume of the chaotic areas in the phase space. If no chaos is present, the proportion is zero. If the system is chaotic for almost all initial conditions the proportion is 1. The position of the system on the x-axis (the horizontal) is this ratio. Usually changing a parameter of the Hamiltonian such a way that its Hamiltonian equations become more nonlinear increases the degree of chaos and moves the system to the right on the x-axis.

In the process of moving the system to the right on the x-axis new chaotic areas emerge, the size of the existing areas increase and separation of some of the existing chaotic areas disappear. There is a critical point on the x-axis, $x_c$, below which the chaotic areas form separated patches in the phase space. Above the critical point the chaotic areas coalesce and form a giant connected component. Below the critical point chaotic trajectories are confined within their chaotic area in the phase space. Above the critical point chaotic trajectories can diffuse globally in the phase space.

In the critical point the Lyapunov exponent for the globally connected chaotic area is zero and it goes through a second order phase transition in the neighborhood of the critical point. It is zero $\lambda_0(x_c)=0$ below the critical point $x < x_c$ and shows power law scaling $\lambda_0(x) \sim (x-x_c)^\beta$ above $x > x_c$ with some positive exponent $\beta$.

Some quantum systems, such as spin systems are defined only with their Hamilton operator and their classical Hamiltonian cannot be defined. In such systems the x-axis and its critical point can be defined purely quantum mechanically. In the pure ordered regime the phase space motion happens on a torus. Quantum mechanically it is a separable system and its eigenenergies correspond to the quantization of its tori. The energy eigenvalues of the system follow Poissonian distribution. The nearest neighbor level spacing distribution is exponential:

$$p_P(s) = \exp(-s)$$

where $s_n = (E_{n+1}-E_n)/\Delta(E_n)$ is the level spacing measured in the units of local mean level spacing $\Delta(E)$ at energy E. In the purely chaotic system the energy level statistics of the system can be described by Random Matrix Theory (RMT) and the level spacing follows approximately the Wigner surmise:

$$p_W(s) = \frac{\pi s}{2} \exp(-\pi s^2/4)$$

These limiting cases correspond to the values 0 and 1 on the x-axis respectively. In an intermediate situation, where the system is neither fully ordered or fully chaotic, the quantity $$x = \frac{A - A_p}{A_w - A_p}$$

can serve as the x-coordinate where $$A_p = \int_2^\infty p_P(s), A_w = \int_2^\infty p_W(s),$$

and the quantity A is calculated from the actual level spacing of the system $$A = \int_2^\infty p(s).$$

In the above mentioned quantum systems the criticality can be defined in a purely quantum mechanical way. In the ordered region the eigenfunctions of the Hamilton operator are localized in configuration space. In the chaotic region the eigenfunctions are delocalized and extended over the configuration space of the entire system. The critical value $x_c$ separates these two behaviors. The level spacing statistics in the critical point can be well approximated by the semi-Poissonian distribution $p(s)=4s \exp(-2s)$.

Systems in nature don't exist in full separation. They are coupled to their environment. Coupling a low dimensional quantum system to an infinite degree environment exert random forces on the system. The system loses its quantum coherence as a result. The environment-system coupling can be described by the Hamilton operator $\hat{H}=\hat{H}_s+\hat{H}_{e-s}+\hat{H}_e$, where the Hamiltonian operators correspond to the system $\hat{H}_s$, to the environment-system coupling $\hat{H}_{e-s}$ and to the environment $\hat{H}_e$. The strength of the external forces causing decoherence is measured by the variance of system-environment coupling averaged over the states of the environment $\Gamma^2 = \langle \hat{H}_{e-s}^2 \rangle$ The position of the system on the y-axis (the vertical) is the ratio of $\Gamma$ and the average level spacing $\Delta(E)$ of the system $\hat{H}_s$.

Some embodiments include modulating or controlling the degree of order of a physical system (i.e., moving along the x-axis of FIG. 1). Some such embodiments include engineering a system to have a desired degree of order. In various embodiments, the following describes, without limitation, three methods for controlling the degree of order in a system.

1) Position on the x-Axis Due to the Hamiltonian of a System.

In general, altering the Hamiltonian of the system by any means may alter its position on the x axis. More specifically, due to the dynamics of the Poised Realm system ITSELF, the classical Hamiltonian of the system can change, changing its position on the x-axis statically or, as we will see, dynamically, as one non-limiting example, from order to criticality to chaos and back.

Classical dynamical systems are often describable as flows on a Hamiltonian. Such flows can, for example, and without limitation, describe most classical physical dynamical systems. A periodic pendulum is a simple example of a system in the ordered classical regime describable by a Hamiltonian. Analogous quantum oscillators are also in the ordered regime. Other Hamiltonians can be critical or chaotic classically.

The dynamical behaviors of such classical systems can be ordered on the x-axis from ordered to critical to chaotic, by means of diverse measures of their dynamical behavior. Several such methods are known in the art. Without limitation, a preferred method to array classical Hamiltonian dynamical systems on the x-axis is by measuring their average Lyapunov exponent, as is known in the art, averaged over the time behavior for short times and from multiple initial states of the system in question. The Lyapunov exponent measures whether nearby trajectories diverge, (chaos), converge, (order), or flow parallel to one another, (criticality), in state space. Account can be taken of the attractor basin sizes, should the classical system have both at least one attractor and may have more than one attractor, each "draining a basin of attraction." Then, typically one measures the Lyapunov exponent on each attractor and weights these by the basin sizes of that attractor, averaged over all attractors, to get a global measure of position on the x-axis. Alternatively, the Hamiltonian system may have no attractor, as in classical statistical mechanics and exhibit ergodic behavior, and satisfy the Louiville equation, as is known in the art.

Thus, classical systems can be moved on the x-axis by "tuning" their Hamiltonians. As we will see, in the Poised Realm quantum degrees of freedom can become classical or classical for all practical purposes, FAPP, and thereby alter the classical Hamiltonian of the system, so the very dynamics of Poised Realm systems can move the classical degrees of freedom from order to criticality to chaos and back.

2) Supression of Decoherence.

Systems in the poised realm can be characterized by their position on the x and y axes in terms of chaos-order and the strength of the coupling to the environment. Depending on their position they are exposed to the decoherence caused by the environment. Quantum systems can be described by their density matrices ($\rho_{nm}$) as it is known to the art. Theoretically, the decay of coherence can be characterized by the speed the off diagonal elements ($n \neq m$) of the density matrix die out $\rho_{nm} \sim e^{-t/\tau_c}$; where $\tau_c$ is the coherence time. An overall measure of the speed of the loss of the coherence is the entropy production in the system. In practice the production of the standard Shannon ($S_1 = -\text{Tr}[\rho \log \rho]$) entropy and the more easily computable Renyi entropy ($S_2 = \log \text{Tr}[\rho^2]$) are used.

The exponential time dependence of the off-diagonal elements of the density matrix and the entropy production rate are closely related:

$$\frac{dS_{1 or 2}}{dt} \sim \frac{1}{\tau_c}$$

Entropy production due to decoherence is related to the dynamical properties of the system. It has been shown via semiclassical arguments and direct simulations that after an initial transient the entropy production rate is related to the Kolmogorov-Sinai entropy ($h_{KS}$) of the dynamical system:

$$\frac{dS_1}{dt} \sim h_{KS} = \sum_i \lambda_i^+$$

which is in turn the sum of the positive Lyapunov exponents $\lambda_i^+$ characterizing the exponential divergence of chaotic trajectories. Entropy production becomes slow when the largest Lyapunov exponent and the Kolmogorov-Sinai entropy of a system vanishes ($h_{KS} \approx \lambda_o \to 0$). In this case the coherence time becomes formally infinite $T_c \to \infty$ indicating a slower than exponential decay of coherence in the system, where the off diagonal elements of the density matrix stay finite or die out only in an algebraic way $$\rho_{nm}(t) \sim \frac{1}{t^\alpha}$$

where $\alpha$ is the exponent of the power law decay.

The zero entropy production state emerges in mechanical systems at the border of the onset of global chaos $x_c$ of the classical counterpart of the system. In quantum systems without classical counterpart the transition happens also at $x_c$, where $x_c$ is now defined in terms of the critical level spacing $p(s) = 4s \exp(-2s)$.

Suppose, we have a parameter $\epsilon$ of a mechanical system which characterizes its transition from integrability to chaos:

$$H = H_0 + \epsilon H_1.$$

Here $H_0$ is the Hamiltonian of an integrable system. Classically and quantum mechanically it is a solvable system. Classically it can be described by action-angle variables and it does only simple oscillations in the angle variables. The phase space motion happens on a torus. Quantum mechanically it is a separable system and its eigenenergies correspond to the quantization of its tori. The energy eigenvalues of the system are random and follow a Poissonian distribution. The nearest neighbor level spacing distribution is exponential $$p(s) \exp(-s);$$

where $s_n = (E_{n+1} - E_n)/\Delta(E_n)$ is the level spacing measured in the units of local mean level spacing $\Delta(E)$ at energy E. The Hamiltonian $H_1$ is a perturbation. When $\epsilon \neq 0$ the system is no longer integrable classically and no longer separable quantum mechanically. At a given small $\epsilon$, the Kolmogorov-Arnold-Moser (KAM) theory describes the system. The perturbation breaks up some of the tori in the phasespace and chaotic diffusion emerges localized between unbroken, so called KAM tori. Chaotic regions are localized in small patches in the phasespace surrounded by regular parts represented by the KAM tori. At a given critical KAM tori separating the system gets broken and the chaotic patches merge into a single large chaotic sea. Above the transition $\epsilon > \epsilon_c$, the system is fully chaotic characterized by a positive largest Lyapunov exponent $\lambda_o > 0$. The energy level statistics of the system can be described by Random Matrix Theory (RMT) and the level spacing follows the Wigner surmise:

$$p(s) = \frac{\pi s}{2} \exp(-\pi s^2 / 4).$$

For our purposes the most important region is $\epsilon = \epsilon_c$. In the transition point the Lyapunov exponent is zero and it goes through a second order phase transition in the neighborhood of the critical point. It is zero $\lambda_o(\epsilon) = 0$ below the critical points $\epsilon < \epsilon_c$ and shows power law scaling $\lambda_o(\epsilon) (\epsilon - \epsilon_c)^\beta$ above $\epsilon > \epsilon_c$ with some positive exponent. At the transition point the level statistics is a special universal statistics called semi-Poissonian:

$$p(s) = 4s \exp(-2s).$$

In this transition point where entropy production is zero, the system is the most robust against decoherence and a system can stay coherent for an anomalously long time in this point. Below the transition point the system is localized and no global transport is possible. Although entropy production is low in this region the system is not suitable for complex transport and also decoherence is strong as each separate localized patch in the phase-space supports a localized wave function quantum mechanically. Each patch is affected by decoherence in a direct way and coherence is lost exponentially rapidly. Far above the transition point strong chaos induces mixing and entropy production which causes rapid decoherence. Near the transition point from above, however metastable states are formed and the wave functions show critical fractal structure. The complex geometry and spatial structure of these transitional states is able to avoid the effects of decoherence most effectively.

The transition described above is much more general than just the integrable-chaotic transition. An example is the metal-insulator transition point. Such localization-global transport (conductance) transition is present when we add static random potential to a clean and perfectly conducting lattice. At a critical level of the added random potential the system stops conducting and the system becomes insulating due to Anderson localization of its wave-function. In this system the control parameter $\epsilon$ is the variance of the random potential. The energy level statistics of the metallic system is described by RMT and the localized states produce Poissonian statistics. In the transition point semi-Poissonian statistics emerges. The same transition can occur also in the conducting properties of random networks (graphs). There the localization-global conductance transition occurs at the percolation threshold, where the giant component of the network emerges. Finally, the same transition can be seen in finite quantum graphs by changing its geometry in specific ways.

In all these systems the metal-insulator critical point is characterized by a fractal structure of the wave function similar to those in the chaos-integrability transition. Moreover, the equivalence of the metal-insulator and chaos-integrability transitions has also been proven analytically. Therefore it seems reasonable to claim that the suppression of the decoherence is also a universal feature of the critical point of the metal-insulator transition. We can suppress decoherence and keep our system coherent for an anomalously long time if we deliberately keep it in the transition point. We call this state the Poised Realm Critical.

Experimentally, the Poised Realm Critical state can be identified by measuring the decay of coherence in the system. In a non-critical system the coherence decay is exponential in time. The Poised Realm state is signaled by a slow, typically power law decay of coherence. State of the art coherence decay measurements are based on various echo measurements depending on the system studied. This includes spin echo, neuton spin echo, and photon echo.

3) Position on the x-Axis is Tunable by the Detailed and/or Statistical Structure of Quantum Networks and Graphs.

As known in the art, quantum graphs and quantum networks may be used to model real systems such nano-structures. During dynamical behavior of a Poised Realm system, the structure of a quantum network corresponding to a real system can change, altering position on the x-axis.

Figure 2:
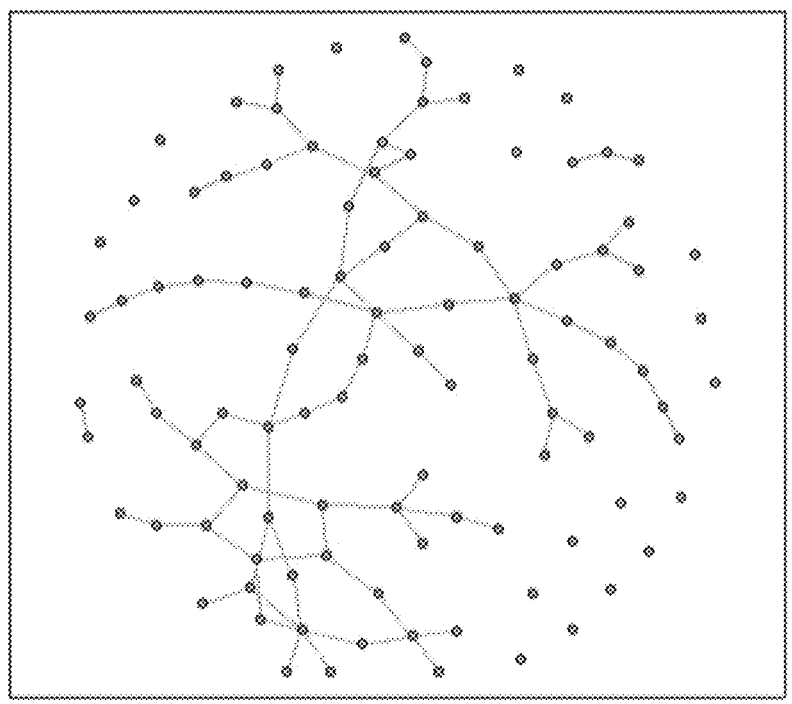
FIG. 2 is a graph depicting an Erdos-Renyi Random Graph with Giant Component.

It is convenient to start with the famous Erdos Renyi (ER) Random Graphs as the simplest possible examples of quantum networks. An ER graph is "grown" by starting with a set of N disconnected nodes. Random pairs of nodes are chosen, and joined by a "line" or "link". This process is iterated, so that at any point, some ratio of links/nodes exists. ER graphs are extraordinary and have driven much research. Most importantly, they exhibit a first order phase transition from essentially disconnected tree "subgraphs" to a single "Giant Component." Define a "cluster" as a set of interconnected nodes. When the ratio of links/nodes is less than 0.5, the graph consists of isolated pieces. As 0.5 is approached, initially small tree-like structures become larger and larger. At link/node ratio 0.5, when the number of ends of links equals the number of nodes, the phase transition to a Giant Component occurs. Intuitively once there are a few very large tree-like graphs for an arc/node ratio a bit below 0.5, a few randomly connected nodes will tie all or most of the large tree-like nodes into the Giant Component (see FIG. 2).

Amazing things happen at this phase transition. Not only does the giant component come to exist, but for the first time loops of all lengths emerge in the giant component.

At the critical ratio of links/nodes, 0.5, the ER graph is said to be "critical". But many nodes are still not connected.

As the ratio of links/nodes increases past 0.5 two major things happen. Isolated nodes and small trees are tied into an enlarging Giant Component. Second, the Giant Component becomes increasingly richly cross connected, so average $<k>$ rises.

Such graphs can be considered static quantum networks. Their structure is given by an Adjacency N×N matrix, with a 1 in matrix element i,j if there is a connection between nodes i and j. By symmetry, the j,i matrix element is also 1. Otherwise, for all pairs that are not joined by a line, the matrix element in the Adjacency matrix is 0.

Figure 3:
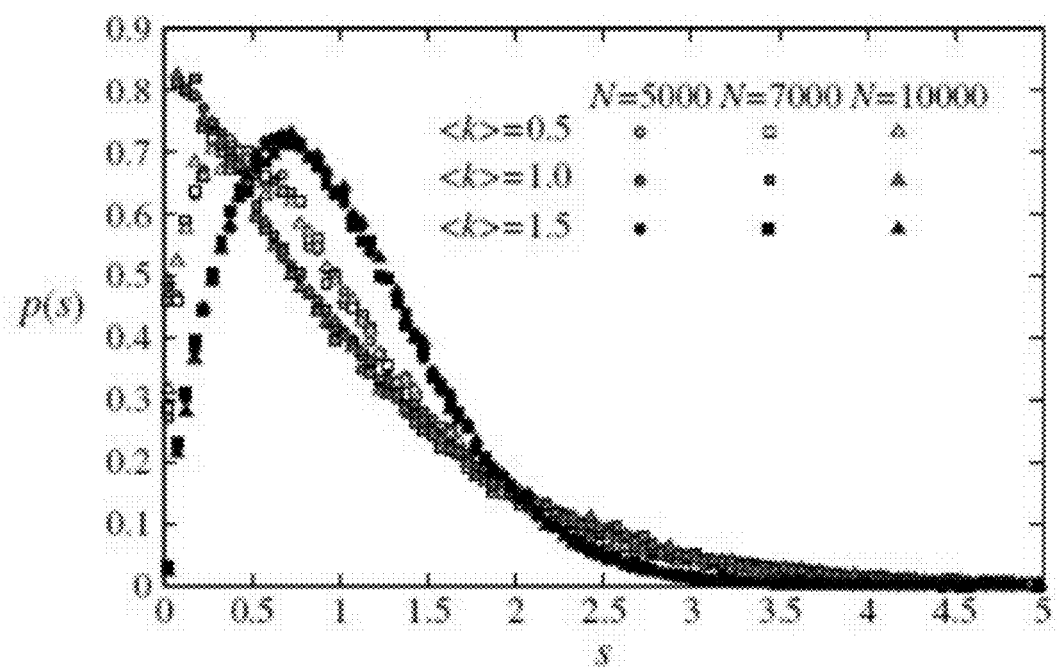
FIG. 3 is a graph depicting the energy level spacing for Erdos-Renyi random graphs.

The eigen values of the Adjacency matrix give the energy levels of the quantum network. From this one can compute the "energy jumps" between all pairs of energy levels, and from this the distribution of energy jumps, or quanta sizes, in the ER subcritical, critical, or supracritical="chaotic" quantum networks FIG. 3 shows the spectrum of critical, and 2 successively more supracritical networks, mean ratio lines/nodes=$<k>$=0.5, 1.0 and 1.5. All have giant components which, since they contain most of the nodes, dominate the eigen value spectrum.

These results show that in ER critical and supracritical graphs, position on the x-axis, critical or chaotic, can be attained by modification of the quantum network structure.

The quantum networks above are structures, realizable, for example, by networks of carbon nanotubes capable of quantum behavior. Molecular systems can also be regarded as quantum networks. Below we discuss two generic models of quantum degrees of freedom: quantum rotors and quantum oscillators. It will be clear to those of ordinary skill in the art that arbitrary graphs can be endowed with quantum oscillators and/or rotors at, without limitation, some or all nodes, and their quantum and order-critical-chaos behaviors studied. Without limitation, quantum oscillators can be coupled in arbitrary topologies to one another by interactions (for example spring-like harmonic interactions). To date, most work has focused, as we will describe, on single "kicked" quantum rotors, or two coupled quantum oscillators coupled by a spring and/or coupled to a quantum oscillator "heat bath," as is known in the art. These models are fully extendable to arbitrary networks, as above, as the quantum system in an arbitrary quantum environment. As discussed below, these models, in particular, networks, are suited to model chemical molecules, will be applied to the evaluation of candidate drugs and the behaviors of nanotube structures.

As noted above, one method of controlling position on the x-axis is to change the network structure. For example in our application of these ideas to drug design and nano-technology design, a given network can model a molecule. By adducting to it another molecule, say by hydrogen bonds or other non-covalent interactions, the graph structure of the new network can be made less than critical, critical, or more supracritical.

We note that networks of more arbitrary structures can be made with carbon nanotubes or other materials, than can be made with atoms such as carbon, hydrogen, nitrogen, oxygen, phosphorus, and sulfur, due to the bonding properties of these specific atoms.

Controlling the Topology of the Quantum Networks Via Proximity of the Nodes

Consider as a non-limiting example a set of chromophores, parts of molecules or independent molecules. Electron exchange is one means of linking the chromophores, as a non-limiting example.

The details of this interaction depend upon the detailed positions of the chromophores. However, in general, if they are sufficiently close, so each chromophore can communicate with many neighbors, many closed quantum loops will exist and the quantum network will be supracritical, hence "chaotic". If further apart, the quantum network will be less connected, and critical or subcritical, moving thereby on the x-axis. As we see below, chromophores bound to the membrane of a liposome can be made more or less chaotic on the x-axis by subjecting the liposome to hypertonic or hypotonic media that shrink or swell the liposome.

As used herein, a generalized "chromophore" refers to any quantum network of interacting elements.

In general, these quantum networks may be on rigid structures such as nanotech devices (e.g, carbon nanotube structures). Or they might be inside or outside or both of a liposome, made as is known in the art, as a bilipid double membrane hollow vesicle, with the chromophores anchored to the bilipid double membrane via covalent bonding to beta barrel proteins spanning such bilipid layers. The density per liposome of generalized or specific chromophores in the general sense used here can be tuned through a wide range. As described later in the section on embodied algorithmic or NON-ALGORITHMIC trans-Turing Machine quantum-Poised Realm-classical information processing systems, which might be nanostructures or liposomes or other vehicles, liposomes can be constructed from lipids in water containing the beta barrel proteins with attached chromophores. One expects a random distribution of chromophores inside and outside the liposome membrane, allowing such a structure to receive quantum information via the external chromophores and internal chromophores where light, or other quantum degrees of freedom without limitation, reaches to and across the membrane. The set of all the chromophores form a quantum graph that, together with the liposome and aqueous interior with chosen concentrations of ions and other small and larger molecules, will behave in open quantum, Poised Realm, and classical ways, as described below, for example without limitation via repeated decoherence and recoherence of quantum degrees of freedom to classicity, which degrees of freedom when classical, or classical (for all practical purposes, FAPP), will alter both the classical Hamiltonian of the system, and thereby also alter the Hamiltonian of the quantum degrees of freedom. Similarly the recoherence of a classical degree of freedom, as discussed below, will alter both the classical and quantum Hamiltonians of the system, hence the total behavior of the coupled classical and quantum system over time. These facts are useful in Trans-Turing systems, below.

We also note here that quantum measurement can occur in the Poised Realm, in the presence of decoherence and recoherence. Measurement may be achieved, without limitation, by any means. As a central non-limiting example, the classical degrees of freedom of a system above, as in our Trans-Turing systems below, themselves constitute part or all of the quantum measuring system which can measure, in some basis, one or more of the quantum degrees of freedom of the system.

4) Position on the x Axis May be Controlled by Pulsed Stimulation.

A third method to control position on the x-axis (i.e., degree of order), is by pulsed stimulation. This method may be modeled by a kicked quantum rotor. Basically a quantum rotor is a quantization of a classical rotor on a frictionless stand that is spinning with some frequency. If the classical rotor is tapped with "Dirac delta" inputs of momentum gently, it remains in the ordered regime, hence left on the x-axis. As it is kicked harder and harder, it moves out on the x-axis, becomes critical, then chaotic. The same holds for quantum rotors as we describe below in detail. In the quantum case, the quantum rotor degree of freedom is kicked with Dirac delta laser light momentum kicks where the intensity, "K," of the kick can be increased, driving the rotor from order to chaos. This characteristic is expected to extend to systems having arbitrary Hamiltonians. Thus, one embodiment includes modifying the state of order or chaos of a system by stimulating the system pulsed light.

It is expected that quantum rotors or other Hamiltonians kicked to ordered, critical or chaotic states will exhibit different quantum energy level distributions. Thus, measurement of such distributions (e.g., through spectral analysis) demonstrates the degree of order of such a system. Thus we can readily test for position on the x-axis.

For real quantum systems, an issue is at what light frequency to kick the quantum system. In one embodiment, the center of one or many of the absorption/emission band(s) of that quantum degree of freedom or a set of quantum degrees of freedom is used for the stimulation.

Degree of Quantum Behavior

For actual physical systems, which can be modeled with quantum network structures, the molecular topology of the system can tune the decoherence rates, and thus movement on the y-axis, in the processes engendered by the system. The electronic energy transfer in chlorophyll is the best example of such a system with both theoretical and experimental results showing long-lived quantum coherence in an intrinsically noisy cellular environment. Hence the structure of chlorophyll may play a major role in resistance to decoherence.

Movement from Quantum to Classical Via Decoherence.

Decoherence is a well established phenomenon and the current favored explanation of the transition from the quantum to the classical worlds. In quantum mechanics, the signature interference pattern due to constructive and destructive interference can only occur if all the phase information is present in the quantum system. But in an open quantum system, phase information can be lost from the quantum system to the environment in an irretrievable way. As this happens, the capacity for interference patterns in the quantum system decays.

There are at least two 'as if' models of decoherence. The best established is the "Lindblad operator", which allows the off diagonal elements of the density matrix of the system containing the phase information to decay.

A second model of decoherence makes use of a random walk process called either a Weiner process, $\sigma Wdt$. In a Weiner random walk process, the Weiner noise term is a random Gaussian variable with mean 0 and a variance, $\sigma$. The larger $\sigma$ is, the larger is the average random phase step on the orbit in the complex plane of the quantum degree of freedom, such as the quantum rotor.

We have focused in our simulations of the kicked quantum rotor on the Weiner process, but have also used the Lindblad operator. In the Weiner process, a variance of 0, $\sigma=0$, is "no coherence," hence quantum on the y-axis. As $\sigma$ increases, the noise increases, and the rate of decoherence increases.

In the Quantum Zeno effect, demonstrated experimentally, a quantum degree of freedom is measured very frequently. Each time it is measured, by von Neumann, it falls to a single amplitude, or eigen state. It then slowly, quadratically in time, leaves that quantum eigen state and "flowers" to populate nearby and then more distant amplitudes of that quantum degree of freedom. However, if it is frequently measured, it is almost certainly "trapped" in its initial quantum eigen state, and the time evolution of the Schrodinger equation is stopped. As it flowers to nearby amplitudes it becomes a superposition state again, moving up the y-axis. So frequent measurements, tunable, can keep a quantum system near classical or somewhat quantum because only a small number of amplitudes have "flowered," hence control position on the y-axis.

Passing from Classical or Classical FAPP to More Coherent or Fully Coherent, i.e., Down the y Axis.

One embodiment includes driving a system to be more coherent including driving a classical system back to quantum. One embodiment includes driving a classical system into the Poised Realm.

We consider a time independent (autonomous) quantum system described by the Hamiltonian H under the action of a time dependent external potential $U(x; t)$. We can separate the coherent and temporally random parts $U(x; t)=V_r(x; t)+V_c(x; t)$. The random part causes decoherence while the coherent part causes re-coherence in the system. Assuming that the random part is uncorrelated in time and using Ito's rule we can get the time evolution of the averaged density matrix $$\partial_t \zeta(x, x', t) = -\frac{i}{\hbar}[\hat{H} + \hat{V}c, \zeta(x, x', t)] - \frac{1}{\hbar^2}\Gamma(x, x')\zeta(x, x', t), \quad (1)$$

where $\tau(x,x')=C(x; x)+C(x', x')-2C(x, x')$ and $<V_r(x,t)V_r(x, t')>=C(x,x')\delta(t-t')$ is the temporal autocorrelation of the random potential at different spatial sites $x$ and $x'$. In most relevant situations a simple discrete Hamiltonian can describe the system with matrix elements $H_{nm}$ and the simplest delta correlated noise can be assumed $C_{nm}=C\delta_{nm}$ and $\Gamma_{nm}=\Gamma(1-\delta_{nm})$. The coherent external potential, which can come from laser pulses or any other coherent electromagnetic source, can be reasonably modeled with a sequence of sharp kicks $\hat{V}_c(x; t)=\Sigma_n V(x)T\delta(t-nT)$ at times $nT$.

In absence of the coherent part the evolution of the density matrix is described by $$\partial_t \rho_{nm} = -\frac{i}{\hbar}\sum_k (\hat{H}_{nk}\rho_{kn} - \rho_{kn}H_{km}) - \frac{\Gamma}{\hbar^2}(1-\delta_{nm})\rho_{nm}.$$

Decoherence kills quantum superposition states represented by the off-diagonal elements of the density matrix. The density matrix settles to the diagonal form $\rho_{nm}=\delta_{nm}P_n$, where $P_n$ is the classical probability of finding the system in state n. The characteristic decay time is $h^2/\Gamma \sim 10$-$100$ femtoseconds. The coherent part is able to re-create superposition states. The density matrix before and after the coherent kick is $$\rho_{nm}^+ = \sum_{n'm'} U_{nn'} U_{m'm}^* \rho_{n'm'}^-$$

where the unitary matrix $U=\exp(i\hat{V}_c T/h)$ describes the action of the kick on the wave function.

Even if the density matrix is diagonal before the kick $Q_{nm}^-=\delta_{nm}P_n$ it becomes non-diagonal after the kick $$\rho_{nm}^+ = \sum_k U_{nk} U_{km}^* P_k,$$

indicating the presence of superposition states. Kicking the system repeatedly can repair the coherence lost during time evolution and keep the system levitating at the border of the 'realms' of quantum and classic. The interplay of the coherent kicks and decoherence determines the speed of the loss of coherence in the system.

Evidence of that systems can be driven to more quantum behavior include the following:

1) In the Zeno Effect, the system is trapped in one eigen state, hence classical during the interval before remeasurement. If not remeasured, the system again flowers multiple quantum amplitudes quadratically in time. One means by which such reemergence of quantum amplitudes happens is in a system which is a quantization of a classical chaotic dynamical system. One of the quantum amplitudes of the localized quantum behaviors of the quantum system is measured, causing the system to collapse to a single possibility via the Born Rule and is briefly Quantum Zeno Effect "trapped" in the eigen-state. This amplitude emerges quadratically in time to repopulate other quantum amplitudes with finite moduli.

2) A second means known in the art to regain quantum coherent behavior concerns quantum entangled degrees of freedom in a quantum squeezed state. For specific systems, quantum entanglement can undergo "Sudden Death", can undergo No Death, and can undergo Sudden Death and Revival. Such Revival is a revival of coherent entangled quantum behavior from far in the classical region (FAPP or entirely classical). We incorporate by reference, "Entanglement dynamics during decoherence", J. P. Paz, A. J. Roncaglia, Quantum Inf Process (2009) 8 535-548 in it's entirety. We also incorporate by reference in their entirety "Entanglement and intra-molecular cooling in biological system?—A quantum thermodynamic perspective." H. J. Briegel and S. Popescu Phys arXhiv 0806,4552V2 [QUANT-PH] 5 Oct. 2009 and "Dynamic entanglement is oscillating molecules", J. Cai, S. Popescu and H. J. Briegel arXhiv:0809.4906v1 [quant ph] 29 Sep. 2008. The last two articles computationally demonstrate and suggest recurrent passage from coherent entanglement to classical behavior and back. The last paper posits conformational changes of a biomolecule induced by interaction of some other chemical at an allosteric site.

3) A third means known in the art to regain coherence is given by the Shor Theorem, which states that in a quantum computer with entangled quantum degrees of freedom, the quantum system can be quantum measured using quantum degrees of freedom not part of the qubit calculation. Information can be injected from outside the quantum computer that restores quantum coherent behavior to the decohering quantum degrees of freedom, i.e., qubits.

4) A fourth means that induces increased coherence in a quantum or partially quantum, partially decoherent, and perhaps partially fully decoherent system almost certainly occurs in chlorophyll wrapped by its evolved "antenna protein." At 77 degrees K, the expected time scale for decoherence is on the order of a femtosecond. The chlorophyll molecule, having been excited by absorption of a photon by an electron, remains in the quantum coherent (or largely coherent) state for at least 700 femtoseconds.

It is believed that this astonishingly long lived coherent state is due to the antenna protein. This can be experimentally verified by use of mutant antenna proteins, and this has been done with the antenna protein and its mutants for a bacterial rhodopsin molecule, where loss of coherence occurs with mutant antenna proteins. Long lived quantum coherence may also be partially due to the quantum graph structure of chlorophyll.

It may be that the antenna protein entirely blocks any decoherence to the full environment of the chlorophyll molecule. It is more likely that the antenna protein, filled with chromophores, acts on the chlorophyll molecule by driving it with photons in a physically realized version of some type of Shor theorem, to inject information into the chlorophyll and sustain or restore coherence to the chlorophyll molecule. But restoring coherence means that in physical reality, the antenna protein can increase coherence in quantum degrees of freedom of the chlorophyll molecule. The topology of the chlorophyll molecule may play a role either in its resistance to decoherence, or ease of recoherence via input from the antenna protein.

Chlorophyll and its antenna protein is a probable example of a fourth general means to drive a system from classical due to decoherence and phase randomization as above, by kicking the quantum degree of freedom at exactly the natural frequency of any one or a plurality or all of its quantum amplitudes. Think of a classical rotor whose phase is being randomized by modest sized hammer kicks at frequencies that are irrational with respect to its natural frequency. Now hit it with a hammer of tunable size at its natural rotation frequency. You will tend to or will overcome the modest sized hammer irrational "noise" taps and resynchronize the classical rotor. In the same way, consider a quantum degree of freedom with a sharp band spectrum. Each band is the exact frequency of light that must hit that quantum degree of freedom with high intensity to resynchronize its phase and drive the classical, decoherent degree of freedom down the y-axis through the Poised Realm toward fully quantum behavior. Almost certainly, the antenna protein chromophores are doing this, a hypothesis which is testable by mutating the chromophores and showing that sustained coherence of chlorophyll decreases then correlating the decreased coherence with a change in the emission spectra of the chromophores on the antenna protein with respect to the absorption/emission spectrum of chlorophyll. This experiment as been done with a bacterial rhodopsin and its antenna protein with exactly the above result, although matching to the emission frequencies of the antenna protein and absorption bands of chlorophyll have not, to our knowledge, been examined.

Additional data has shown that, in a spin bath environment, a quantum system can exhibit partial decoherence that levels off with medium coherence, in the Poised Realm, where coherent behavior propagating a finite number of coherent amplitudes persists indefinitely. If the system is started with less coherence, ie "more classical" in the Poised Realm, it recoheres to the same intermediate level, propagating a finite number of quantum amplitudes coherently. Such stable propagating amplitudes that persist despite decoherence are useful in quantum computation.

As discussed above regarding the degree of order, decoherence can be suppressed and the system kept coherent for an anomalously long time if it is deliberately kept at the Poised Realm critical transition point. Within the poised realm, ordered and chaotic behavior is associated with rapid exponential decoherence. In sharp contrast, along a critical locus in the poised realm roughly paralleling the y axis and terminating at criticality on the x axis, poised realm systems decohere much more slowly, in a power law, not exponential decay of coherence. Thus, within the poised realm, criticality preserves coherence better than other positions within the poised realm.

Measuring Decoherence and Recoherence Experimentally in Real Quantum Systems.

There is a very convenient measure of decoherence. A dilute gas of a single atomic species, e.g., hydrogen, has very sharp absorption and emission bands, forming its spectrum. In general, as decoherence sets in, these bands become wider. Thus, the width of a band is a convenient measure of the decoherence status of that amplitude of the quantum system, which is easy to measure with standard spectrography.

Recoherence can be seen, for example due to driving with light whose wavelength is at the center of a broadened band, by progressive narrowing of that band. Conversely decoherence and its rate can be measured by narrowing and sharpening of the band. And position on the y-axis can be measured at any time for any pair of amplitudes whose energy gap corresponds to that band, by how narrow or broad it is. We can follow position on the y-axis for all pairs of amplitudes of a one or a system of coupled quantum degrees of freedom on a quantum graph, by the breadth of such bands. In addition, coherence can be measured using spin echo experiments.

Our first results modeled decoherence with a Wiener process, σWdt, whose variance sigma could be altered from 0, hence persistently quantum coherent in the absence of any decoherence, to infinite, which randomizes all phases. Thus, in general, as we move by increasing sigma in the Weiner process, we move from quantum to decoherence to classical behavior. For a kicked quantum rotor, position on the x-axis (degree of order) is determined by the intensity of momentum kicks, of intensity K, to the quantum rotor. These kicks are Dirac delta functions—that is "instantaneous" inputs of momentum energy supplied, without loss of generality, by laser light of any diversity of frequencies, and at any rate of photon kicks, i.e., intensity K, to the quantum rotor per unit time.

It will be clear to those of ordinary skill in the art, that the photon kicks can be any quantum degree of freedom and delivered with any time constant or varying modulated intensity, hence the kicks to each quantum degree of freedom are a quantum time modulated input signal to the quantum degree of freedom. Therefore, in general, this quantum input constitutes quantum information received by the rotor. When we generalize to a quantum network with rotors coupled to one another, or more general systems with quantum and classical degrees of freedom, this will become the quantum information via one or a plurality of quantum inputs to a system of quantum and classical degrees of freedom that responds to the incoming quantum information, emits quantum information to its environment, alters its Poised Realm and classical behaviors and also the quantum and classical Hamiltonians, and constitutes a new class of embodied quantum information processing systems that we call Trans-Turing Systems. Due to the superpositions noted above or pure states and the Born rule, coupled with decoherence to classicality or quantum measurement, the Trans-Turing system is not definite, so not algorithmic, but due to the classical degrees of freedom and Poised Realm degrees of freedom, the behavior is also NOT RANDOM IN THE STANDARD SENSE OF QUANTUM RANDOM given by the Schrodinger equation and von Neumann axiomatization of closed system quantum mechanics. We emphasize that our Poised Realm systems in general and Trans-Turing systems are OPEN QUANTUM SYSTEMS, WITH A DISTINCTION BETWEEN THE QUANTUM SYSTEM AND ITS ENVIRONMENT INTO WHICH IT CAN LOSE PHASE INFORMATION.

Decoherence happens in open quantum systems because phase, and also amplitude, information is lost from a quantum system, here our single quantum degree of freedom, to a quantum "environment". For example a photon emitted by an excited electron may, on one of its many possible paths in Feynman sum over histories formulation of quantum mechanics and quantum electro-dynamics, interact with any quantum degree of freedom in the environment and thereby induce decoherence.

In our studies of the driven quantum rotor, we model two processes. We model the kicks, K, which hit the rotor once per arbitrary period. As noted above, we model the decoherence process as a random walk called a Weiner process, described by σW dt. W is a Gaussian distributed 0 mean, 1 variance distribution of "step sizes" which describes the phase change of the point on the circle in the complex plane at each application of the Weiner random walk, during dt. At sigma=0, there is no alteration of phase, hence no decoherence, and the system is fully quantum. Thus, σW dt=0 is the quantum coherent origin of the y-axis. As σ increases to ever larger values, the phase becomes ever "noisier" driven by the white noise Weiner process. Thus as sigma increases the rate of decoherence increases.

A second way we implement quantum measurement of an amplitude in our algorithmic simulations of a Poised Realm system is by taking the square of its modulus, (i.e., the Born Rule), doing so for all amplitudes of the rotor with finite modulus, then choosing one of these amplitudes with a probability corresponding, via the Born Rule, to its squared modulus, and placing the rotor in that single eigen state corresponding to the measured amplitude.

Once the quantum degree of freedom is measured, and in its eigen state, it can leave that eigen state quadratically in time with the "flowering" to finite moduli, of nearby and more distant amplitudes in the absence of decoherence. In short, at $6=0$, no decoherence, full quantum behavior reemerges with all possible amplitudes for the system. At finite sigma, a finite number of amplitudes with finite moduli will flower as noted below.

Quantum Localization of Chaotic Dynamics.

If the classical limit of the quantum system has a Hamiltonian corresponding a position on the x-axis to the right of the critical point second order phase transition, the classical system exhibits chaos. If decoherence is 0 or low enough, because sigma is low enough, quantum behavior occurs, even in the persistent presence of some decoherence, but the quantum behavior is localized. In the Poised Realm, only a finite number of amplitudes have finite moduli.

In short, in the Poised Realm FAPP only a finite and tunable number of amplitudes are present in the quantum behavior of a single quantum kicked rotor degree of freedom, or for any number of independent kicked quantum rotors. The same limited number of amplitudes obtains for kicked quantum oscillators whether single or, if independent, any number.

Energy Scaling of Decoherence.

In our specific, non-limiting example of the use of the Weiner process to model decoherence of any amplitude, we have found that HIGH ENERGY AMPLITUDES ARE ONES MOST LIKELY TO DECOHERE to classical behavior, that is they become classical degrees of freedom, even for small values of sigma. By contrast, low energy, small modulus amplutudes do not decohere to classical behavior as readily.

The preferential decoherence of high energy and high amplitude modes is reminiscent of Fermi's Golden Rule for quantum measurement for coherent systems, where quantum systems tend to take the largest energy drop, eg to the ground state, available. But in turn, as exemplifed by the famous photoelectric effect where absorption of a photon, according to Einstein 1905, kicks out an electron from the material, the TRANSFER OF ENERGY FROM THE QUANTUM AMPLITUDE TO THE NOW CLASSICAL DEGREE OF FREEDOM WILL BE LARGEST IF HIGH AMPLITUDE HIGH ENERGY AMPLITUDES PREFERENTIALLY DECOHERE TO CLASSICALITY FAPP, OR ARE PREFERENTIALLY MEASURED IN THE POISED REALM FOLLOWING FERMI'S GOLDEN RULE. This bears on essential three topics: i, the efficiency of energy transfer in the Poised Realm and Trans-Turing systems; ii. The use we make below of this preferential decoherence of HIGH ENERGY AMPLITUDES to solve the famous FRAME problem in algorithmic computers in our non-algorithmic, non-deterministic, but non-random Trans-Turing systems—see below. iii. We will use the preferential decoherence to classicality FAPP or via measurement, below in Trans-Turing systems such that there is an ongoing decoherence of high amplitude modes to classical behavior, thereby altering the classical hamiltonian, eg as a non-limiting example by altering the couplings among classical degrees of freedom. In turn this will alter the hamiltonian of the quantum degrees of freedom, in turn altering via constructive and destructive interference of superpositions, or of pure states, which amplitudes are of high energy and decohere next in time, again altering the classical and quantum hamiltonians of the trans-turing system. In turn, by recoherence, classical degrees of freedom can recohere, again altering the classical and quantum hamiltonians. This ongoing behavior is the centerpiece of trans-turing non-determinate, non-algorithmic, yet non-random behavior.

With respect to preferential deocherence of high energy amplitudes, we reason that high energy amplitudes have high angular momentum hence are less affected by random decoherence noise, so we have scaled, as a non limiting computational study example, decoherence via the Weiner process to decrease either exponentially or as a power law, with increasing energy of the amplitude. In particular, we use $\sigma = \sigma_0 \exp(E/Eo)$ where $\sigma_0$ is the sigma for a 0 energy amplitude, a constant, E is the energy of an amplitude, and Eo is a scaling factor governing the exponential fall off of Weiner modeled phase decoherence with the energy, E, of an amplitude.

Behavior of a Single Kicked Quantum Rotor in the Poised Realm.

With the above introduction, we find the following: 1) For low enough sigma and all K, i.e., values of the x-axis, the system is quantum and has a finite number of modes or amplitudes. 2) As sigma increases, so decoherence increases and we move up the y-axis in the Poised Realm, there are fewer amplitudes propagating then a transition to classical behavior occurs. Thus classical degrees of freedom emerge as decoherence increases. 3) The slope of this transition from quantum to classical as sigma increases, itself increases as X value, i.e., increasing chaos, increases. That is, more chaotic systems undergo the transition to decoherence more for smaller changes in sigma W than more ordered systems. 4) There is some indication that the midpoint of the slope of this transition to decoherence is "flat" and parallel to the x-axis in the ordered regime, where decoherence requires similar high sigma W as X increases toward criticality, then bends downward in sigma W required for decoherence at criticality, and that decoherence occurs at ever lower sigma, i.e., decoherence inducing phase noise, as chaos increases on the x-axis. This sloping behavior of the midpoint of the transition curve means that motion on the x-axis by any means at a constant sigma W, can move the system from decoherent to more quantum coherent behavior. For example, decreasing or increasing the intensity of the momentum kicks to the quantum rotor can move that rotor from quantum to classical behavior and back as the kicks decrease then increase in intensity. Similarly, altering the graph structure corresponding to a real system from critical to supracritical and back on the x-axis can move the system from coherent to decoherent behavior in the Poised Realm. We make use of this in the section on drug discovery and action below. This is also true as the Hamiltonian of the system is changed on the x-axis, which can occur dynamically as a system of coupled quantum and classical degrees of freedom behaves. This constitutes a new way to move from quantum to classical behavior and back. Thus a single degree of freedom can be quantum or can be classical, either by tuning the position on the x-axis by tuning the kick strength K, or by tuning position on the y-axis by tuning decoherence. So too can a system of coupled quantum degrees of freedom, for example in a quantum graph, or quantum and classical degrees of freedom. For example, a critical chemical quantum network will decohere very slowly, via a power law, not an exponential decay. We have already noted that adducts to a quantum network, or deletions from that network, or alteration in the proximity of generalized chromophores, can alter the effective quantum network topology on the x-axis moving it to or from the critical locus of power law behavior in the poised realm.

It will also be clear to those of ordinary skill in the art that tuning position on the x-axis for a single quantum degree of freedom is at our liberty as it is we who determine kick intensity, K.

Summary of the single kicked quantum rotor in the Poised Realm: 1) only a finite number of quantum amplitudes grow and have finite moduli. The number of modes decreases as kicking intensity increases. 2) In the chaotic region with high intensity kicking, quantum localization of chaotic behavior occurs. 3) A transition from quantum to classical behavior occurs as sigma W dt is increased, i.e., as decoherence is increased, but quantum behavior persists for small finite σWdt. 4 A slope in the transition from quantum to classical behavior along the x-axis is present at some fixed values of σWdt, so any single independent kicked quantum rotor can be moved from quantum to classical by tuning momentum kicking, K, intensity, or decoherence intensity. Or a quantum network can be moved from quantum to more classical behavior by motion out the x-axis toward chaos, and we believe beyond criticality on the X axis. Or motion on the x-axis by change of the Hamiltonian of the system as quantum degrees of freedom become classical and may, as a non-limiting example, couple in new ways to other current classical degrees of freedom, can move the system on the X axis, from more to less quantum behavior in the Poised Realm. 5) A final feature is that behavior in the poised realm is not random, and not Markovian. This behavior partakes of the Anti-Zeno effect, is non-Markovian, hence not first order random, as is normal quantum randomness, and is a Floquet process. The same conclusions generalize to coupled quantum degrees of freedom or quantum and classical degrees of freedom.

Simulations Using the Lindblad Operator.

As described above, the Lindblad operator is a mean field Markovian model of loss of off diagonal terms in the density matrix of a quantum system including a single kicked quantum rotor. It is widely accepted as physically accurate, but is not a detailed "law of decoherence." As noted above, in a Special Relativity setting where the quantum degrees of freedom move with respect to one another there can be no such law. Again, given events A and B, where B is in the future light cone of A, and the past light cone of B includes the past light cone of A, but has regions space-like separated from A, no observer at A can know what events are occurring outside her past light cone. Therefore, there is no way in the Special Relativity setting to write down a law for decoherence in the space time interval from event A until immediately before event B. In general, there is no "law of detailed decoherence."

Yet the Lindblad operator, a meanfield approach to the statistics of this process, serves well, particularly for tiny relative velocities of degrees of freedom.

We have implemented the kicked quantum rotor and increased the frequency and intensity of kicks, such that they vary from ten times the rotation frequency of the rotor to its rotational speed, "continuously". In the ordered regime on the x-axis, the finite number of amplitudes is high, and decreases as the critical phase transition is approached. Thus, the behavior of the system is far from the closed quantum system and unitary propagation of many amplitudes of the Schrodinger time dependent equation. Only a finite number of amplitudes with finite modulus are present.

When the system crosses into the chaotic regime, it becomes fully classical. Thus, as in the case of modeling decoherence with a Weiner process, sigma W dt, the response of the kicked rotor depends on position on the x-axis, so the rotor can be moved from quantum to classical and back by motion on the x-axis.

In this model, the movement on the x-axis is due to the intensity and frequency of Dirac delta momentum kicks. More generally, the results support the claim that motion on the x-axis back and forth, either by momentum kicks, quantum network topology alterations by altering network structure directly with adducts, deletions, or altering the size, and density of generalized chromophores, will alter position in the Poised Realm.

Evolved organic molecules, like all organic molecules, can exist in the Poised Realm. It will be clear to one of ordinary skill in the art, that position in the Poised Realm is likely to affect the behaviors of one or a plurality of molecules, as a non-limiting example, in cells. Thus, position in the poised realm will affect the behavior of drug molecules as well. It becomes of deep interest if EVOLVED organic molecules occupy a specific supspace of the Poiosed Realm. In particular, we believe that evolved organic molecules are likely to be at or near the critical locus in the Poised Realm. This critical location allows such evolved biomolecules and small organic molecules and drugs to participate in the slow power law decoherence of criticality rather than more rapid exponential deocherence as the system moves further towards order or chaos. Quite interestingly, we will see below that biological small molecules appear close to the statistics of the critical giant components in quantum graphs, in our two examples, while cyclic hydrocarbons, Buckmeisterfullerenes, graphite and diamond are much more richly connected and supracritical. This may mean that biological molecules are not purely classical, but may well remain partially poised in the Poised Realm. The quantum coherent behavior of chlorophyll and bacterial photoreceptor systems is opening the field of quantum biology. Much of cell life may hover in the Poised Realm, with new implications for medicine and drug discovery we return to below.

A means to test whether biological molecules are in the poised realm is afforded by the experiments of Anton Zeilinger, University of Vienna, who has shown that C60 Buckmeisterfullerenes, used as a "beam" in a two slit experiment, show partial reduction in interference uniformly across all interference bands, hence are partially decoherent. This procedure is a new means by which to test the coherence of a particular molecule. In the two slit experiment, molecules will show more or less signatures of partial decoherence by greater or less reduction of interference patterns in the two slit experiment. Thus if there is less than normal interference, the molecules are in the Poised Realm in a "stable way".

Drugs in the Poised Realm

It is generally thought that quantum phenomena have no bearing on biological processes because, at body temperature (about 300K), no quantum phenomena would be present. This view is purely one that envisions either a quantum world or a classical world, and the von Neumann R process of "collapse" of the wave function via the Born rule to place all the probability on one amplitude with a probability the square of the modulus of that amplitude. Quantum chemists have typically ignored decoherence, treated most of a molecule with classical physical models with a classical Hamiltonian potential, then at most focused quantum time independent Schrodinger equation analysis of a small "active" part of a molecule, then mathematically "glued" the quantum and classical aspects of the modeled molecule together.

An interesting failure in this regard, where one of us, Kauffman, has the founding patent, is combinatorial chemistry (See Kauffman Ballivet patents 1986 France to 1992 US). The US pharmaceutical companies have spent billions making libraries of more or less random organic molecules then screened these for ligand binding to shape complements of desired drugs. For example, a random organic molecule binding to the estrogen receptor, like a random key fitting the receptor thought of as a classical physics "lock", is a candidate to shape mimic estrogen itself and hence be a drug candidate. This entire approach, which Kauffman and Ballivet invented, treats ligand binding pairs as fully classical physical entities, locks and keys, the then prevailing theory. The approach has failed. The drug companies in the US are said to have nearly empty drug pipelines. By contrast, the Japanese pharmaceutical companies continued over the past decades, we are told, to rely on traditional medicinal chemistry and they have many drugs in their developmental pipelines. This sharp contrast suggests that the medicinal chemists were unwittingly probing the Poised Realm behavior of drug candidates and combinatorial chemistry with its screening or computational designs based largely on classical physics models of all or most of the candidate molecule's structure and dynamics, missed any Poised Realm behaviors relevant to drug action. This bears on our use of the Poised Realm for drug discovery, as well as for understanding basic cell biology.

In the standard view, the world is either fully quantum or fully classical. There is no notion of a Poised Realm between quantum and classical. As described above, data demonstrates that there is in fact a Poised Realm between fully quantum and fully classical. As an example, the long term quantum coherence of chlorophyll is galvanizing quantum physicists and a new field of quantum biology. The antenna protein and its chromophores almost certainly cannot block decoherence from chlorophyll. There is further evidence in the prior art that molecular topology within chrolophyll can serve to slow down the rate of decoherence either by making chlorophyll more readily subject to recoherence via the antenna protein or chlorophyll itself, or in itself. It seems probable that both the structure of chlorophyll makes it more easily subject to recoherence and the antenna protein mediates this "recoherence," perhaps by photons absorbed in the center of chlorophyll's absorption band(s).

Beyond chlorophyll, quantum events in biology are evidenced by quantum coherent electron transfer demonstrated in quantum chemistry calculations, and it appears to play a role in cells in that, as the distance between two proteins increases, electrical conductivity falls off, but shows a plateau in electrical conductivity at a distance of about 12 angstroms to 15 angstroms. Conductivity falls off as distance increases. 12-15 angstroms is just the distance that allows a water molecule to hydrogen bond between two proteins and afford two pathways of electron transfer, hence in analogy with the two slit experiment, allows quantum interference patterns. The work on electron transfer by D. Salahub and colleagues at the University of Calgary, has shown such a bound water molecule and coherent electron transfer between two proteins. The cell is a densely crowded matrix of proteins at about the 10-15 angstrom distance, with an abundance of coordinated water between them. This invites the hypothesis that percolating connected pathways of electron transfer within and between the proteins in the cell cytoplasmic matrix occurs. This may allow extensive quantum coherent behavior in cells. Similar evidence in bird navigation by quantum behavior in molecules of their eyes picking up earth's magnetic field. More generally quantum biology is exploding, BUT IT REMAINS FOCUSED ON QUANTUM COHERENT BEHAVIORS. We believe quantum coherent behaviors are the literal tip of the iceberg in quantum biology, with many or most quantum effects in the Poised Realm of open quantum systems in an environment to which they can lose phase information, where quantum coherence is a limiting boundary of the Poised Realm. This bears on drug discovery and action, and molecular behaviors in cells and tissues and organs and the whole organism.

The electrons in such electron transfer within and between proteins with, or without such a percolating web, exchange electrons all the time. This implies that such electrons may induce recoherence, the Quantum Zeno Effect, and Quantum anti-Zeno effect on otherwise decohering quantum degrees of freedom in cells. Thus, cells may, to a substantial extent, live in the Poised Realm. In addition, drugs near or at the critical locus in the Poised Realm will participate in the slow, power law decoherence at criticality, rather than the ever faster exponential deocherence further from criticality toward order or chaos. All this concerning position on the X axis at least, will affect drug behavior in general and in vivo in particular. We believe this is of extraordinary importance.

But criticality in the poised realm has universal behavior associated with power law decoherence, not exponential decoherence. If slow decoherence is useful biologically, then critical location in the poised realm is useful. As noted above, a comparison of random organic molecules and evolved organic molecules tests whether evolved organic molecules are in a special, perhaps critical, location in the Poised Realm. Whatever the answer may be, it is a huge clue to effective drug design and action.

Molecules can behave in various reactions differently depending on where they are on the chaos-order (x) and quantum-classical (y) axes. Their position is an important characteristic which can be used in chemical and drug design. The position of a molecule on the x axis can be determined from the energy level spacing distribution as it was described for general systems before. Experimentally, the levels can be reconstructed from the excitation spectrum as it is known to the art, their mean level spacing $\Delta(E)$ as a function of energy can be fitted and then the distribution of spacings $s_n = (E_{n+1} - E_n)/\Delta(E_n)$ can be analyzed.

$$x = \frac{A - A_p}{A_w - A_p}$$

can serve as the x-coordinate where the quantity A is calculated from the actual level spacing of the system $$A = \int_2^\infty p(s).$$

The position on the y axis can be calculated from the Hamiltonian operator of the molecular system and its interaction matrix elements with the environment as we described earlier. In reality, from the point of view of molecular design the most important property is not the y coordinate position directly, but the distance of the molecular system from the critical poised realm state. This distance can be determined from the results of the decoherence measurements, e.g. form the output of the relevant echo type measurement. In molecular systems this is usually photon echo or neutron spin echo measurement. The result of the echo measurement is a signal $S(T_E)$ where $T_E$ is the echo time (time between the first and the second pulse as known to the art). For non-critical systems the long time behavior of the signal is exponential $S(T_E) \sim \exp(-T_E/T_D)$ where $T_D$ is the dephasing time, which serves as our coherence time FAPP. For critical PR molecular systems the decay of the signal is a power law $S(T_E) \sim T_E^{-\alpha}$ with some exponent $\alpha$, which can be determined from fitting the experimental curve. Systems in general are usually not exactly in their critical state, therefore the ultimate decay of the signal is exponential. However, depending on their closeness to the critical state a transitional form $S(T_E) \sim \exp(-T_E/T_D)/T_E^\alpha$ can be fitted to the curve and the parameters $T_D$ and $\alpha$ can be determined. In case of changing the parameters of the molecular system via changing the macroscopic parameters, applying external forces (for example laser light) transition towards the critical poised realm state can happen. Change towards the critical state is reached in a diminishing of the dephasing time $T_D \rightarrow 0$ determined via fitting the transitional form to the experimental echo signal. The value of $\alpha$ can change during the parameter change but it remains finite during the process. The measured value of $T_D$ is a good measure of the distance from the critical state. The smaller the $T_D$ the closer the system to criticality is.

Beyond simple parameter change the position of the molecular system can be changed by making changes is its configuration. Adding or removing some parts of a macromolecule or changing its structure by any manipulation can change its position within the poised realm.

As discussed above, degree of order (i.e., position on the x-axis of the poised realm model) can affect the decoherence rate of a quantum degree of freedom. For example, at the critical transition point of the degree of order (discussed above), the decoherence rate is suppressed. While not being bound by any particular theory, it is proposed that biological systems, and hence biological activity, operate optimally at particular rates of decoherence. In some embodiments, certain biological systems operate optimally where the decoherence rate is slow. In other embodiments, certain biological systems operate optimally at faster decoherence rates. Accordingly, for a particular biological system (e.g., a particular enzyme or receptor), the best drug molecules will be those having a particular degree of order (i.e., position on the x-axis).

Figure 4:
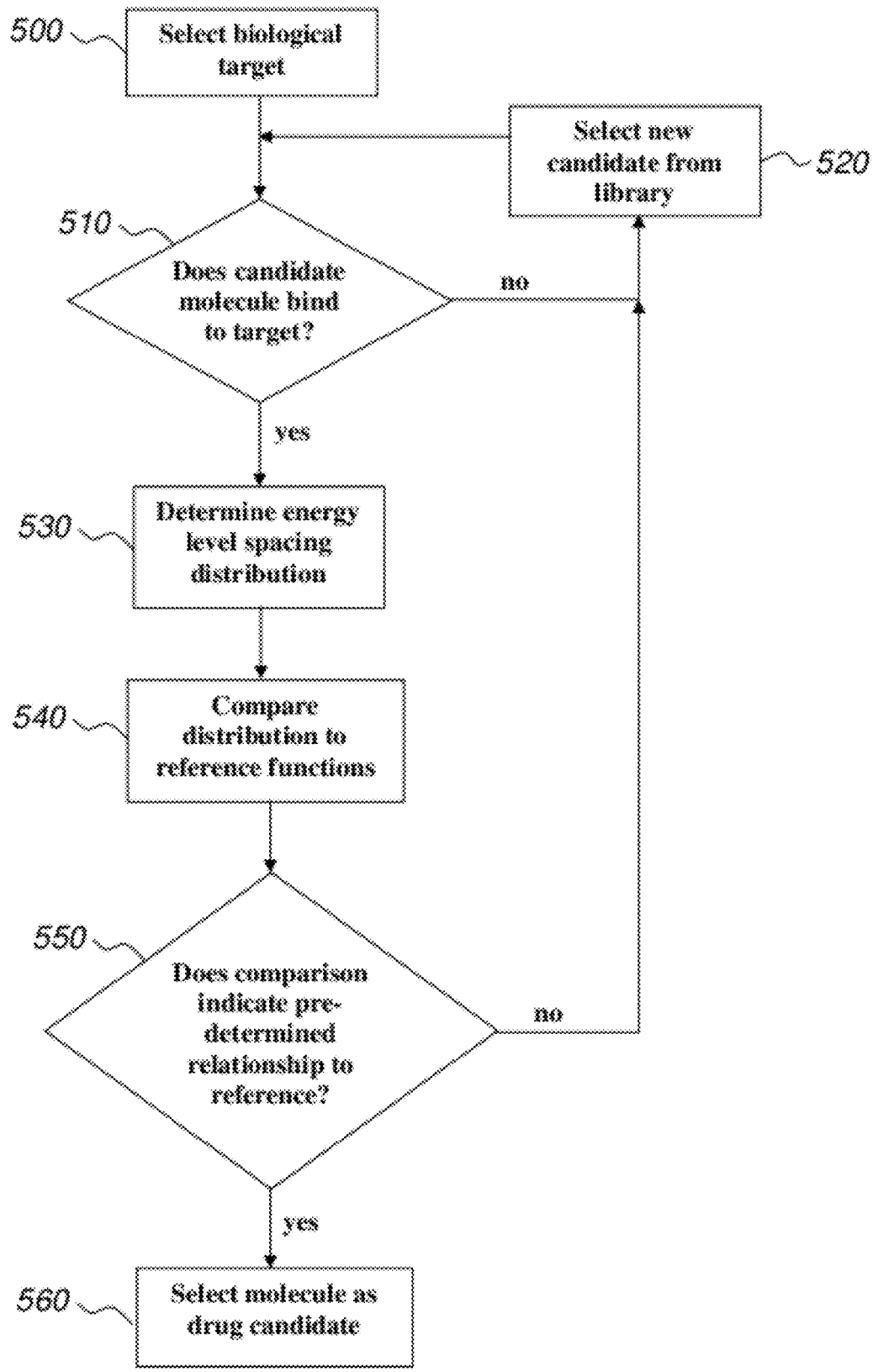
FIG. 4 is a flowchart illustrating a drug discovery method.

Some embodiments provide a method of drug discovery that seeks to identify drug molecules that particular targets based on the molecules' position on the axis. One such embodiment is described with reference to the flowchart of FIG. 4. This method seeks to identify the most promising drug leads for a particular target from a library of compounds. Identification of drug leads from libraries of compounds is a common approach to drug discovery; however, such approaches rely on either molecular modeling methods (e.g., ligand docking) or in vitro assays. Most compounds identified as promising by such methods often prove to be ineffective and/or toxic and are ultimately never developed into a drug. The present method provides an alternative approach.

Libraries of compounds to be used with the present method may be obtained using known means, for example, generated using combinatorial chemistry approaches or commercially available. At block 500 of FIG. 4, a particular biological target (e.g., an enzyme or receptor) is selected. At block 510, a molecule from the library is tested for binding to the target. Traditional methods of binding detection may be used, including in vitro binding assays and in silico modeling methods. If the test molecule binds to the target, it proceeds to the next step. If not, a new molecule from the library is selected at block 520 and is tested for binding.

At block 530, the energy level spacing distribution of a quantum degree of freedom in the molecule is determined. This distribution may be determined using known methods including experimentally (e.g., using spectroscopic techniques) or theoretically using known modeling algorithms. In some embodiments, the determination of energy level spacing is determined as it would be in the biological environment (e.g., while the molecule is bound to the target). Once the energy level spacing distribution is known, it may be compared to reference functions at block 540 to determine the degree of order (i.e., position on the x-axis) of the molecule. For example, as described above, in a pure ordered regime, the energy level spacing distribution has the form:

$$p(s) = \exp(-s)$$

where s is the energy level spacing and p(s) is the energy level spacing distribution. In a purely chaotic system, the distribution has the form:

$$p(s) = \frac{\pi s}{2} \exp(-\pi s^2/4)$$

The actual distribution of the test molecule may be compared with these functions to determine its position on the x-axis, for example, using $$x = \frac{A - A_p}{A_w - A_p}$$

where $$A_p = \int_2^\infty p_p(s), \ A_w = \int_2^\infty p_w(s), \text{ and } A = \int_2^\infty p(s),$$

where $p_p(s) = \exp(-s)$ and $$p_w(s) = \frac{\pi s}{2} \exp(-\pi s^2/4).$$

p(s) is the actual distribution for the test molecule.

At block 550, it is determined if the energy level spacing distribution of the test molecule has the desired relationship to the reference function. This relationship may be a pre-determined value for x found to correlate with high activity or in some embodiments, is the relationship that indicates that the molecule exists at the critical transition point along the x-axis. As discussed above, this critical point may be determined by the energy level spacing distribution having the form:

$$p(s) = 4s \exp(-2s).$$

Thus, in some embodiments, molecules are selected at block 550 that are close the critical transition point as determined based on their energy level spacing distribution.

If a candidate molecule has the desired relationship as determined at block 550, it is selected as a drug candidate at block 560. If it does not, the procedure returns to block 520 for the selection of a new candidate from the library. Drug candidates selected at 560 may themselves be suitable for drug development or, alternatively, may serve as lead compounds for further optimization using known quantitative structure active relationship (QSAR) medicinal chemistry. In some embodiments, new candidates based on the selected lead compound are also screened following the method in FIG. 4 to determine if they have the desired degree of order and are thus suitable drug candidates.

Figure 5:
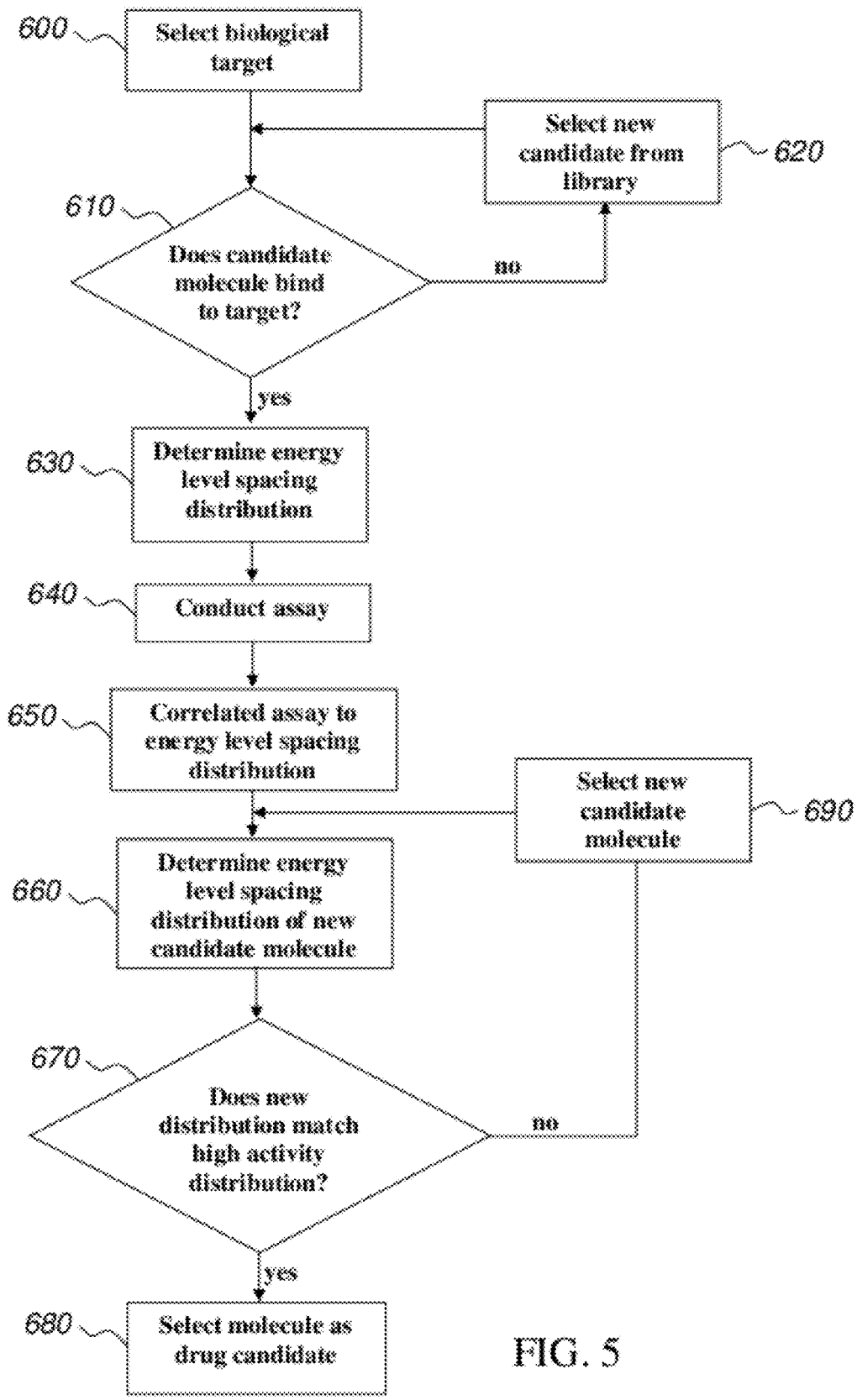
FIG. 5 is a flowchart illustrating another drug discovery method.

A variation of this method is described in the flow chart of FIG. 5. Again, a library of compounds is provided and biological target is selected at block 600. The candidate molecules are checked for binding to the target at block 610. If binding is not observed or predicted, a new candidate is selected at block 620. If binding is observed or predicted, the energy level spacing distribution is determined at block 630. Next, an in vitro and in vivo biological assay is performed to determine the activity level of the compound at block 640. This procedure may be repeated for a number of molecules in the library such that a correlation may be made at block 650 between the energy level spacing distribution and biological activity for the particular biological target. The correlation may be between a determination of a particular degree of order (e.g., position on the x-axis) or may be a particular energy level distribution obtained, for example, by averaging the distributions of the most active compounds.

Once a suitable correlation is constructed, a new candidate molecule may be tested without having to perform an experimental assay for biological activity. In this case, the energy level spacing distribution of the new candidate may be determined at block 660 using known methods. This distribution is compared at block 670 to the correlation determined at block 650. The comparison may include directly fitting the distribution to average distribution for previously determined active compounds or may include determining the degree of order (e.g., position on the x-axis) as described above and comparing that determination to the known active compounds. If a close match is made, that molecule may be advanced as a drug candidate at block 680. If not, a new candidate molecule may be selected at block 690 and evaluated in a similar fashion.

In some embodiments, the rate of decoherence of candidate molecules may be directly measured using known methods including spin echo techniques such as nuclear magnetic resonance spin echo, neutron spin echo, or photon echo. These techniques can be particularly useful to evaluate molecules within a biological environment (e.g., bound to a target in part a biological mixture, for example, a cellular extract mixture). In these embodiments, the above methods may be modified such that rather than determining and comparing energy level spacing distributions, candidate molecules may be tested for a desired rate of decoherence rate. For example, in one embodiment, candidate molecules that bind to specified target may be evaluated to identify the molecule having the slowest rate of decoherence. In one embodiment, the experimentally measured decoherence rate is fitted to the functional form $S(T_H) \sim \exp(-T_H/T_D)/T_H^\alpha$ and the value of $T_D$ determined. In one embodiment, selection of a drug candidate includes selecting molecules having low $T_D$ values.

Figure 6:
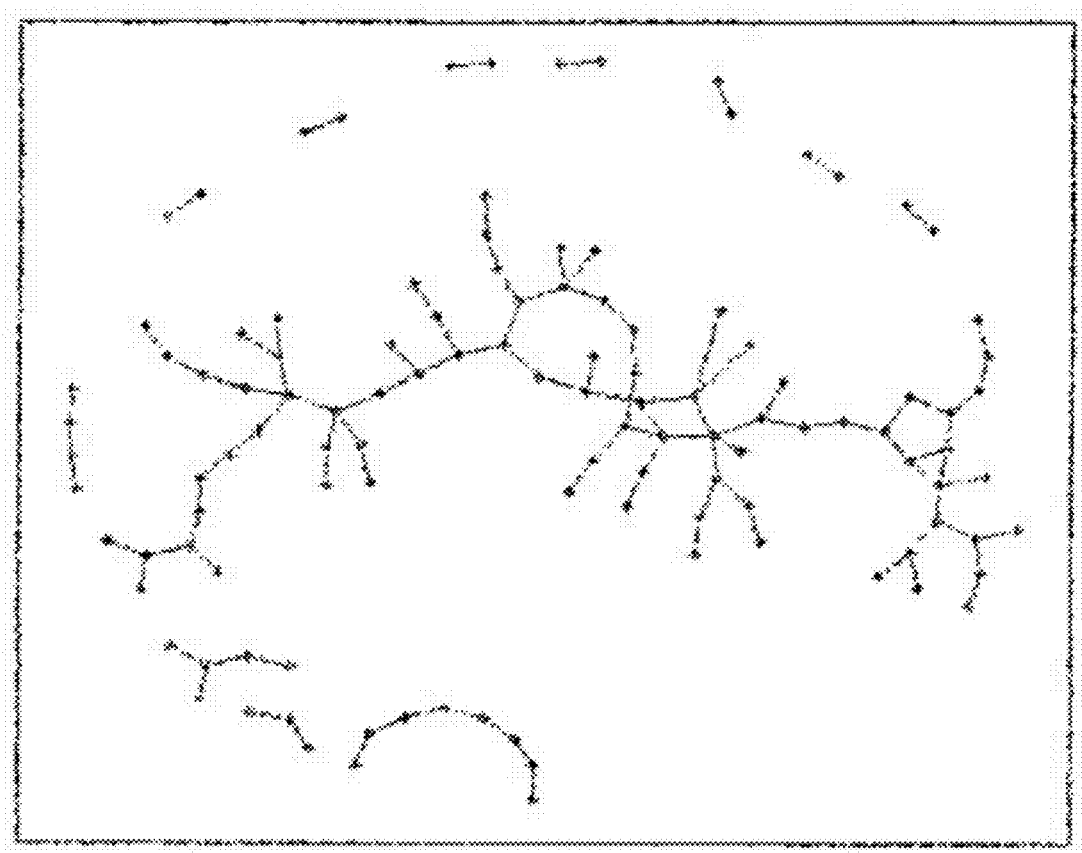
FIG. 6 is a graph depicting the Giant Component of a 100 node Erdos-Renyi Critical Random Graph.
Figure 7:
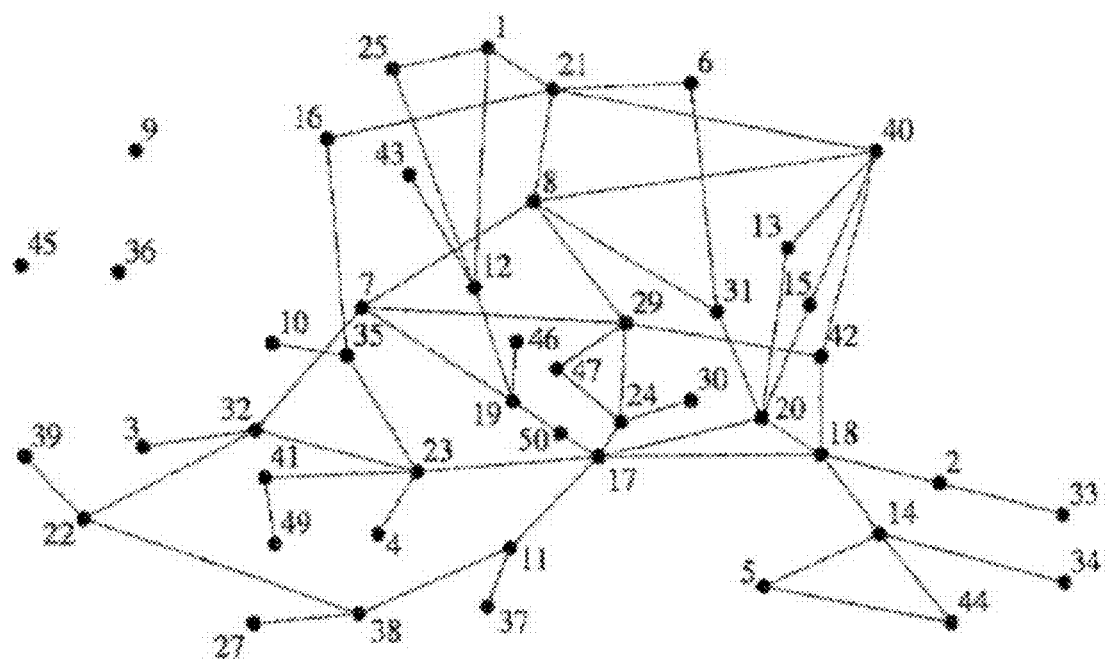
FIG. 7 is a graph depicting the Giant Component of a 50 node Erdos-Renyi Critical Random Graph.

Another embodiment considers the modeling of molecules using quantum networks. We use as a NON LIMITING example of quantum networks, taken as models representing real organic molecules, and as crude examples, the Erdos Renyi random graphs described above. FIG. 6 depicts an example of a 100 node exactly critical Erdos-Renyi graph, and typical Giant Component containing 83 of the 100 nodes. A critical ER Giant Component of 47 of 50 total nodes is shown in FIG. 7. The 83 node Giant component has 28 nodes with <k>=1 connections, 11 nodes with <k>=2 connections to their two neighbors, 14 nodes with <k>=3 connections to three neighboring nodes and five <k>=4 nodes connected to four neighbors. The ratio of bonds, or lines to nodes, i.e., bonds/nodes=1.349. The 50 node ER graph with a critical 47 node Giant Component has eleven <k>=1 nodes, eleven <k>=2 nodes, six <k>=3 nodes, six 6 <k>=4 nodes, and seven <k>=5 nodes. Its mean <k> is 2.34. The mean of these two is <k>=1.8445. We do not know the mean and variance of connectivities for critical Giant Components of Erdos-Renyi graphs, but presume that these two are roughly typical, probably on the low and high side of the mean <k> for such critical Giant Components.

Preliminary analysis suggests that biological small molecules, and perhaps proteins and nucleic acids and lipids, are very similar in their mean <k> values to the Giant Component of critical Erdos Renyi graphs. In contrast, many organic molecules not found in life seem to have a higher <k>, characteristic of the supracritical, or chaotic quantum graph regime. This analysis treats single, double and triple covalent bonds the same and counts only connections among pairs of atoms.

A small sample of non-biological organic molecules include the following: Napthalene <k>=2.2; Anthracene <k>=2.214; Methylpropane <k>=4.0; DiMethylpropane <k>=4.0; Cyclohexane <k>=4.0; Annulene <k>=2.0; Buckminsterfullerene <k>=3.0; and Diamond, <k>=4.0.

Over a random sample of 20 biological small to medium sized organic molecules, the mean value of <k>=1.928. While the sample of ER giant components is only two and we do not know the true mean of all possible ER giant components, their average, 1.8445, is close to that for the biological organic molecule sample (<k>=1.928). The spread in <k> values among the 20 biological organic molecules is very narrow. The 20 molecules and their <k> values are: acetate 1.66, caffine 1.96, abscisic acid 1.88, acetic acid 2.0, acetylcholine 1.555, adrenaline 2.0, alanine 1.875, arginine 1.925, asparagine 1.72, bacteriopheophytin A 1.983, B carotine 1.987, catechol 2.0, estrone 2.09, fructose-6-phosphate 2.0, glucose 1.965, histadine 2.04, isoleucine 1.92, lactose 2.0, phenylalanine 2.0, retinoid acid 2.0.

As noted, we do not yet know the mean and variance for the connectivity of the giant component among all critical Erdos-Renyi graphs. Presumably the true mean is near the mean of our two critical Erdos Renyi Giant components, <k>=1.8445. The narrow spread of biological organic molecules is striking, as is the close agreement between the two means, Erdos Renyi critical Giant components, and these biological small molecules.

Proteins and nucleic acids and lipids and polysaccharides seem likely to be close to critical in their covalent bond structure, again ignoring the distinction between single, double and triple bonds in favor of "connections between atoms." They are comprised of smaller components that are near critical.

These observations suggest that natural selection has tuned the position of biological molecules on the x-axis to be very close to criticality, with a very narrow range of <k> values, and we suggest below why this may be deeply useful in drug design and discovery. In turn, these observations suggest that cells live, due to natural selection, partially poised in the Poised Realm between fully quantum and fully classical and, like chlorophyll, natural selection has made good use of the Poised Realm.

We note that in a preferred embodiment of this invention, we can experimentally test whether random and evolved organic molecules are located, respectively through larger regions of the Poised Realm for random organic molecules, and whether evolved organic molecules are CRITICAL IN THE POISED REALM, by their rates of decoherence. Critical molecules will decohere in a power law distribution, as described above. Thus, using line band broadening as a measure of decoherence, spectroscopic means known in the art, or any other means now or in the future known to measure decoherence, we can measure an organic molecule to look for power law decoherence as a signature of the critical location and behavior of said organic molecule. Thus we can test, without limitation, any organic molecule for exponential decoherence if ordered or chaotic in the Poised Realm, or power law decoherence if critical in the Poised Realm. Without limitation, we can test if chlorophyll and its antenna protein are critical in the Poised Realm by testing for power law decoherence. Thus, in general, we can test whether evolved biological molecules are critical or near critical, while random organic molecules or other molecules are not critical in the Poised Realm. This is of general relevance to drug action and thus to drug design. Testing for power law decoherence or exponential deocherence may, without limitation, be made in vivo or in vitro.

A striking feature of our studies of the kicked quantum rotor using the LindBlad operator is that as kicking intensity and frequency increase, the rotor passes from the ordered regime with a large but finite number of quantum amplitudes with finite moduli, to fewer amplitudes with finite moduli as criticality is approached, to a sudden jump to classical behavior when the critical line in the Poised Realm is passed and chaos is entered on the x-axis. But when the system passes from quantum to classical behavior: i. energy is transferred from the quantum to the classical world. ii. The now classical degree of freedom can have CLASSICAL PHYSICS effects on the classical world! The poised realm system can then ACT on the classical world. iii. Position near the critical line maximizes passage back and forth from quantum to classical, thus the diversity of classical actions the system can take, based on Poised Realm "calculations" in the quantum aspect of the poised realm, which is non-determinate, non-algorithmic and not random! We use this in Trans-Turing systems below as well.

The quantum network models discussed above are not yet endowed with quantum degrees of freedom such as quantum rotors or oscillators at their nodes, with coupling between, e.g., quantum oscillators via springs along the arcs of the network. Ease of decoherence for quantum systems described by classical Hamiltonians, depends upon the average Lyapunov exponent, which is 0 in the ordered regime and bifurcates at criticality to a positive value, where decoherence occurs more readily. This invites the hypothesis, supported by our theorems above about power law decoherence for critical quantum systems, which we can test computationally, that critical quantum networks with, for example quantum oscillators at the nodes and coupled by springs, decohere less easily than do supracritical or ordered quantum networks with such coupled quantum oscillators. If the hypothesis is proved, we suspect that small evolved biological molecules, and hence also bioactive drugs, may live poised partially in the Poised Realm and be able to behave classically by increasing $<k>$ via, e.g., hydrogen bonds where they become both subject to rapid decoherence, and behave classically by crossing the critical line on the X axis into chaos and decohere rapidly. We recall the evidence that decoherence can alter the rate of a chemical reaction.

Based on the foregoing, there are two implications for drug discovery and drug action:

1) A drug, when quantum coherent cannot ACT classical. Thus, we can "turn off" a drug by inducing quantum behavior either by recoherence on the y-axis of the Poised Realm, or lowering $<k>$ values than about 1.8445 (i.e., moving on the x-axis of the Poised Realm toward criticality and power law slow decoherence rather than rapid exponential deochrence). And conversely, we can turn the drug "on" again by inducing decoherence as in the Quantum Anti-Zeno effect, or transition to chaos and classicity by increasing $<k>$ and moving $<k>$ to be greater than 1.8445, to supracritical quantum network molecular structures and dynamics in the chaotic regime on the x-axis of the Poised Realm. Here the molecule remains connected, ie $<k>$ equal or greater than 1.0, and at a position further out the X axis than criticality, decoheres exponentially rapidly to classicality FAPP or by measurement, hence becomes classical and can have classical effects on the classical world of the cell or organ.

2) We can design drugs which are critical on the x-axis. Indeed, drug molecules are open to a statistical study to see the mean and variance of their $<k>$ values. Improved drugs may be obtained by tuning $<k>$ to criticality for at least two reasons. First, if small molecules in cells are near the quantum classical boundary, due to natural selection, it is because their classical physics action requires crossing that boundary back and forth. Then drugs would seem likely to act more efficiently if they could participate in such action. Note that this is in strong contrast to designing drugs using classical molecular dynamic models of molecules with classical potential functions then docking the classical model molecules with classical ligands. This may be a rough approximation to a dance of quantum-classical transitions in the Poised Realm by small molecule effectors, natural or drugs, acting on larger, supracritical, more classical target ligands. In short, small molecules and drugs may perform best if poised in the Poised Realm between quantum and classical behavior, able to become classical by hydrogen or van der Waals forces to ligands, altering $<k>$ into the supracritical, chaotic, classical behavior regime. It follows that drugs can act by having $<k>$ values that are lower than critical ER giant component graphs, or more accurate than ER, chemical network structures we can use for drug design, and by ligation to a target, lower the total $<k>$ value moving target+adduct to lower X values, hence more quantum behaviors to inactivate the target+adduct molecule by altering from classical to quantum behaviors. This is in stark contrast to the standard view of a drug as a classical object binding to and blocking binding of a small molecule to a target molecule, e.g., blocking estrogen from binding to the estrogen receptor. Here, instead, estrogen may be made more "quantum" by binding a drug to estrogen itself, lowering its $<k>$ value, so it less readily becomes classical on binding the estrogen receptor, and hence is unable to act. Conversely, to increase the activity of estrogen, we might seek to increase its $<k>$ value by an adduct that increases estrogen+adduct mean $<k>$, so the total system becomes classical more readily by motion outward on the x-axis.

Thus, the Poised Realm affords a truly new way to think about blocking or activating biological drug target molecules, quite independently, or together with, binding to the "binding site" of the target considered as a classical molecule. Importantly, moving the target+adduct to a lower mean $<k>$ than critical, hence more rapid deochrence may be feasible by adducts that bind at MANY sites on the target, e.g., without loss of generality, estrogen molecule, IN ADDITION to also binding in the binding site of estrogen. Then the number of ways to "block" the action of estrogen, or by making estrogen+adduct more classical hence enhance estrogen's activity, are likely to be increased compared to classical considerations of blocking only the binding site of estrogen. Thus many more candidate drugs per target become possible.

In further consideration of the above, an adduct binding not necessarily at, but also near the binding site of a larger molecule, such as the estrogen receptor as a nonlimiting example, may alter the local quantum Poised Realm behavior of that part of the receptor, rendering it more quantum, hence blocking the receptor from binding, or becoming more classical hence rendering it more able to bind. Again the number of drugs that may bind near the binding site and accomplish this adds to those that classically bind the binding site, and so increase the number of potential drugs affecting estrogen-estrogen receptor interactions.

With respect to turning a drug on or off, some embodiments include stopping and starting the activities of roughly critical small molecules in the cell by inducing recoherence via, without limitation, laser light in their absorption bands. Organic biological molecules often absorb in the infrared and very far infrared. Infrared radiation, about 1000-3000 nanometers, can penetrate substantially into the human body. Thus we can induce recoherence of small molecules in the body, using the information obtained from the specific absorption and emission spectrum of each small organic molecule, and hence directly "address" specific molecules in the body to affect the quantum or classical or Poised Realm behavior of that specific molecule in the body. Some embodiments use energy ranges that reach only the skin or a bit under it (e.g., using visible, infrared, or far infrared light). Other embodiments use light that penetrates more deeply (e.g., using longer wavelengths, with the obvious proviso that damage to tissues must not be done). Avoiding damage may be obtainable in general by modulating the timing and spectral distribution frequencies of the incident photons.

Similarly, given a drug that is, roughly, critical, some embodiments increase its "classical" action by inducing decoherence via the Anti-Zeno effect or generalizations, or decrease its effect by inducing recoherence by driving its quantum degrees of freedom with, without limitation, laser light in the infrared or longer wavelengths, where the drug has absorption bands, or for topical skin treatment or other topical treatments, with light in the visible.

The above use of recoherence and decoherence to tune a drug's position in the Poised Realm can be used to obtain optimal drug action by controlling behavior in the Poised Realm.

Thus, small molecules and drugs may act best, not classically, but by being poised in the Poised Realm where a smooth transition to classicity is achieved upon binding adducts to move the drug further toward order and quantum Poised Realm behavior. This may allow the drug to gradually anneal to a classical or near classical Poised Realm state in binding to the larger protein or other drug target. We can tune this annealing by tuning where the drug is on the x-axis and by infrared radiation to tune decoherence and recoherence.

Furthermore, like real annealing where a metal is heated, hammered, then quenched repeatedly so that it finds microcrystal rearrangements to ever deeper potential wells and becomes and ever harder metal, and in analogy to simulated annealing in a finite time using both "cooling" and "heating" to tune the free energy surface to avoid poor local minima on a classical potential, we can "anneal" repeatedly our drug to its small, perhaps critical, or larger more supracritical target. In particular, upon binding to a supracritical target ligand, a small critical drug, will, through hydrogen bonds, become on average more supracritical, hence classical, and "freeze" into a more rigid behavior, but in decohering make use of the Poised Realm quantum behaviors which can explore quantum possibilities and find good potential wells. By repeatedly inducing coherence with infrared radiation, then allowing decoherence multiple times, a better ultimate binding of drug to target may be obtainable.

Finally, if drug and target are both roughly critical where decoherence is power law slow and not exponential fast in the ordered and chaotic regimes, and partially in the Poised Realm, we can use infrared to longer wavelengths radiation, as noted above, to help prevent decoherence and sustain the Poised Realm behavior not sustainable by photon showers from within the cell.

Determining Coherence and Order of Candidate Drug Molecules.

As discussed above, degree of order can be determined by the absorption/emission spectrum of a drug or organic molecule via the level spacing distribution. The degree of coherence can also be determined by absorption band widening due to decoherence. If critical quantum molecules decohere less easily than supracritical ones like polycyclic hydrocarbons, the critical molecules and presumably small biologically active organic molecules with <k> near 1.8445, or more realistic chemical structures, should show less band broadening than polycyclic hydrocarbons or Buckmeisterfulerenes with <k>=3. More, Buckminsterfullerene or other X axis chaotic molecules may decohere exponentially and more rapidly exponentially as they are more chaotic, so exhibit a Quantum Anti-Zeno effect more readily than critical organic molecules. So too may polycyclic hydrocarbons compared to more critical organic molecules subjected to natural selection.

Finally, we can assess criticality, subcriticality or supracriticality on the x-axis for the molecular structure of a drug, adduct, target, and drug+target or drug+adduct+target, via the eigen value spectrum of its adjacency matrix for its energy levels, from which one can deduce the absorption and emission spectrum of the above drug, drug+target, or drug+target+adduct. These predictions can then be tested experimentally by measuring absorption bands by any means known in the art.

It will be clear to those of ordinary skill in the art that it is possible to test any molecule, or set of molecules in an assemblage for their position both on the X axis alone and in the poised realm generally. Here we use three independent approaches, alone or together. First, we use a quantum network model to determine position of any molecule on the X axis, hence also any set of independent molecules. Second, we measure the absorption and or emission spectrum distribution to establish, as noted elsewhere in this patent application, the position of the molecule or molecules, on the X axis. Third, we measure the decoherence rate, ranging from a power law for a critical position on the X axis to an exponential whose rate can vary on the X axis, and to intermediate decay forms that are mixtures of power law and exponential behaviors as described in this patent application.

It will be clear to those of ordinary skill in the art, that if the molecule being studied or set of molecules being studied are behaving in a classical fashion, they can be stimulated by any means known in the art, including appropriately tuned laser wavelengths, as described in this patent application, to behave in the Poised Realm, or quantum coherent behavior may be obtained in the limit of total recoherence or reflowering of quantum amplitudes. It may often be necessary to stimulate such Poised Realm behavior to assess experimentally by absorption/emission spectral distributions and decoherence rates, the position of the molecule or a set of molecules on the X axis.

However, in general, organic molecules are quantum in their behavior as is well known in the art to spectroscopists, hence no stimulation as in the above paragraph will typically be needed.

In general, if the absorption/emission spectra of the different molecules are all uniquely different the set of molecules can be measured for their position on the X axis simultaneously by measuring the spectra of each molecule and the total set of molecules.

More generally, for assemblies of molecules, the absorption/emission spectra may reflect inter-atomic or inter-molecular interactions, but both the absorption/emission spectrum of the assembly, and its decoherence rate can still be measured to asses the position of the assembly as a whole on the X axis. Here if there is a distribution of positions on the X axis by different parts of the assemblage, this will show up as different absorption/emission spectral distributions by the different components of the assembly. These can be deconvoluted, trivially if the spectral lines for each molecule are unique, and those due to inter-atomic and inter-molecular interactions are unique for any pairs of molecules or small interacting subsets of molecules in the assembly. More complex spectral distributions can also be deconvolved because we know the ratios of the different molecules and their binding partners in the assembly, without limitation, a macromolecular assembly such as a neurotransmitter receptor and its complex of molecules in a synapse.

With the above, we can study drugs that are known to be effective, and/or evolved biomolecules, compared to random and in particular unevolved organic molecules to test the locations of in vitro or in vivo drugs or evolved organic molecules on the X axis and in the Poised Realm, compared to "random" organic molecules. In one non-limiting experiment, unevolved organic molecules from chrodronaceous meteorities, such as the famous Murchison meteorite, which has been shown to have at least 14,000 distinct organic molecules, are used to test differences in the poised realm between evolved and unevolved molecules. Since the meteorite dates from about the origin of the planet earth, these molecules are clearly abiotic. In addition, collections of known natural abiotic and synthesized organic molecules are widespread, including in Beilstein, and in the libraries of pharmaceutical companies, including, without limitation, combinatorial chemistry libraries. In addition, we incorporate by reference Origins of Order by Stuart Kauffman, Oxford University Press, which describes a means to generate large libraries of organic molecules titled "random chemistry" which can be used to obtain unevolved organic molecules.

In one experiment, approximately 1500 FDA approved drugs available from the Johns Hopkins Chemical Compound library is used to determine how they cluster in the poised realm. Specifically, the position on the x-axis of the poised realm is determine using methods described herein for each of the 1500 approved drugs. These are in turn compared to a random library of compounds, such as those available from compound databases (e.g., Beilstein) or from the Murchison meteorite. The experiment can demonstrate whether molecules having drug action cluster around a specific value on the x-axis. For example, they may cluster around the critical point discussed above.

Quantum Reservoir Computer

One embodiment utilizing a system operating in the poised realm is quantum reservoir computer, which is an embodied quantum variation of a classical reservoir computer known in the art. In this embodiment, the nodes within the reservoir are physical entities having at least one quantum degree of freedom that is capable of coupling (e.g., via superposition of states) to quantum degrees of freedom in other nodes in the reservoir. Unlike current quantum computers that utilize qubits, a quantum reservoir computer does not require that all elements (i.e., nodes) in the reservoir be fully quantum coherent. Rather, the quantum parallelism in the system is exploited in a self-organizing manner. Thus, the system can, in some embodiments, operate at room temperature.

The reservoir of the quantum reservoir computer can be viewed as a collection of weakly interacting discrete quantum degrees of freedom. The reservoir may comprise any fixed number of physical entities (referred to herein as "nodes") having at least one quantum degree of freedom. In one embodiment, the nodes are chromophores, which may including a biological chromophore such as a photosynthetic unit (e.g., chlorophyll, with or without it's accompanying antenna proteins), a non-biological organic chromophore (e.g., highly conjugated organic compounds), or an inorganic chromophore such as an inorganic metal complex. In one embodiment, chromophores are selected having a relatively long, but finite, coherence lifetime (e.g., as is found in chlorophyll).

In another embodiment, the nodes in the reservoir are spins or magnetic moments. Any known spin or magnetic systems may be used, including for example paramagnetic or ferromagnetic compounds or nanostructures. In one embodiment, an artificial spin system such as is the commercially available in the D-WAVE system may be used, which utilizes superconducting current to simulate spins.

In some embodiments, the quantum reservoir can be tuned to achieve a desired coherence time. For example, decoherence may be added by applying a random noise potential. The system may be tuned into the desired Poised-realm state by adjusting this potential. This way, a quantum reservoir is realized that is not fully coherent, but has a very long coherence time. Repeated measurements of this system reset its quantum coherence, which decays very slowly. Thus, this system can be kept coherent for a sufficiently long time, so that superposition states stay alive for the time intervals of single calculation steps.

The quantum degrees of freedom utilized in the reservoir may be any degree of freedom that may be coupled between the nodes as well as coupled to an input and output signal. Non-limiting examples of quantum degrees of freedom include electronic excitation states, quantum spin (e.g., electron spin and nuclear spin), quantum angular momentum, and quantum linear momentum.

Figure 8:
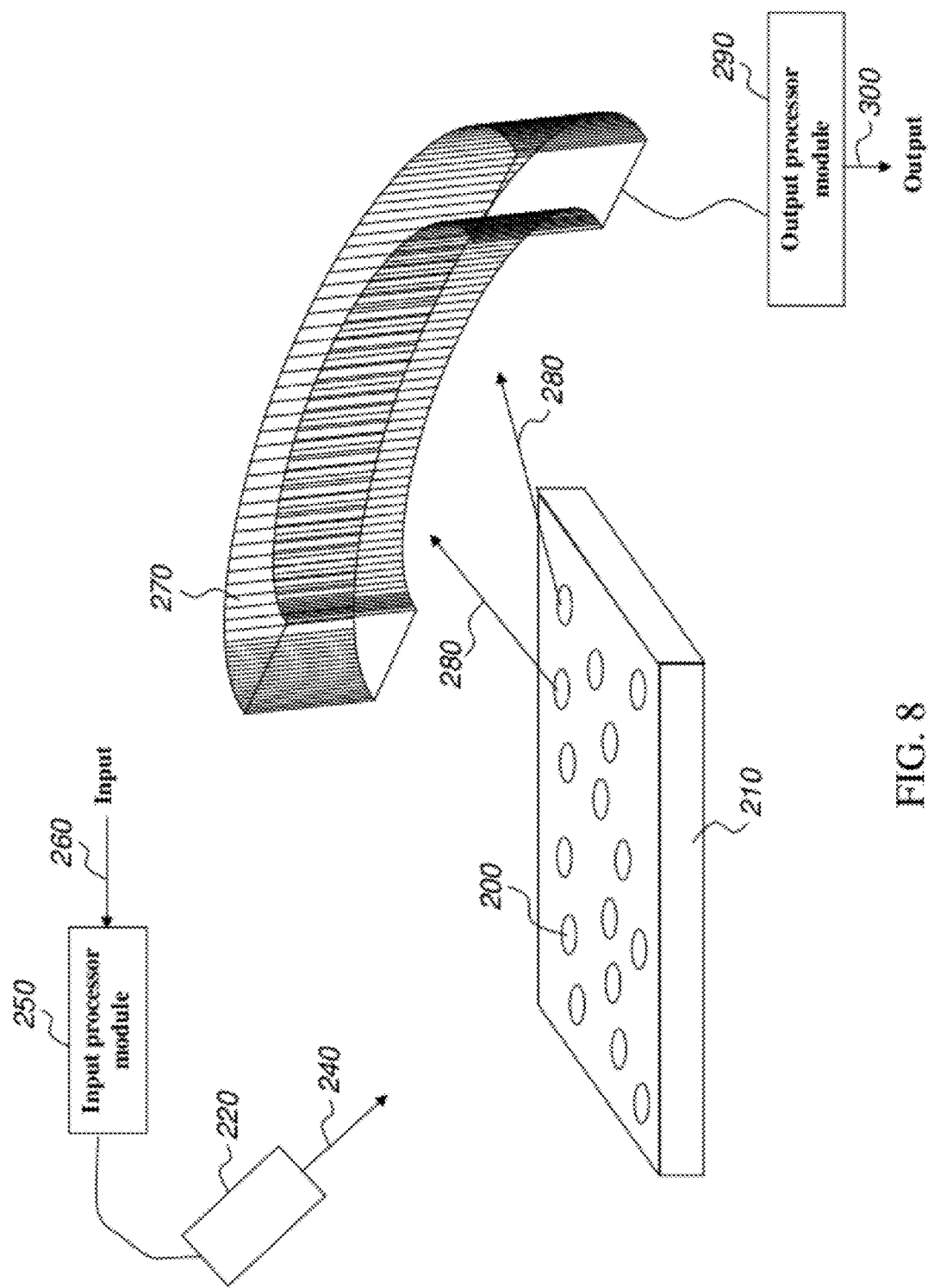
FIG. 8 is a block diagram of a computer utilizing quantum nodes and time-varying inputs and outputs.

With reference to FIG. 8, a plurality of nodes 200 are contained within or on a substrate 210. In some embodiments, the nodes 200 are fixed in or on the substrate. For example, a glass, silicon, or mica wafer may be used as a substrate 210 and the nodes 200 are adsorbed or deposited onto the surface of the substrate 210. In other embodiments, the nodes 200 are free to move within the substrate 210. For example, in some embodiments, the substrate 210 may include a liquid medium within which the nodes 200 are dispersed or dissolved. In some embodiments, the nodes 200 are distributed in a regular array (such as by using established microfabrication techniques). In other embodiments, the nodes 200 are randomly distributed.

In one non-limiting example, the nodes 200 are photosynthetic units that are deposited on a mica substrate using adsorption from solution. One such technique is described in Scheuring et al., *The EMBO Journal* (2004) 23:4127-4133, which is incorporated herein by reference in its entirety. In this technique, cell membranes containing photosynthetic units from *Rhodospirillum photometricum* are dissolved into dodecylmaltoside solution. The resulting extract is placed on freshly cleaved mica using an adsorption buffer drop. The resulting structure includes a plurality of photosynthetic units distributed across the surface of the mica.

The quantum reservoir described above may be used to build a non-algorithmic computational architecture based on the principles of neural networks, such as echo state networks or liquid state machines. The general idea is (i) to drive a random, large, fixed quantum recurrent neural network with an input signal, thereby inducing in each node within the reservoir to produce a nonlinear response signal, and (ii) produce a desired output signal by a trainable linear combination of all of these response signals.

In some embodiments, the input signals comprise a quantum driving force that couple to one or more quantum degrees of freedom of the nodes 200. Non-limiting examples of suitable input signals include photons, electrons, and electrical or magnetic fields. In one embodiment, the input signal is supplied to all nodes 200. For example, with reference to FIG. 8, a laser 220 may send laser pulses 240 of appropriate frequency to couple to a quantum degree of freedom in the nodes 200.

To translate a real-world classical input to the quantum mechanical input signal 240, an input processor module 250 may be provided. This module comprises a traditional algorithmic computer, such as a general purpose computer, that receives a classical input signal 260 and drives the input signal generator (e.g., laser 220) based on the classical input signal 260. For example, a time-varying analog electrical signal may be provided to the input processor module 250, which then translates that signal into appropriate time-varying driving of the signal generator 220. Thus, a time-varying classical input 260 results in a time-varying quantum input signal 240 being supplied to the nodes 200. For example, time-varying current or voltage may be provided to the input processor module 250, which then drives laser 220 to produce a corresponding time-varying change in pulse frequency, light frequency, or intensity of laser light 240 being supplied to the nodes 200.

In response to the quantum stimulation and the quantum coupling of the nodes 200 to each other, nodes 200 may radiate out a quantum response signal, such as scattered photons. Each node 200 can radiate an output signal and that signal may radiate in multiple directions. Some embodiments provide a detector 270 that detects the time-varying output signals 280. In the case of scattered photons, the output signals may be detected using photodetectors or a spectrometer. In some embodiments, the detector 270 includes an array of subdetectors in order to detect output signals 280 emitted in different directions. Other suitable detectors may include a nuclear magnetic resonance detector or an electron paramagnetic detector.

The result of the detection described above is a plurality of time-varying output signals. The multiplicity of the signals may be provided by detecting the time variation of a variety of parameters, such as the time variation of a plurality of frequencies of scattered photons or the time variation of photons scattered in a plurality of directions. The plurality of output signals may then be relayed to an output processor module 290. The output processor module 290 applies weights or other signal processing algorithms to the plurality of output signals to produce a single output signal 300. This module comprises a traditional algorithmic computer, such as a general purpose computer, that receives the plurality of output signals from the detector 270 and calculates the output signal 300.

Figure 9:
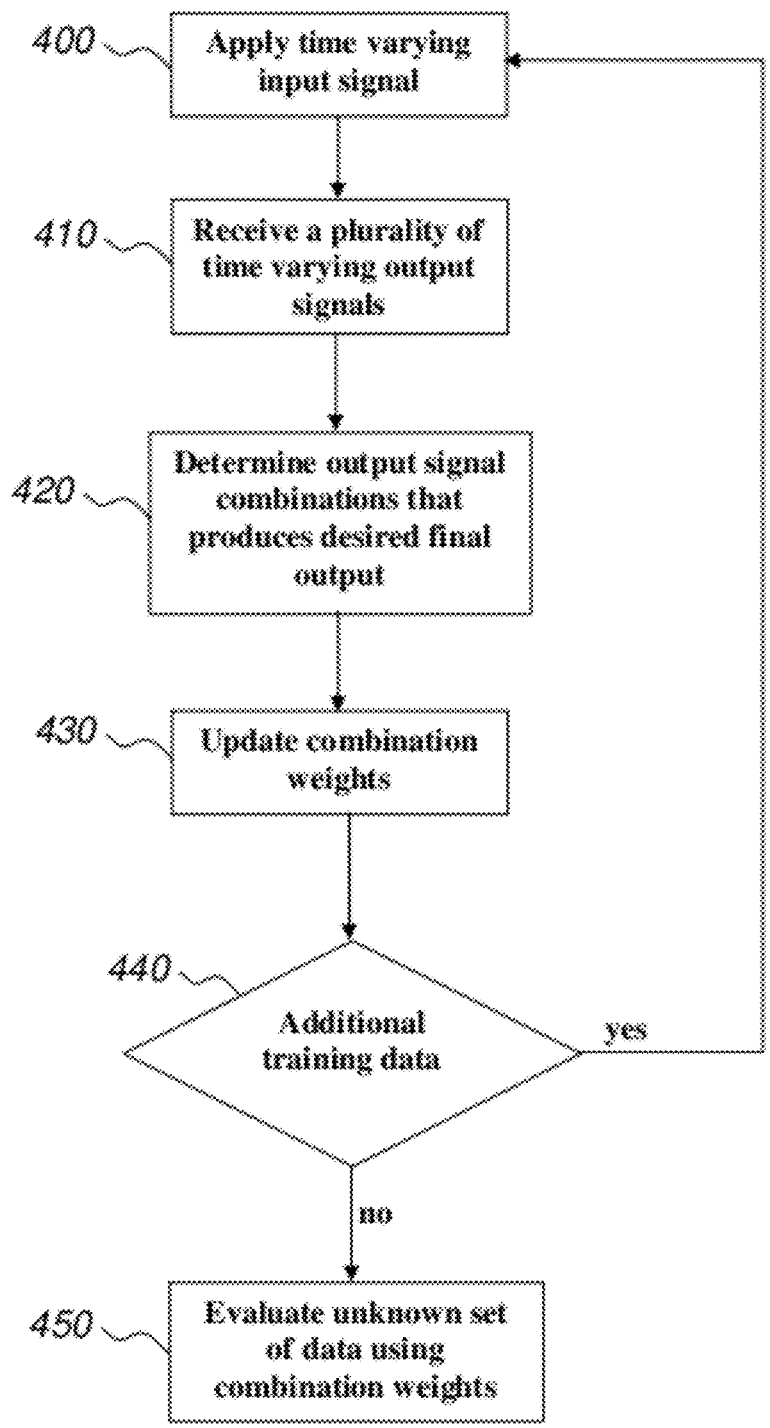
FIG. 9 is flowchart illustrating a training method for the computer described in FIG. 8.

The weights or other signal processing algorithm used to derive the output signal 300 from the plurality of outputs 280 produced by the nodes 200 may be determined using one or more training procedures, such as is known in classical reservoir computing. One example of such a training method is depicted by the flowchart in FIG. 9. At block 400, a time-varying input signal for which there is a known, desired output is provided to the quantum reservoir as discussed above. At block 410, a plurality of time-varying output signals is received by a detector as discussed above. These signals as well as the desired final output are sent to the output processor module. The output processor module determines a weighted combination or a set of weighted combinations of the plurality of output signals that will produce the desired final output. In one embodiment, the weighted combination of outputs is a linear combination. In other embodiments, more complicated functional forms are utilized. In some embodiments, the output processor module determines the optimal functional form. Once a suitable combination is determined that produces the desired output, the corresponding weights are stored in memory.

At block 440, it is determined whether there is any additional training data (i.e., another known input-output combination). If so, the procedure returns to block 400 for input of the additional data. When block 420 is reached, the appropriate combination weights are determined that produces the desired output that is also consistent with all previous training data. The new weights are updated into memory at block 440. If no more training data is supplied, the procedure proceeds to block 450, where a set of input data having no known output is supplied to the quantum reservoir. The stored combination weights are applied to the plurality of output signals in order to produce the final output.

In one non-limiting example, the above described quantum reservoir computer may be implemented using a simulated spin system, such as provided by D-WAVE. The commercially available D-WAVE computer contains a plurality of qubits consisting of superconducting currents that simulate spin. The inputs and outputs are electrical current. In its intended mode of operation, the D-WAVE computer operates using only fully quantum coherent qubits and non-time-varying input (i.e., a traditional quantum computer approach). However, in the present context, all simulated spins, including those that are not fully quantum coherent are used as nodes for the quantum reservoir. Furthermore, a time-varying input signal and plurality of output signals is provided. With a proper $J_{ij}$ and $h_i$ set, the D-Wave Hamiltonian:

$$Hp = \sum_{i=1}^{N} h_i \sigma_i^2 + \sum_{i,j} J_{i,j} \sigma_i^2 \sigma_j^2,$$

can be guided through a finite size version of the metal-insulator transition. At various low temperatures, the interplay of thermal decoherence and the spectrum can be determined to achieve the properties necessary for use as a quantum reservoir.

Trans-Turing Machine

In What Is Life, 1944, E. Schrodinger guessed that genes would be "solids" with quantum mechanical chemical bonds, and for our purposes now, guessed that the gene would not be a periodic crystal, for these were "dull" but would be an aperiodic crystal that contained a microcode for the organism. DNA is exactly such an aperiodic crystal. The microcode does not "describe" the generation of the organism or its maintenance, but accomplishes these by organized behaviors of matter and energy coordinated by the "information" in the aperiodic crystal, plus, as it turns out, the entire cell as an open far from equilibrium thermodynamic system.

The information is "embodied" and culminates in building and maintaining an organism.

The embodied sense of information in Schrodinger's statement may be contrasted with Shannon and Kolmogorov information. The former consists in the entropy of an ensemble of messages, in some finite alphabet, in a Source. The latter is the shortest program that will output a given sequence of symbols in a prestated alphabet. Both Shannon and Kolmogorov information measures tell us how much information we have, but not what information "is." All we have is syntax. Nor is there, by design, any "coming into being" of the information in question, nor any semantics of that information on Shannon or Kolmogorov. Thus, Shannon and Kolmogorov information is not embodied, is free of matter and energy, free of specific classical physics causal consequences that may be biologically functional in a cell or organism, and seems to float in the air, a third constituent of the universe with matter and energy.

In contrast, Schrodinger's sense of the aperiodic crystal containing a microcode for the organism has within it in an unarticulated way, the ideas of the processes engendered by the microcode, (plus the cell as an open thermodynamic system), hence the semantics of the code, that is, the specific processes, whether quantum, open quantum, poised realm, or classical specific causal consequences, it engenders. More, matter and energy are explicit in the processes engendered by the microcode. Information on a Schrodinger sense is embodied with matter and energy, not floating free as a third constituent of the universe.

The essential feature of the aperiodic crystal is broken symmetries, as in the DNA molecule with its essentially arbitrary sequence of bases, A, C, T, G along the aperiodic double helix.

Information in an aperiodic solid or any system combining quantum, classical and Poised Realm processes, is typically, but not always, embodied in the broken symmetries of the system. In particular, it is the broken symmetries of the Hamiltonian of the classical, poised realm and the quantum systems with its classical physics borne Hamiltonian which may have many broken symmetries, which embody information, classical, Poised Realm, and quantum matter and energy, with a semantics that is the processes that are enabled by the constraints contained in the Hamiltonians (or other constraints in the dynamics of the classical, Poised realm and quantum degrees of freedom). More these broken symmetries constitute constraints on the release of energy. But "work" is the very constrained release of energy into a few degrees of freedom, (Atkins). Thus classically, this constrained release of energy is work, not heat or entropy. This information has a fundamental semantics in engendering processes that carry out thermodynamical work. Such processes underlie any system capable of complex, diverse organized behavior built from a series of classical actions serving specific useful purposes, however defined. (We turn to candidate definitions of "useful purpose"="function"="task" below.) The information or code engendering such processes has an embodied meaning in this sense of purposeful (e.g. in terms of survival and reproductive success) systems performing classical actions, quantum and Poised Realm behaviors. A code has to endogenously engender these classical actions (e.g., DNA), by constraining the flow of matter and energy, to be embodied information. The reason we stress "classical behavior" is the fact that as quantum or Poised Realm quantum amplitudes propagate, nothing "real" happens in the "real classical world."

The philosopher Immanuel Kant defined an organized being as that in which the parts exist (in the universe) for and by means of the whole, and the whole exists for and by means of the parts. A simple example is a collectively autocatalytic set of peptides, a concept invented in 1971 by Kauffman ( ). Gonen Ashkenazi at Ben Gurion University in Beer Sheba Israel has a nine peptide (small protein) collectively autocatalytic set. No peptide in the set catalyzes its own formation. Rather, each peptide catalyzes the formation of one or more other peptides among the nine peptides from fragments of those peptides. The nine peptide set achieves autocatalytic "catalytic closure" because all the nine peptides have their formation from their fragments catalyzed by at least one of the nine peptides in the nine peptide set. Catalytic closure is precisely an example of Kant's Organized being. The parts exist (in the universe) for and by means of the whole nine peptide autocatalytic set, and the whole collectively autocatalytic set exists for and by means of the parts. Call such a Kantian system, "Autonomous". Given an autonomous system we can define the function of a part by the role it plays in sustaining the existence of the whole in the universe. Note that the explanatory arrows from upward from the parts to the whole, and downward from the whole to the parts whose behaviors the whole organises.

Given an autonomous system a natural sense of purpose=function=task is given by those quantum, poised realm, and/or classical consequences of the parts that sustain the whole in existence in the universe. Note that the function of the heart is to pump blood, not make heart sounds or wiggle water in the pericardial sac. Similarly, the function of one of the nine peptides is to catalyse the appropriate reaction, not wiggle water in the medium. The function of a part is a subset of its consequences, only definable as above. Given the concept of autonomy, we can see part of the reason Shannon and Kolmogorov information are inadequate if powerful. They are syntactic only, have no specific causal consequences associated with the bits in the bit string, thus CAN have no function in sustaining the autonomy of a system that gets to exist in the universe. We will use autonomy with Trans-Turing systems below as one means to solve the famous Frame problem of computer science.

Thus, ultimately for the information to have effects in the decoherent "real world", some variables of a quantum, Poised Realm, and/or classical system must ultimately become classical.

The complex Hamiltonians available in Poised Realm Systems, open to quantum, Poised Realm and classical inputs and acting on their worlds via quantum, Poised Realm and classical outputs, are constraints that can have many broken symmetries so contain a great amount of embodied information enabling a high diversity of quantum, poised and classical information processing and acting in the world of the system.

We show below that such a system is not a universal Turing Machine, nor a classical "machine," but much richer.

First we begin with a seminal paper by Dennis Salahub and coworkers, (JACS) that is a first major step toward Trans-Truing systems. de la Lande, JACS (2011) 133:3883-3894, incorporated herein by reference in its entirety. Salahub et al. considered a simple system of many nuclei and electrons in two potential wells, (FIG. 6 in Salahub). Here the X axis is a reaction coordinate. The Y axis is energy. Two potential wells, A and B lie in this plane, and overlap, the right hand ascending branch of the A well crosses the left hand ascending branch of the B well. The nuclei are at this crossing in the initial state, called the "seam region" and consist in a superposition of states, A and not A, B and not B. Nuclei are heavier than electrons, so, using a version of the Lindblat operator, the nuclei decohere to classicity rapidly and, essentially at the same time, fall either into well A or well B. They have passed from quantum superpositions to classical nuclei in one of two displaced potential wells. The immediate consequence is that the electron cloud responds DIFFERENTLY according to whether the nuclei have decohered to well A or to well B. Thus, as we claim in general for Trans-Turing Systems, as some quantum degrees of freedom decohere to classicity, (or are measured), that ALTERS the behavior of the remaining quantum degrees of freedom. This is an essential step toward Trans-Turing systems.

Note next that in a slightly more refined model, the many nuclei would decohere to classicality in some temporal order and, say, spatial relation. The result is that the now increasing number of classical nuclei will have an ever changing classical Hamiltonian as additional nuclei become classical and interact with one another dynamically, ignoring or not the electron cloud. Thus in a Trans-Turing system, as quantum degrees of freedom decohere to classiciality, or are measured, the classical Hamiltonian changes and exhibits NON-Random Behavior. But that non random behavior IS the classical system itself behaving under the ever changing Hamiltonian, which may move the system on the X axis. In turn, as a generalization of the fact that decoherence into well A versus well B alters the effects of the nuclei on the electron cloud, the behavior of the many nuclei in possible temporally altering behavior, non-randomly alters the effects on the quantum degrees of freedom. Then in the Poised Realm, some of the quantum degrees of freedom can be in superposition states, hence exhibit constructive and destructive interference. By our discussion above, high amplitudes, or amplitudes with high energy and moduli, preferentially decohere. Or, if quantum measured, by the Fermi Golden rule, high amplitudes preferentially are measured. In either case, the altered quantum behavior via constructive and destructive interference and by the Born rule for pure or mixed states, has the consequences that non-random changes are made in which quantum degrees of freedom decohere or are measured and become classical in the next short time interval. In turn this again alters the classical Hamtonian via the newly classical degrees of freedom, which again alters the quantum and Poised Realm degrees of freedom hence which amplitudes decohere to classical behavior or are measured to classical behavior preferentially next. Conversely, REcoherence of classical degrees of freedom, without limitation by driving with a laser light, alters which classical degrees of freedom become quantum, thereby altering non-randomly the classical Hamiltonian and altering non-randomly the consequent poised realm open quantum behaviors and quantum behaviors of the Trans-Turing system.

The above is the heart of a Trans-Turing System. Its behavior is NOT determinant, for either by superposition and constructive and destructive interference plus decoherence preferentially of high amplitude modes with large moduli, or their preferential measurement via the Golden rule, the system is non-determinate. Thus the Trans-Turing system is not algorithmic. But it is also, in its global behavior, non-random. So the behavior is not standard closed quantum system quantum random as in the Schrodinger equation and von Neumann axiomatization of quantum mechanics. The Trans-Turing system is entirely new.

In one embodiment, there are six criteria for a system to exhibit Trans-Turing behavior. First, the system contains quantum degrees of freedom propagating in short lived superposition states that decay rapidly due to decoherence. But these short lived superposition states undergo constructive and destructive interference and will be one basis for a NON-Determinacy in the Trans-Turing system when coupled to decoherence to classicality for all practical purposes, FAPP, or quantum measurement.

Second, either via decoherence or motion out the X axis or both, quantum degrees of freedom become classical FAPP or via quantum measurement, become classical "Simpliciter". Both decoherence and measurement are acausal and yield the non-determinant behavior of the Trans-Turing System.

Third, there are, in addition, coupled classical degrees of freedom in the TTS.

Fourth, when quantum degrees of freedom, and either superposition states or pure states become classical FAPP, or are measured, that ALTERS in different specific ways the effects of the now classical degrees of freedom on one another, thus alters the non-random collective dynamics of the coupled classical degrees of freedom. In turn this altered non-random classical behavior alters non-randomly the behavior of remaining quantum degrees of freedom.

Fifth, in turn this non-random alteration of the behavior of the remaining quantum degrees of freedom alters non-randomly which of the open quantum degrees of freedom decohere or move out the X axis to classicality FAPP. In particular, higher quantum amplitudes tend to decohere with higher probability. So non-randomly altered quantum behavior, including altered constructive and destructive interference, alters non-randomly which amplitudes become higher, thus alters non-randomly which amplitudes decohere to classicality FAPP.

Sixth, in turn, classical FAPP degrees of freedom can recohere, for example, driven by a coherent electromagnetic field whose intensity and period distribution can be tuned non-randomly thereby injecting information. The recoherent degrees may achieve a new controlled superposition state, thereby altering non-randomly the constructive, destructive, and pure states behaviors among themselves and other quantum amplitudes, thereby non-randomly affecting which amplitudes achieve higher amplitudes and tend to decohere, and also non-randomly altering the behaviors of the coupled classical degrees of freedom in the TTS.

Evolution itself indicates that Trans-Turing systems are fully feasible. Mutations in evolving organisms can be quantum indeterminate. Yet evolution in the 11 fold evolution of the eye, the convergence of octopus and human camera eye, the convergent evolution of marsupials and mammals seen in the Tasmanian wolf and mammalian wolf, the streamlined forms of the porpoise and shark, all say evolution by natural selection is strongly NON RANDOM. Thus, the twin pillars of XX century physics, quantum mechanics with its von Neumann measurement Born rule randomness, and Newton's and Einstein's classical physics, literally demonstrates that the evolution of the biosphere itself is not determinate, hence not algorithmic, but not random. So too, the Trans-Turing System. At last we can move beyond the classical physics, algorithmic, Turing machine.

Trans-Turing Information Processing and Acting by Poised Realm Systems.

A Universal Turing Machine consists of an infinite tape a finite alphabet of discrete symbols written on discrete squares on the tape, a finite set of discrete states in a reading head. At each instant, the head is located over one square on the tape. It responds to the symbol on the tape and its internal state by staying in place, moving one square to the left, or one square to the right. It then, depending upon the symbol it read, and its internal state, erases the symbol on the tape below it and writes a symbol, changes from its internal state to one of its internal states, and iterates. All digital algorithms in all computers are based on the Universal Turing Machine.

A critical feature of the Universal Turing Machine is its absolute definiteness. Given an input symbol and a state at a position of the reading head on the tape, the entire future behavior of the system is definitely determined. Despite the famous halting problem, known in the art, the system is algorithmic, definite and an abstraction of a perfect mechanical classical machine.

A second class of computers are classical analogue computers, where, for example, electric circuits mimic the water flow in a system of pipes. These systems are entirely classical if also sometimes chaotic. They may exhibit epistemological indeterminism in that we do not know the initial state with infinite accuracy, but not the ontological indeterminsm of quantum mechanics, the Poised Realm, and Trans-turing systems via decoherence to classicality or quantum measurement of open quantum and Poised realm systems.

It will be clear to those of ordinary skill in the art, that the Poised Realm Systems in described here are neither universal Turing machines, nor classical variable analogue computers. Rather Poised Realm Systems utilize quantum, Poised Realm, and classical degrees of freedom, along with exogenous quantum, Poised Realm, and classical inputs and outputs from and to the environment. The quantum degrees of freedom in the Poised Realm are not limited in any way to quantum COHERENT qubit realizations of Universal Turing Algorithmic Machines as in conventional quantum computers. Rather the quantum degrees of freedom create simple or complex quantum wave patterns, standing or propagating, and, in the Poised Realm, exhibit both superpositions and a finite number of amplitudes with finite positive moduli which can become classical degrees of freedom by decoherence or measurement and can recohere to quantum behaviors, pure or superposition states.

Constructive and destructive interference occurs among the quantum degrees of freedom whether fully coherent, or Poised Realm amplitudes. As described, the sensitivity to decoherence increases with the energy of an amplitude of one or many single or entangled quantum degrees of freedom. In short quantum and Poised Realm amplitude wave crests of amplitudes peak and are likely to decohere to become classical degrees of freedom.

As used herein, the phrase "bright idea" refers to quantum waves whose amplitude moduli are sufficiently great that they have a high probability of decohering to classical degrees of freedom, and thereafter modifying the Hamiltonians governing the classical and quantum behaviors of the system.

The consequence of one bright idea decohering to classicity and modifying the Hamiltonians of the quantum, Poised Realm, and classical system, together with the quantum, Poised Realm and classical inputs to the system, will be a succession of bright ideas and modifications of the classical and quantum Hamiltonians of the Poised Realm system. This dynamics is neither quantum nor classical, neither determinate, hence not algorithmic, nor random. The Hamiltonian keeps changing as quantum or Poised Realm degrees of freedom become classical and classical ones become Poised Realm or quantum coherent.

These changes in the Hamiltonians can move the Poised Realm system on the x-axis from order to criticality to chaos and back, by its own endogenous dynamics and as driven by quantum Poised Realm, or classical inputs. Or alternatively, alteration in the quantum network structure of components of the system can move it on the x-axis either from quantum Poised Realm behavior to classical behavior without movement on the y-axis, or with movement on the y-axis as sensitivity to decoherence and recoherence stimuli and noise change.

We discuss next entanglement among quantum and poised realm degrees of freedom and how the behaviors of those degrees of freedom can be correlated with the "outside world" via the, in general, shaped potential wells, created by the classical degrees of freedom of the system. First quantum entanglement and nonlocal EPR correlations are fully established. We propose use of fixed or SHIFTING patterns of entanglement among quantum and poised realm quantum degrees of freedom in one or a SET OF INTERACTING AND COUPLED TRANS-TURING SYSTEMS. Such entanglement may be achieved by any means known or discovered in the art, including infrared photon couplings among generalized chromophores within one or a set of Trans-Turing systems. Entanglement means that the quantum degrees of freedom are a SINGLE CORRELATED SYSTEM. Hence, with quantum measurement, the measured quantum degrees of freedom of the entangled quantum degrees of freedom ARE correlated and violate Bell's inequalities. Recent results demonstrate that the more degrees of freedom are entangled the GREATER IS THE CORRELATION, in dramatic opposition to the familiar curse of dimensionality in classical physics. Thus either measurement of a plurality of entangled poised realm or quantum degrees of freedom yields a HIGHLY CORRELATED SET OF NOW CLASSICAL DEGREES OF FREEDOM ENABLING COORDINATED ACTION BY THE TRANS-TURING SYSTEM INVOLVING MANY, NOW CLASSICAL, DEGREES OF FREEDOM COUPLED TO ONE ANOTHER AND STABLY CLASSICAL DEGREES OF FREEDOM WITHIN THE TRANS-TURING SYSTEM.

As is know in the art, study of random Boolean networks, RBN, and threshold networks demonstrate a classical physics order, criticality chaos transition. The discrete analogue of the Lyapunov exponent, called the Derrida Curve, shows convergent flow in the ordered regime, neither convergence nor divergence at criticality, and divergent flow in the chaotic regime. We believe the same results hold true for Hamiltonian systems of many nonlinearly coupled variables on the X axis. It is of deep importance that critical RBN show maximum diversity in their behavior as measured by SET COMPLEXITY, ( ) a power law distribution of "avalanches of dynamical change" when a single variable is transiently altered, which allows maximum controlled communication across a network of many variables without tipping into uncontrollable chaos where any noise discoordinates behaviors, yet maximizes useful discrimination of past events. Critical classical systems are optimal with respect to the capacity to classify environments and act reliably in the presence of noise. We propose that single or man coupled CRITICAL Trans-Turing systems, including coupled by entanglement, will allow, after decohrence to classicality or measurement, wide correlation among many now classical degrees of freedom. But more, because these systems are critical with respect to classical behaviors, the richest, most diverse, and coordianted actions and discriminations can occur in such systems.

Further, in the Poised Realm, critical systems exhibit fractal amplitudes which, we believe, for a multiparticle system, may also allow maximal Poised Realm coordination of, for example and without limitation, entangled quantum and Poised Realm degrees of freedom in one or a plurality of coupled Trans-Turing systems.

Because critical PoisedRealm systems resist decoherence best via power law decohrence rather than exponential, they should, by the Fermi Golden rule, or preferential decohrence of high modulus amplutudes, tend to transfer quantum energy to classical energy efficiently.

Consider a classical particle in a box. If we measure its position and momentum we know nothing of the shape of the box! But a quantum wave process in a potential well "knows" in an analogue embodied sense, the boundary conditions constituted by the potential well. This may show up, without limitation, in the eigen values of its energy levels. Thus quantum wave processes, and Poised Realm quantum wave processes in a classical potential, know the 'CONTEXT" OF THAT POTENTIAL.

Now consider the contrast of a digital representation of music in a room by dividing the room into tiny volumes and using a bit series to represent the music, versus a set of 1000 differently shaped drum heads well placed in the room, so "tuned" to sense the music in the room by their joint patterns of vibration, ie the eigenfunction modes of the drum heads. But the drum heads are not coupled. Now consider a plurality of entangled quantum or poised realm degrees of freedom which deocohere to classicality or are measured. They ARE ONE quantum state, they "know" their classical potential surface context. Now, if that surface is tuned to reflect and span the outside world in some more or less organized way, the measured or decoherent hence now classical degrees of freedom "know the "outside world".

The next step is to realize that the decohrence to classicality or measurement process, in reflecting the classical Hamiltonian of the classical degrees of freedom is both the TUNING OF THE QUANTUM WAVE FUNCTIONS to the world outside, like the drum heads, but also the Measurement" bias provided by the classical Hamiltonian of the system as a "measuring instrument. The resulting classical degree of freedom of a single or many entangled degrees of freedom is "the answer", as is a pointer reading in a standard quantum measurement. We will use this below to attempt to solve the Frame problem in algorithmic Turing systems.

It will be clear to those of ordinary skill in the art, that movement of the Poised Realm System only on the x-axis altering the quantum network structure, or in any other way noted above or more generally, can result in quantum, and quantum Poised Realm degrees of freedom becoming more or entirely classical, thereby altering the quantum network and further modifying the position of the Poised Realm system on the x-axis, and by becoming classical, these degrees of freedom can also alter the Hamiltonians of the classical, quantum and Poised Realm degrees of freedom, again inducing motion on the x-axis by endogenous or input driven signals.

Because of quantum, Poised Realm and classical outputs of the system to the environment, actions will be taken by the Poised Realm system on its world, by virtue of the Poised Realm system and the quantum, Poised Realm, and classical input "information" it receives. Thus, the Poised Realm system is an embodied, non-Turing, non-determinate, non-algorithmic, non classical non-random analogue, information processing and acting system that embodies information "analysis," action, and information within the Poised Realm System enabled by the symmetries and broken symmetries of its Hamiltonians, classical and quantum, quantum network structure and driving by quantum or Poised Realm inputs which may move the system on the x and y axes. The broken symmetries of the Hamiltonians can constitute the "tuning" of the quantum "drum heads" if tuned by coupling to the outside world, in one or a plurality of Trans-Turing systems.

Because the classical variables of the Poised Realm system may be endERGONIC or exogONIC processes, these may, in general, be linked into work cycles. Poised realm systems can "build things" by being capable of carrying out thermodynamical work in the context described above.

Design and Evolutionary Selection of Desirable Poised Realm Systems.

Consider first the simulation by digital computers with algorithms, of Poised Realm systems with desired inputs and with outputs. One use of such algorithms is to design Poised Realm systems with input output behaviors that are desired, in rough parallel to the fully computerized design process of the 777 Boeing jet. A second broad application of such algorithms is in any of the many evolutionary selective algorithms that operate on a given algorithmic representation of the behavior of a Poised Realm system, and makes any kind of use of any kind of "heritable variations" and selection of the behaviors of such Poised Realm systems to achieve input/output and internal behaviors that are desired. For example, on rugged fitness landscapes, "long jumps" by big mutations are preferable when fitness is low, but local variations are more effective when fitness is high, in speeding evolution and avoiding trapping on poor local optimal. Genetic Algorithms are just one such evolutionary algorithm known in the art. But algorithmic Turing simulations cannot constitute the real behavior of a Trans-Turing system, for Turing systems are classical physics and Trans-Turing Systems are not.

Figure 10:
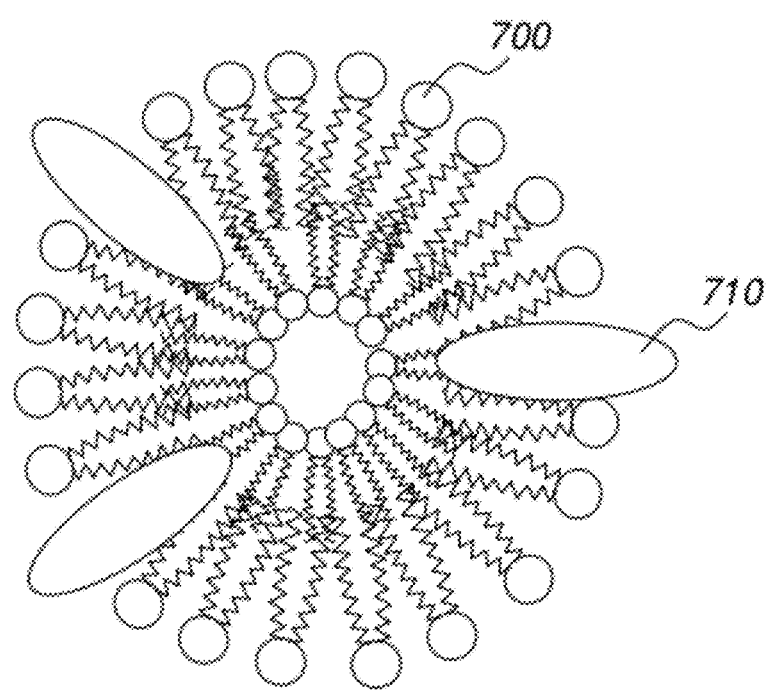
FIG. 10 is diagram of a liposome containing chromophores.

A broad second way to design or evolve desired Poised Realm systems uses without limitation, liposome vesicles with chemical reactions, and chemical constituents in its interior and exterior milieu. With reference to FIG. 10, liposomes contain phospholipid molecules 700 that organize into a bilayer that forms a vesicle with aqueous regions on the inside and outside of the bilayer. Included herein are both unilamelar and multilamelar vesicles. In a Trans-Turing system, the vesicles comprise chromophores 710, including generalized chromophores defined above, in the broad sense (e.g., including chromophores coupled to one another) by binding to beta barrels or other bilipid spanning molecules in the liposome membrane so that the chromophores are inside, or outside or both, of the liposomes and can communicate by broadcast or more specifically with one another, quantum, Poised Realm and classical inputs. The quantum and poised realm degrees of freedom within one liposome or a plurality of liposomes constituting a Trans-Turing system or plurality of such systems may or may not be entangled, as described above. The vesicles can be divided in any way to daughter vesicles with or without replenishment of chemical constituents, and selected for desired Poised Realm behaviors as embodied physical systems. Such systems are both embodied, not representational as are Turing systems, achieve functional closure as autonomous systems, and thus are not simulated on an algorithmic computer, but are embodied systems that exist and behave in the universe.

Generally, to form liposomes with proteins embedded in the bilipid layer a further classical approach is to isolate the protein of interest (generally overexpressed) from living cells, by destroying the cell integrity. Integral membrane proteins are associated to membranes which are broken during the cell distruction but reseal to form lipid vesicles (containing membrane proteins) or membrane fragments.

At this point these membranes (containing proteins) are solubilized with excess detergent and sometimes a synthetic lipid (e.g. POPC) to form mixed micelles (detergent+cell lipids+POPC+membrane proteins). In each concrete case, it is routine to find the best detergent for solubilizing the protein without destabilizing its 3D structure and interaction with very proximal lipids. Typical examples are sodium cholate, and octyl-glucoside, digitonin, dodecyl maltoside, and Triton-X-100.

Now the detergent can be removed by dialysis or gel filtration chromatography or adsorbption on biobeads or simply by dilution. Detergent is preferentially removed due to its higher solubility in water. The product are lipid vesicles (possibly containing some cell lipids) containing the protein of interest. The typical size is 50-100 nm. But the presence of the protein can affect the size. These integral-protein-containing liposomes are called "proteoliposomes". The procedure to prepare liposomes in this way is called "detergent depletion method".

At first approximation, proteins are oriented 50% inward and 50% outward, so for every vectorial application, 50% of protein is not active.

Further discussion of liposome manufacturing techniques suitable to make the structures described herein may be found in Silvius, J. R. (1992) Solubilization and Functional Reconstitution of Biomembrane Components. Annu. Rev. Biophys. Biomol. Struct. 21, 323-348 and J. -L. Rigaud, B. Pitard, D. Levy. Reconstitution of membrane proteins into liposomes: application to energy-transducing membrane proteins. Biochimica et Biophysica Acta 1231 (1995) 223-246, both of which may be incorporated herein by reference in its entirety. Examples are described in: Goodwin Mg, Jackson Jb, Electrochromic Responses Of Carotenoid Absorbency Bands In Purified Light-Harvesting Complexes From Rhodobacter-Capsulatus Reconstituted Into Liposomes, Biochimica Et Biophysica Acta Volume: 1144 Issue: 2 Pages: 191-198 Published: Sep. 13, 1993; Jackson Jb, Goodwin Mg, Electrochromic Responses Of Bacteriochlorophyll Absorbency Bands In Purified Light-Harvesting Complexes Of Rhodobacter-Capsulatus Reconstituted Into Liposomes, Biochimica Et Biophysica Acta Volume: 1144 Issue: 2 Pages: 199-203 Published: Sep. 13, 1993; and Kobayashi M, Fujioka Y, Mori T, Terashima M, Suzuki H, Shimada Y, Saito T, Wang Z Y, Nozawa T, Reconstitution of photosynthetic reaction centers and core antenna-reaction center complexes in liposomes and their thermal stability, Bioscience Biotechnology And Biochemistry Volume: 69 Issue: 6 Pages: 1130-1136 Published: JUN 2005; all of which are incorporated herein by reference in their entirety.

In order to make giant liposome vesicles, GVs, the vesicles produced as above are dried over an electrode and after application of alternate current, GVs are formed, and they contain the integral membrane protein in the membrane. This is a variant of the "electroswelling method". See Philippe Girard, Jacques Pécréaux, Guillaume Lenoir, Pierre Falson, Jean-Louis Rigaud, Patricia Bassereau, A New Method for the Reconstitution of Membrane Proteins into Giant Unilamellar Vesicles, Biophysical Journal-1 Jul. 2004 (Vol. 87, Issue 1, pp. 419-429), which is incorporated herein by reference in its entirety. Alternatively, the proteoliposomes formed after detergent depletion can be lyophylized and hydrated without stirring. This corresponds to a sort of "natural swelling" method that should give protein-containing giant vesicles.

Liposomes can bud as is known in the art. By budding in the presence of free and covalently anchored chromophores linked thereby to betabarrel proteins in the aqueous medium or other similar molecules, these chromophores will melt into the membrane and become anchored there. Thus the density per liposome of chromophores, and their spectral characteristics can be altered. Since coupling of two chromophores depends upon emission of a quantum by one chromophore whose size can be absorbed by the second, tuning the chromophore absorption spectra and ratios in a liposome partially controls the topology of the quantum network, hence position of the liposome system on the x-axis.

Here, rather than using a genetic algorithm of any kind REAL EVOLUTION of embodied liposomes coupled or not, or any other embodied systems capable of any kind of reproduction, division, heritable variation and selection after Darwin, can be used to evolve desired input, Trans-Turing "computation" and output behaviors, quantum, Poised Realm, and classical.

It will be clear to one of ordinary skill in the art that one preferred embodiment of the current invention is able to evolve a population of single or interacting Trans-Turing systems to achieve with more or less success, a high diversity of success criteria or figures of merit. In general, one approach to this is to use any one or combination of the wide variety of known in the art methods for evolution of such devices. The Holland Genetic Algorithm and its many variants are but one set of examples.

In the broadest terms, the inputs to a Trans-Turing system can be any single or combination of coherent quantum behaviors, poised realm behaviors, or classical behaviors of single or many degrees of freedom. The outputs can similarly be any one or a plurality of quantum coherent, poised realm or classical degrees of freedom. In general, only classical degrees of freedom, including quantum measured degrees of freedom without their being a limiting example, can serve as readily sampled outputs.

In general, the inputs to the quantum system will be transformed into the outputs of the Trans-Turing system. The Trans-turing system, may, like a feed forward neural net, have no internal dynamical attractors including potential wells, or it may have potential wells of the classical variables which are capable of such behavior, without limitation, because they typically can exhibit dissipative dynamics. These alternative attractors, including without limit, potential wells, can be used to classify diverse inputs, including those which are constant in time, into the different attractors of the classical variables of the Trans-turing system, where which attractor is attained for some period of time depends in general on the initial state of the Trans-Turing system as well as its inputs.

As an entirely non-limiting example of such input-output and classification by a Trans-Turing system achieved by any form of evolutionary search, we consider a Trans-turing system consisting of a single liposome containing chlrophyll and surrounding antenna proteins. As a non-limiting example, the antenna protein or any other molecule like it, will float in the liposome lipid bilayer. In general, rafting will occur bringing the diverse chlorophyll and antenna proteins into proximity, for example without limitation by van der Waals forces. In general any such molecule has a longer axis. Without limitation, use red and green quantum dots or fluorescent dyes to label the two defined "head" and "tail" ends of the long axis of such a molecule as chlorophyll wrapped by the antenna protein.

Then by any means known in the art, the orientation of any two or more labeled chlorophyll and antenna proteins in the lipid bilayer can easily be assessed by standard techniques. Thus, it will be clear to those of ordinary skill in the art, that for a plurality of two or more red and green labeled molecules, here, without limitation, taken to be chlorophyll molecules each wrapped by its labeled red and green antenna protein, the relative orientations and distances among these molecules floating in the liposome membrane can be assessed. These classical degrees of freedom, without limitation, ca be taken as one possible out of indefinitely many, classical "output variables".

We note that the success criterion, or "figure of merit" may be a steady state of our output variables or any time varying dynamical behaviors, and the input variables may be steady states, time varying states, stationary statistical distributions or non-stationary distributions. Here we consider the simplest case of steady inputs and their mapping to steady outputs.

Without limitation, we take as a concrete example of input variables two lasers with different wavelengths that shine on the single liposome. The intensity ratio and wavelengths of these laser lights can be taken as an input "spectrum". For N input laser frequences there is an N dimensional input space.

As a second classical variable input set we take sound vibrations at two or more frequencies in which the ratio of the power intensities of the different frequencies, and those frequencies themselves can be changed to cover an N dimensional input space for N input frequencies.

For either the quantum laser, or classical sound vibration input spectrum, for each point in the N dimensional input space, the relative orientations and distances of the red and green labeled, without limitation, chlorophyll and antenna protein complexes can be asses by light scattering, image analysis or any other means including mathematical analysis of the orientations and distances among the output red and green labeled molecules which may raft together to various degrees in the bilipid layer.

A mapping from input space to the output variables whose relative positions constitute an output space can now be established.

Without limitation, it may be desired to achieve a Trans-turing system that maps each point in the input space to a unique point, bijectively, in the output space. Alternatively it may be desired to "classify" subsets of the input space to the SAME output point in the output space. In general this classification can arise if the Trans-Turing system has attractors such as a plurality of two or more potential wells that are expressed in two different stable or statistically discriminable behaviors of the output variables.

To achieve such a one to one bijective mapping, or a many to one classification of the input space to the output space, a diversity of evolutionary algorithms may be carried out.

Without limitation, let the Trans-turing systems above be liposomes with controllable densities of chlorophyll and antenna proteins dissolved in the bilipid layer, with additional classical control parameters such as the hypertonicity or hypotonicity of the medium leading to swelling or shrinking of the liposome, to a diversity of lipids altering the physical-chemical characteristics of the liposome bilipid layer and hence the rafting and other behaviors of the chlorophyll and antenna proteins floating in the bilipid membrane, hence their collective behaviors under van der wal and other forces. Other classical inputs can be electric and magnetic fields, temperature, pressure, and so forth.

Call these variables, which can be classical, quantum coherent, or poised realm, the CONTROL PARAMETER SPACE. An evolutionary search in this "control parameter space" is undertaken by varieties of evolutionary algorithms, below, to "hill climb" to points in the control space that optimize the desired input output behavior of the Trans-turing systems to obtain at least one or a plurality of Trans-Turing systems that performs as optimally as is attainable given the complexity of the search space and ruggedness of the resulting "fitness lanscape" ie the distribution of the desired behavior or "figure of merit" across the Control Parameter Space. As is well known in the art, the success of evolutionary search by variations alone or with any analogue of recombination, depends upon the ruggedness of the "fitness landscape" for the "figure of merit". In general, forms of recombination perform poorly on quite or very rugged landscapes. Also, when fitness is low, larger variations in Control space parameters followed by smaller variations as fitness increases, can optimize evolutionary search. In addition, the very process of evolutionary search can be used to establish the statistical features of the fitness landscape as is known in the art.

Using these parameters, let an initial population of, without limitation, 1000 liposome Trans-turing systems be constructed and tested individually for their input output mapping, where the initial figure of merit of each liposome Trans-turing system is established and correlated to the positions of each in the Control Parameter space.

Again, without limitation, one or some plurality of the fittest liposome Trans-Turing systems are used as seeds for a second generation of liposomes. To be concrete, let, without limitation, the 100 fittest liposomes be used as this seed. Then construct from each of these 9 new liposomes differing from it at defined distances in the Control Parameter space, with the distances tuned to the current fitness and the ruggedness of the landscape as it becomes established. This creates a second generation of liposome Trans turing systems, here without any form of recombination.

Iterate the above and assess the figure of merit for the new second generation of liposome Trans-Turing systems, again pick the 100 best, and form a new 1000 liposome third generation. Iterate this process as many times as desired, as fitness increases.

This is the core of an evolutionary search process, here using liposomes as Trans-Turing systems, and so far without any analogue of recombination.

Recombination can be implemented by taking two or a plurality of members of the chosen seed set, here 100 liposomes, and forming the new generation by considering the Euclidian or, for discrete Control Paremeters in the control parameter space, the Normalized Compression Distance, between any two or any pair of more than two members of the seed set. New points can be chosen at any distance from any one liposome toward any other single or set of liposomes in the control parameter space, by simple means known in the art. This is a kind of "sharing of information" among the seed set to form the next generation for evolutionary search. In general, too much sharing is unfavorable on a rugged multi-peaked landscape where it may cause trapping of all on poor local optima. Thus as the structure of the landcape is discovered using means known in the art, by the evolutionary sampling process itself, the preferred ratio of mere variation and "generalized recombination or "sharing" can be tuned to optimally search the landscape.

By these means, for any input space, output space and figure of merit, Trans-turing systems well adapted to any single figure of merit can be attained.

More generally, there may be more than a single figure of merit, where the relative importance of the different figures of merit are unknown. Here the standard solution concept is "Global Pareto Optimality", ie points in the Control Parameter Space where no motion can occur that increases ONE figure of merit without lowering one or more other figures of merit. Among such Pareto optimal points, the global pareto optimal set is such that no other Pareto optimal points are "better" on any of the figures of merit that the Global Pareto Optimal Points. In general, each figure of merit creates its own smooth or rugged fitness landscape, and the search for global pareto optimal points can be difficult, but in general is possible. A theorem proves that among the Global Pareto optimal points, each global optima of any one of the figure of merit fitness landscapes is one of the Global Pareto optimal points. Thus if finding a global optimum of a single figure of merit is feasible or even easy on smooth landscapes, finding some Global Pareto Optimal points is readily achieved.

It will be clear to those of ordinary skill in the art, that these evolutionary search processes can be used for any form of Trans-turing system, whether liposomes, nanofabricated with nanotubes or constructed in any other ways.

The same evolutionary search processes generalize to a plurality of two or more Trans-Turing systems which are coupled in any way, classically, by entanglement, or in other ways of coupling quantum coherent degrees of freedom or poised realm degrees of freedom. To use our concrete example of an output space generalized to M liposomes, there is now an N×M input space and an N×M output space, and an N×M Control Parameter space for N control parameters per trans-turing system. The same evolutionary procedures apply, with the figure of merit able to be far more complex because it now involves possible steady state and for any single Trans-Turing system or plurality of them, complex classical, poised realm and quantum coherent behaviors.

Quantum dots, as known in the art, absorb and emit photons. Large dots absorb in the red, small dots in the blue. So smaller dot sizes changes the absorption spectrum toward shorter wave lengths. Quantum dots have a number of higher excited states emitting, by Fermi's Golden Rule, preferentially their largest quanta as they fall from their higher energy states to their ground states. This can allow quantum dots of different sizes to be coupled by photon exchanges in liposomes or more generally in any setting including nano-fabrication in Trans-Turing systems.

Similarly, quite subcritical chromophore coupled systems with small trees will absorb and emit photons that are shorter wavelength than larger trees closer on the x-axis to critical. These absorption spectra can be tested. The distribution of tree sizes in a liposome or on a nanodevice will tune the overall connectivity of the entire system, hence position on the x-axis. Again, the presence of multiple energy levels per quantum tree of various tree sizes can allow the trees to communicate by emitted and absorbed photons in a tunable way.

For liposomes, exposure to hypotonic and hypertonic solutions will swell or shrink the liposome altering the proximity of chromophores hence their photon mediated connectivity, hence position on the x-axis. Swollen liposomes will be further left on the x-axis than the same liposome if shrunk in a hypertonic solution.

In one nonlimiting preferred mode of evolution of Poised Realm systems, the liposome contains an autocatalytic set of polymers and catalysts that catalyze a sequence of chemical reactions to create the building blocks of the polymers Recent work by Serra has shown that under these conditions, autocatalytic set and liposome division SYNCRHONIZE, enabling the open ended evolution demonstrated by Szathmary et al. in silico. This is a generalization of Ashkenazi's nine peptide autocatalytic set, now experimentally achieved. We will call such systems Poised Realm Protocells, subject to heritable variation. Natural selection and even co-evolution of such systems in defined or variable environments can be carried out to achieve Poised Realm protocells with desired input, output and internal behaviors. More, such systems will interact not only by catalysis, but by myriad classical causal features enabling Darwinian preadaptations and the emergence of novel functions, as discussed by Kauffman in his books Investigations and Reinventing the Sacred. Because these systems, like evolution in general, marry quantum, poised realm, and classical degrees of freedom, and are autonomous Kantian systems with top down and bottom up causality, they escape mere reductionism, and can show emergent behaviors. For example swim bladders in some fish with a tunable ratio of air and water allow neutral buoyancy in the water column. Paleontologists believe that these arose as unused causal consequences of the lungs of lung fish as Darwinian preadaptations, or exaptations. In Reinventing the Sacred Kauffman shows that we cannot prestate the state space of the evolving biosphere, hence further we cannot know the boundary conditions on selection, so we cannot have entailing law. But more, the swim bladder, which arose due to selection in a population of fish for good function AS A SWIM BLADDER, HAD THE FURTHER PROPERTY THAT, ONCE IT EXISTED, IT CONSTITUTED AN ADJACENT POSSIBLE EMPTY NICHE. A bacterium might evolve only able to live in swim bladders, like a bacterium only able to live in the lungs of sheep. BUT NOTE THAT NO SELECTION AT ALL ACTED TO CREATE THE SWIM BLADDER AS A NEW ADJACENT POSSIBLE EMPTY NICHE! The new empty adjacent possible niche, "just arose". But this means something astonishing: the biosphere is literally building, without selection, the very possibilities it will become.

In an exactly parallel fashion, evolving and coevolving Trans-Turing Protocells can and will undergo Darwinian preadaptations and create "emergent" adjacent possible empty niches for more such Trans-Turing Protocells. By these means, and those below, the frame problem of Turing machines and computer science can be solved: novel functionalities and solutions to problems can be found under appropriate selective conditions.

It will be clear to those of ordinary skill in the art, that any platform, beyond liposomes, that can hold "generalized chromophores" in a changing or fixed spatial arrangement, can be used. In particular, if these can grow and divide spontaneously or non-spontaneously, and in any form undergo "heritable variations" needed for evolution or even open ended evolution, populations of Poised Realm Systems that can be selected for desired behaviors can be obtained and evolved.

In addition to Trans-Turing protocells that can evolve, this invention can be used in another way to evolve single or coupled Trans-Turing systems for desired behaviors. Specifically, Trans-Turing systems can be nanofabricated or micro or macrofabricated. An evolutionary procedure can be carried out by an embodied version of something like the Genetic algorithm, but, because embodied, beyond it. Here a population of a plurality of single or coupled Trans-Turing systems, without loss of generality, nanofabricated ones, can be tested for a desired behavior. The best one or a subset of the initial population can then be used in a variety of ways to construct a second generation which might include the best one or plurality of the first generation, and small mutant variants of these Trans-Turing systems. Over a succession of generations, as the evolve and by interacting with one another, co-evolve, improve performance can be sought. Because these systems are embodied and have real Poised realm and classical consequences in the physical world, they evolve in it without digitally representing that world, as in Turing machines and the Holland Genetic algorithm. Thus, the famous and unsolved "frame problem" which bedevils Turing systems, does not even arise for these embodied systems, for they evolve without digitally or algorithmically representing their worlds.

By use of direct design, the use of digital algorithms both to simulate and evolve in silico, as described above, or nanofabrication of embodied Trans-Turing systems, alone or coupled sets of them, nanotechnology can design/evolve and co-evolve and build Poised Realm devices with desirable properties, including input and output behaviors that are trans-Turing in their information processing. Such systems are not algorithmic in the Turing sense, nor classical physics analogue computers which at most have epistemological indeterminism via determinstic chaos, while Trans-Turing systems have ontological non-determinism, yet analyze input quantum, Poised Realm, and classical data, have "bright ideas" that become classical degrees of freedom, alter Hamiltonians or quantum network topology, hence position on the x-axis by endogenous dynamics and due to quantum, Poised Realm, and classical inputs, yield a sequence of bright ideas and sequences of data analyses and quantum, Poised Realm, and classical actions on the world by the embodied information processing, hence SEMANTIC system. In one embodiment of this invention, Trans-Turing Protocells are Kantian Organized Systems and achieve Kepa Ruiz Mirazo's "autonomy" such that the parts exist in the universe for and by means of the whole, and the whole exists in the universe for and by means of the parts whose behaviors it organizes. We call these "Autonomous Trans-Turing systems". They will be of use in affording a natural definition below of R. Ashby's "Essential Variables" as an internal goal state of a Trans-Turing system or coupled set of Trans-Turing systems.

It will be clear now, that such novel systems exhibit dynamics that are neither Schrodinger closed system quantum mechanical, nor classical deterministic dynamics. THE SYSTEMS ARE NEITHER DETERMINISTIC, hence are non-algorithmic, and are NOT random. These Poised Realm Trans-Turing systems exhibit novel dynamics allowing entirely novel information processing, internal behaviors, and output behaviors among quantum, Poised Realm, and classical degrees of freedom.

Embodied Poised Realm Systems can Form Communicating and Acting Networks.

Poised realm systems, without loss of generality, liposomes or nanotechnology devices, or otherwise, can form arbitrary networks in which quantum or Poised Realm, or classical degrees of freedom can be communicated between Poised Realm systems such that they interact as a "community". Coupling can be by any means known in the art, including broadcast, waveguides directing photons emitted by one Poised Realm system and directed to one or a plurality of other Poised Realm systems, use of quantum wires, fiber optic cables, carbon nanotubes or any other means of communication. As noted above the quantum and Poised Realm degrees of freedom may be quantum entangled. More, recent work shows that such an entangled system can alter which degrees of freedom are entangled. Because quantum measurement or decohrence to classicality constitutes the formation of correlated sets of now classical variables via that entanglement, and the pattern of entanglement can change, we can think of this as a kind of "shifting of attention" by the Trans-Turing system or coupled set of Trans-turing systems. After the entangled degrees of freedom shift, a different set of quantum or poised realm variables become classical with consequences for the coordinated behaviors of the classical and Poised realm aspects of the system.

By such communication, communities of Poised Realm Systems can perform tasks and information processing and acting that no single Poised Realm system can attain.

More co-evolution and other "adaptive procedures" or community assembly procedures, analogous to community assembly in ecology, can be used to obtain Poised Realm communities with desired properties. Among these may be a maximal power efficiency per unit "fuel" or energy input to the Poised Realm devices, at a finite displacement from equilibrium. Recent results suggest that bacteria grow at a rate that maximizes biomass production per unit fuel, here glucose, as input to the system. This picks a specific displacement from thermodynamic equilibrium as optimal with respect to power efficiency per unit fuel for such systems. We here generalize this to Poised Realm systems performing any kinds of tasks with optimum power efficiency per unit fuel.

Ecologists suspect a similar maximum power efficiency for ecosystems. We can evolve communities of Poised Realm systems to maximize a power efficiency per unit "input," energy, or information as described below, or both or more general success criteria.

As noted above, Critical Trans-Turing systems and either preferential decoherence of high amplitudes to classical degrees of freedom or quantum measurement and Fermi's Golden rule, coupled with the mere power law decoherence of Critical poised realm systems, implies that maximum power transfer from quantum to classical degrees of freedom can be obtained. Maximum power efficiency may be attainable.

Using Essential Variables to Enable Goal Behavior.

In Design for a Brain by Ross Ashby, 1960s, Ashby designed a self-repairing algorithmic system, the homeostat. He considers a system of N variables, discrete variables and discrete time. He designates a subset, E<N, of these as "Essential Variables," each of which must be kept with "bounds" given the range of values of each variables. Call this bounded region the "Alive Box." The system must keep within the Alive Box. Note that in an Kantian Autonomous system that gets to exist in the universe, the means of parts and the whole by which the Atuonomous system sustains itself constitutes its Essential variables.

The N variables comprise a dynamical system with state cycle dynamical attractors and basins of attractions draining into each state cycle as is known in the art. See Kauffman's Origin of Order as a nonlimiting example.

The system is released from an initial state, flows to an attractor and either does or does not keep within the Alive Box. If yes, the system remains in that attractor of the N variables. If not, it reinitiates at a random state in the state space and flows to an attractor. Again if the system stays within the Alive Box, it remains in that attractor, if not the process is iterated.

If the system fails to remain in the Alive box after some number of random initial states, Ashby implements a "step change" in a parameter to one of the variables. This step change can change the "phase space portrait" of where the basins of attraction and attractors are located.

Again, the system is released from random initial states and if it remains for one of these in the Alive Box, the system stops. Otherwise after a number of initial states have been sampled, a step parameter is again changed. The process is iterated until a value of the parameters is found that allows at least one attractor of the N variable system to keep within the Alive Box.

These ideas are fully applicable to Poised Realm systems. A subset of the classical variables are designated as essential variables.

In continuous nonlinear dynamical systems with attractors and parameters, at a bifurcation point in parameter space, new attractor(s) may appear, old ones disappear, and the locations of basins of attraction draining continuous trajectories into attractors may change.

In a Poised Realm System, the decoherence on the y-axis, or motion on the x-axis, of a quantum degree of freedom to a classical degree of freedom can operate on the Hamiltonian, or quantum network structure of the classical and quantum systems as a parametric bifurcation parameter. Indeed, continuous variation on the y-axis from quantum to classical can act as a bifurcation parameter as do motions on the x-axis or both the X and Y axes. In addition, quantum or classical parameters can be changed. The recoherence of a classical degree of freedom, or motion toward order on the x-axis, can act as a bifurcation parameter to the classical and quantum Hamiltonians. In addition, inputs, classical or quantum, may drive the system between attractors or drive the system so rapidly that attractors are not attained and maintained. However, the average time spent in the Alive Box is always definable.

To create a Poised Realm System "homeostat" we carry out the processes noted above. The Poised Realm system keeps changing by decoherence or recoherence of quantum or classical degrees of freedom, or changes in classical or quantum parameters, or changes in inputs, until the system maintains itself in the Alive Box.

This architecture endows the Poised realm system with "primary drives", i.e., to keep within the Alive Box.

Choosing Essential Variables.

As noted above, choosing essential variables is not trivial. In Poised Realm evolving protocells, examples of Kantian autonomous Trans-Turing protocells, autonomy itself that maintains the Kantian organized being in the universe, alone or in the presence of natural selection for evolving protocells picks the relevant essential variables and their embodied classical causal consequences that form a functional closure of tasks by which the Kantian system sustains itself. These are the variables whose change increases "fitness" by whatever success criteria is in operation.

Note that for embodied Trans-Turing protocells as autonomnous systems, adaptation and preadaptations using existing causal features of the classical variables for novel functionalities, or "tasks" that achieve "task" closure in a set of tasks (like a dividing eukaryote), solves the frame problem. Again, the system does NOT represent its world digitally. It exists and evolves as an embodied Trans-Turing System or a coupled plurality of them, perhaps as a population that evolves or co-evolves, in an environment. New functions and tasks achieved by new "uses" of causal features of the classical variables, enabled also by the Poised Realm and other Trans-Turing features of the system, promote adaptation. Selection for desired behaviors is then carried out, as in biology.

For an evolving population of mutated budding liposomes or generations of mutant liposomes where the ratio and density of chromophores with different absorption/emission spectra are varied, hence varying quantum network connectivity and position on the x-axis, those variables which strongly alter fitness for the desired goal are good candidates for essential variables. The same is true for an evolving population of nanotech devices with similar mutations in chromophore, carbon nanotube structures and specra, and topologies of connections. Those variations which strongly affect fitness for the desired goal are good candidates for essential variables.

Secondary Goals.

Biology teaches us that evolution can achieve tasks via a sequence of evolved subtasks. Ontogeny is a prime example. It will be clear that the embodied Trans-Turing system protocell Autonomous system(s), in an environment with inputs, classical and quantum, and outputs acting on the world, classical and quantum, may attain states and Hamiltonians which can serve as subgoals. Here, the Essential Variables may or may not be kept within the Alive Box, but a different, perhaps overlapping set of sub-essential variables are kept within their own bounds, Secondary Alive Box. From the Secondary Alive Box, the Poised Realm System can attain the Alive Box by some variety of "simple" steps. Without limitation, a simple "step" is to initiate the Poised Realm System in a quantum, Poised Realm, and classical state which is near that which attains the Secondary Alive Box, and from this state, the system flows, with or without decoherence and recoherence of quantum, Poised Realm, and classical variables that change the classical and quantum Hamiltonian, readily to the Alive Box sustaining configuration of the system.

A partial ordering or hierarchy of Secondary and Tertiary Alive Box configurations of the Poised Realm system can sometimes be found, with access via these partial orderings or hierarchial orderings to the configuration of the Poised Realm system such that it remains in the Alive Box. The partial ordering leads from a single or more generality a plurality of Nth level Alive boxes to one or a plurality of N-1 or lower level N-2,3, alive boxes.

Beyond Autonomous Trans-Turing systems undergoing embodied evolution, there is a second means of perhaps much more rapid non-biological "learning" of adaptive behavior, goals and subgoals that solves the frame problem. As a non-limiting example, subdivide the Essential Variable Alive box into successively smaller subspaces that contain one another, labeled 1,2,3,4,5 meaning "getting better, 1→5" This is an analogue of an emotional human response to solving a problem where even the "form" of the solution is unknown hence beyond solution algorithmically due to the frame problem. Now, we have seen that high amplitudes with high energy and moduli preferentially decohere, and have called them "bright ideas". Decoherence or measurement typically leads to decoherence or measurement of high moduli amplitudes. In turn this leads to a slight modification of the classical Hamiltonian and results in a change in the Hamiltonian of the quantum system. A succession of measurements or decohrence events leads to a succession of "bright ideas" becoming classical, so a succession of modifications of the classical Hamiltonian and Hamiltonian of the quantum system. Think of these decoherence events, or measurement events carried out by the classical degrees of freedom on the quantum degrees of freedom in some basis that the classical degrees of freedom constitute as "asking a question" and getting a classical variable answer in a single, or entangled set of open quantum or Poised Realm variables when so measured. The results of the now classical variables may be to move the system from box 1 in the Alive box toward Box 2, then 3, then finally 5. Call being in the 5 box A Solution. Then the system has gone through a succession of measurement or decoherence questions, a sequence of classical variable answers, until it finds a solution that keeps the system in the "happy" box 5. At that point, the system either stops changing as in Ashby's case, or uses the relevant classical variables as a memory store for the solution given the problem. In order to adapt to different problems in different "environments", the system may need to "ignore" the memory classical variables. This may be possible by rendering them quantum or poised realm again via recoherence. As quantum degrees of freedom again, they cannot affect the behaviors of the classical degrees of freedom of the system. The details remain to be worked out.

Operant Conditioning of Poised Realm Systems.

Given the Alive Box and a diversity of Secondary and Tertiary and higher order Alive Boxes, the Poised Realm system needs memory classical degrees of freedom. As noted above, such memory degrees of freedom can arise by decoherence of quantum degrees of freedom where these degrees of freedom can remain classical indefinitely. Or they can become classical by measurement and remain classical including by the quantum zeno effect. Or they can become classical by motion on the x-axis. Once memory variables exist, they serve as bifurcation parameters in the classical Hamiltonian of the total system.

These Memory classical variables maintain aspects of the classical, Poised Realm, and quantum Hamiltonians of the total Poised Realm system such that the Alive box and sub-boxes can be attained and sustained.

Given such Memory variables, the Poised Realm System can undergo "operant conditioning". Given some input to the system, it attains a subgoal Alive box from which it can attain the Alive Box. In the subgoal box, memory classical variables arise by decoherence on the Y, motion on the x-axis or both X and Y axes, so classical parameters change, and the system attains the Alive box. Given the classical state of the now classical memory variables, the system responds to the inputs from the world by attaining either the subgoal box, or directly the Alive box.

Given the Alive Box and decoherence or motion on the x-axis, of quantum variables to classical Memory variables which can remain classical for long periods of time, as well as classical variables which can become partially or completely quantum, both of which change the Hamiltonian's of the quantum and classical systems, hence their dynamical behavior, the Alive Box serves as "internal motivation" as in Ashby's Homeostat, and the Poised Realm system will search on its own means to use any input stream of quantum or classical data, its own internal quantum and classical Poised Realm dynamics, and its outputs—which it may "observe", for example via sensors, the Poised Realm System will search and often attain a state that takes the input stream and with or without subgoal boxes, old or new, achieve a state that remains in the Alive Box. Thus, the Poised Realm System has "learned" to map some aspects of the input data stream to specific internal structures and dynamics, including the memory variables, and learned at the same time to map the inputs to useful outputs that keep the Poised system in the Alive Box.

More on Attention in the Poised Realm System.

By virtue of the classical Hamiltonian, or any other classical system, without limitation, a nonlinear dynamical system capable of order, criticality and chaos, as evidenced by work on Random Boolean networks, Piecewise linear networks, linear ODE networks, and Threshold Tan h function networks, and the possible entangled (and possibly measured entangled) correlated quantum behavior in the Poised Realm, the system with quantum, Poised Realm, and classical inputs may "focus attention" on any subset of its input stream, internal state—which it may sense by sensor degrees of freedom—and output behavior—which again it may sense. Thus the Poised Realm system need not be effected by all inputs, quantum or otherwise. Or that effect may be very minimal, so that the system "sees" and "responds" to focused aspects of its inputs, internal states, and outputs. Again we note that shifting patterns of entanglement, as is known in the art, allow sequential shifting of the focus of attention.

By "focusing attention" on any subset of inputs, and carrying out both data processing and actions coupled to that input, the total behavior can become relevant, without limitation, to keeping the system in the Alive Box. Thus, the system can "notice" features of its environment and actions, and modify its behavior to keep subgoals attained, or remain within the Alive Box.

There is an analogy between a quantum degree of freedom becoming classical for some period of time and the "step changes in parameters" advocated by R. Ashby in his "Design for a Brain" to change the system such that essential variables are kept within bounds. In addition, there is a similarity between the changes in the Hamiltonian of a Poised Realm system, when some of its quantum degrees of freedom become classical, and the preparation of a quantum system plus is classical components in a quantum experiment by measurements that make quantum degrees of freedom classical in the prepared quantum system. In effect, this preparation step can be thought of as reshaping the classical and quantum Hamiltonians of the prepared system thereby picking a favored pointer basis.

This has a bearing on quantum computation where the quantum algorithm can be thought of as reshaping the Hamiltonian of the quantum system, which then accumulates high modulus amplitudes in the vicinity of the solution so that von Neumann consistent measurement is likely to give the "right answer" after a number of measurements. Thus, the spontaneous dynamics of a Poised Realm system where, given the current Hamiltonians of the classical and quantum system, some amplitudes can "peak" to high moduli and remain quantum or can decohere preferentially to classical "answers" to a "question" posed by the current Hamiltonians. Thus, such Poised Realm systems appear to be non-algorithmic quantum-Poised Realm-classical computing and "doing" systems.

In a general sense, what we here call a change in the Hamiltonian of a quantum and/or classical system when a quantum degree of freedom decoheres to classicity for all practical purposes is similar to the Born-Oppenheimer approximation for "effective Hamiltonians" due to slow and fast changing variables such as nuclear positions and electron cloud distributions in molecules. Note that Salahub et al used this approximation in their paper, as described above.

The Diversity of Organized Behaviors of Poised Realm Systems.

Kauffman introduced Random Boolean networks as models of genetic regulatory networks in 1967 and 1969 (see Reinventng the Sacred, by S. Kauffman Oxford UP 1993, 1995, 2000 and Basic Books 2008). These systems, and continuous cousins including piecewise linear equations by L. Glass, linear code systems by S. Thurner, and nonlinear threshold networks by M. Andrecut and Kauffman, show that such systems behave in an ordered regime, a chaotic regime and an "edge of chaos" critical phase transition.

Critical networks exhibit remarkable features, ranging from maximum storage of information (Shmulevich), maximum pairwise mutual information (Ribeiro et al.), maximum Set Complexity, explained further below (Galas et al.), maximum power efficiency (Carteret et al.), maximum capacity to evolve gracefully (Aldana et al.), maximum capacity to make reliable discriminations of past events and reliable action in the presence of minor noise, and maximum capacity in a "society" of networks that can influence one another to create novel attractor behaviors in the members of the society or "tissue" or "colony" (Damiana et al.).

Galas et al. have introduced a new measure of the diversity of organized processes a classical causal system can carry out, called set complexity. Consider a random binary string, e.g., (10100010). Concatenate this string with itself, (1010001010100010). Now use a compressor such as gzip to compress the concatenated string. Since the concatenated random string is redundant, and of length, here N=8, for the initial string, the compressor will reduce the concatenated string length 2×N, to length N by eliminating redundancy. Now take two different random strings length N, and concatenate them and try to compress them. They cannot be compressed, so remain length 2N. Normalized Compression Distance is a universal distance measure between objects such as binary strings. The extent to which two strings, concatenated, can be compressed is a measure of the similarity between the strings. That similarity is a distance measure, and is normalized by dividing by N.

Set Complexity is a new measure for such objects. Let there be M such, without loss of generality, binary strings of length N. Calculate the pairwise normalized compression distance for all distinct pairs of strings and normalize by the number of pairs to find the average normalized compression distance among M strings. Call this average, E. Set Complexity is defined as SC=E×(1−E). This measure is 0 if E=0 or 1 and reaches a maximum for E=0.5.

The intuition behind set complexity is that M identical binary strings must have low set complexity, and also M strings that are random with respect to one another must have low set complexity. Thus set complexity reaches a maximum for intermediate values of E. It is a new measure of the diversity of objects, or, if the symbols represent actions by variables, e.g., the output values of N variables in a random Boolean net, it represents the diversity of organized processes of the classically causal systems.

It is exciting that critical Random Boolean Nets sharply maximize Set Complexity defined over the M states on all state cycles of the network. In short, the asymptotic behavior of critical random Boolean nets maximizes the organized diversity of processes such systems can carry out.

We extend this definition of set complexity to Poised Realm Systems. With respect to the classical variables of the system, the Set Complexity definition is identical. Using the discussion by W. H. Zurek, Decoherence and the Transition from Quantum to Classical—Revisited, Los Alamos Science No. 27, 2002, we extend set complexity to the quantum degrees of freedom of a Poised Realm system. The mutual information, I, between two quantum systems, S1 and S2 is I(S1, S2)=H(S1)+H(S2)−H(S1,S2). Without loss of generality, the entropy, H, in the above formulation can be taken as the von Neumann entropy as is known in the art.

Using this measure of mutual information I, we compute the mutual information between, without loss of generality, two quantum or Poised Realm degrees of freedom, S1 and S2. Then, for a set of quantum and Poised Realm quantum degrees of freedom in a Poised realm system, we compute the mean mutual information, E, between all pairs of quantum degree of freedom ion the Poised Realm System where E is normalized to a maximum value of 1.0. Quantum Set Complexity is then E×(1−E).

We define the total classical and quantum set complexity as Set Complexity (classical)+Set Complexity (quantum). Classical systems behaving as described by Hamiltonians can be quantized. Not all classical causal systems are so describable by a Hamiltonian, for example, random Boolean nets. However, the x-axis for our kicked quantum rotor, or a kicked quantum oscillator goes from order, with 0 Lyapunov exponent, to a second order (critical) phase transition, to chaos for classical Hamiltonian systems. We believe that the Set Complexity for Hamiltonian systems is maximized for critical classical Hamiltonian systems whether by motion on the y-axis, the x-axis or both. We also believe that total set complexity for a Poised Realm System is maximized for critical classical and critical quantum and Poised Realm quantum and classical behaviors. If so, such Poised systems, classical and quantum can carry out the greatest diversity of organized processes hence are optimal for many practical applications.

More generally, total set complexity is maximized for Poised systems with inputs and outputs somewhere in the Poised Realm, and can be obtained for optimal task performance.

Using the above, we have a design criterion for Poised Realm systems capable of carrying out the maximal information processing, internally diverse dynamical Poised Realm behaviors, and the richest Poised Realm actions on the world or in communities of Poised Realm systems.

It may be that Poised Realm systems can simultaneously maximize a power efficiency per unit fuel, in a generalized sense of fuel as energy, and the diversity of organized behaviors as in the Set Complexity measures above, by operating along the critical line in the Poised Realm. Or there may be a more complex trade off between maximum power efficiency and displacement from equilibrium and maximum set complexity. Both are open to utilization in single Poised Realm Systems or communities of Poised Realm systems.

Possible neurobiological implications: i. We propose that in the vertebrate brain and even in Box Jellyfish, Trans-Turing behavior occurs in molecules, probabably within synapses, perhaps in neurotransmitter receptors. We propose that experience, qualia, are associated with quantum measurement. We propose that entangled degrees of freedom in even anatomically unconnected synapses enables a Unity of Consciousness to solve the binding problem of neurobiology, we propose that the classical behaviors of neurons and sensory tunes tiny time-space variations of transmembrane potentials that constitute the classical Hamiltonians that "tune the drumhead potentials" to cover the external world when measurement occurs, we propose and answer to Descartes: The mind acts acausally on the brain either by decohence or measurement, and can do so repeatedly via recohrence or flowering of quantum behaviors after measurement.

Based on this, one conclusion is that molecules, probably in synapses, comprise evolved Trans-Turing systems. Then we propose that neural networks of real neurons, coupled with modes of mechano-sensory or other inputs, can be molded to be potentially conscious systems capable of practical non-algorithmic problem solving including solving the frame problem and unity of consciousness.

Two approaches to test this are: i. See if neurotransmitter receptors can carry out quantum measurement and test of anesthetics freeze them in a classical state such that they cannot measure, so qualia cannot arise. ii. Select for ease of ether anesthetization in some organism, say Drosophila melanogaster, until little or no ether is needed to produce anesthetization. Compare wild type and mutant proteins for quantum measurement. The wild type should be able to carry out quantum measurement, the mutant proteins should not be able to carry out measurement, or able to do so to a so to a reduced extent perhaps by being frozen classical.

In a preferred embodiment of Trans-Turing systems we make use of incorporation of, without limitation, chlorophyll molecules and their antenna proteins, or other molecules into liposomes, (1-4). Here the chlorophyll and antenna proteins may be embedded in the membrane of the liposome and move in the membrane surface. Alternatively the chlorophyll and antenna proteins may be adfixed to one or more macromolecular assemblies, or by means known in the art to artifical nanostructructes such as, without limitation, nanotube structures, and affixed at known positions and orientations to such nanostructures, for example using streptavidin and biotin.

Work on chloroplasts of diverse light harvesting organisms shows that the average intermolecular distance between chlorophyll-antenna protein complexes ranges from 10 to 20 angstroms. Coherent energy transfer by quantum coherence ranges up to 100 nM, (5). These figures set an initial estimate for the density of chlorophyll antenna complexes that must be incorporated into a liposome of known surface area and volume, typically on the order of 1 micron or less in diameter, to achieve the desired average distances between chlorophyll antenna complexes in the liposome where these complexes float. By means known in the art, rafting of such antenna protein complexes as they aggregate in the liposome membrane can be used, by means known in the art, to achieve higher densities in local subregions of the liposome complex's surface membrane.

An established means known in the art to create liposomes containing a known and tunable mean density of chlorophyll antenna complexes is based on a process in which chloroplast membranes are dissolved in a detergent like sodium deoxycholate along with phospholipid. The detergent is removed by dialysis, the lipid reassembles into lipid vesicles, and the proteins and chlorophyll are incorporated into the bilayers. One can control the ratio of chlorophyll to surface area simply by varying the amount of lipid in the mixture. If one wishes, one can purify the reaction centers ahead of time from a photosynthetic membranes. References to these procedures are incorporated by reference below, (1-4).

In an alternative preferred mode of realization of Trans-Turing systems, noted above, the chlorophyll antenna protein complexes or other molecules are affixed to a nanotube two or three dimensional structure of desired structure and affixed to this using biotin and streptavadin by means known in the art to specific locations on the nanotube structure. The latter structure with affixed chlorophyll and antenna protein complexes are then incorporated into liposomes by dissolving lipids, without limitation, phosopholipids, or any other lipids capable for forming liposomes, in medium containing the nanostructure with affixed chlorophyll and antenna complexes. The latter structures are incorporated into at least some of the newly formed liposomes, creating Trans Turing systems.

Alternatively nanotube or other nanostructures with chlorophyll and antenna proteins, or any other molecules, afixed eg by streptavadin and biotin, may be used to create a Trans-Turing system without encorporation into a liposome or other bounding membrane or structure.

The Trans-Turing systems so constructed can exhibit quantum coherent behavior in electron transfer among antenna protein chloroplasts, including entanglement (5). In addition, one must calculate all possible quantum pathways from antenna chloroplast A to B. Those pathways that pass through the medium, or "bath" in the interior of the liposome can induce deocherence, (5). Thus these systems also live in the quantum-classical poised realm. By means of incident driving quantum or classical input, for example, and without limitation, laser light of tuned wavelength and intensity, recoherence can be induced. Thus these systems can hover in the poised realm. As noted above, by tuning the random versus periodic features of the driving stimulus, the degree and rate of decoherence and recoherence can be controlled.

In addition coupled quantum systems, can exhibit open quantum coherent to decoherence to classicality to recoherence without incident laser light, Ali Nissim, (pc).

As is known in the art, Sholes Included by reference, (5,6), Two-Dimensiopnal photon echo (2DPE) spectropscopy has recently emerged as a practical method for detailed insight into excited state dynamics. Information in 2DPE spectra includes the TIME EVOLUTION of decoherence of coherent superpositions of the absorption bands, which provides a measure of quantum coherence.

It will be clear that 2DPE spectropscopy can be used throughout this patent application for all cases requiring measurement of power law versus exponential decay of decoherence to measure criticality (power law decoherence) or ordered or chaotic position, (exponential decoherence) on the X axis. This is true for measurements of molecules within Trans-Turing systems as they behave, hence we can measure decoherence and recoherence in a Trans turing system or set of coupled Trans-Turing systems. As noted above in this patent application, deviation away from criticality in the Poised Realm yields mix forms of decoherence between power law and exponentials themselves with various decay rates, that can be used to measure position on the X axis of molecules in Trans-Turing systems, in situ, or not, and for drug design as noted above. Thus we can study and follow poised realm behaviors of molecules in time in Trans-Turing Systems, and in cells with respect to drug action, and in neural synapses, which may constitute Trans Turing systems, whose molecules, including neurotransmitters and their receptors may be in the poised realm and play a role in conscious and unconscious mental behaviors along with quantum measurement events in quantum coherent or poised realm systems.

We note that spin echo (7) and neutron spin echo (8) can also be used to measure decoherence.

More, we note that new means are known in the art to achieve controlled entanglement of quantum degrees of freedom, (9), hence entanglement can play a role within and between molecules in one or a plurality of trans-Turing systems, including possibly Trans-Turing behaviors in one or more anatomically connected or unconnected neural synapses. By quantum measurement of one or a plurality of entangled degrees of freedom in Trans Turing Systems, where the degree of Einstein-Podolsky-Rosen NON LOCAL quantum correlations increase with the number of entangled degrees of freedom, highly correlated behaviors of measured, hence now classical, degrees of freedom within one, or a plurality of molecules in a single or set of Trans-Turing Systems, including possible a set of anatomically unconnected but entangled molecules in neural synapses, can arise. These correlated now classical degrees of freedom can have classical causal consequences for the total single or set of coupled trans-turing systems and their quantum, poised realm, and classical behaviors.

The above Trans-Turing systems have classical, quantum coherent, and poised realm inputs, and outputs, including from and to other nearby Trans-Turing systems, thereby forming a "society" of interacting Trans-Turing systems. Without loss of generality, entanglement among the quantum degrees of freedom in one or a plurality of trans-turing systems can occur and can be altered, thereby altering which measured, and now classical degrees of freedom are highly correlated to act jointly as classical aspects of the Trans-Turing system on the Trans-Turing system with respect to its quantum coherent, Poised Realm, and classical degrees of freedom and act as classical aspects of the outputs of the Trans-Turing system.

As noted above, the total behavior of Trans-Turing systems is not definite, via decoherence to classicality FAPP, or quantum measurement of coherent or poised realm behaviors, yet not random due to classical degrees of freedom and their classical Hamiltonian, plus the changing effects of the changing classical behaviors on the quantum coherent and Poised Realm behaviors.

It will be clear to those of ordinary skill in the art, given our specifications above, that we can obtain organic molecules in general, or other molecules, calculate their position of the X order-criticality-chaos axis using the graph theoretical techniques noted above, test for their position on the X axis, and in particular for Poised Realm Critical behavior by testing for power law decoherence at criticality in the Poised Realm, compared to a gradual conversion to exponential decoherence with different exponential decay rates as molecules are located on the X axis further toward order or chaos from criticality. Thus, we can assemble, in general, molecules of any desired distribution on the X axis, from all critical, to any other distribution, for incorporation into liposomes to create Trans-Turing systems.

Alternatively we can use such molecules in the X axis on nanofabricated Trans-Turing systems. Or we can use macroscopic Trans-Turing systems.

In a preferred embodiment of this invention, the molecules incorporated into the liposome to create trans-turing systems will be closely clustered around the critical location in the Poised Realm. Here we expect a maximum of controllable behavior as the quantum chaotic domains described above increase in size up to merging, or not quite merging, into the giant component described above at Poised Realm criticality. We expect the most complex Poised Realm behavior here, at the conductor-insulator transition critical transition described above. More we expect the most complex computational behavior among critical coupled classical degrees of freedom, and we expect optimal energy transfer from quantum modes to classical modes of behavior at criticality based, as noted elsewhere on Fermi's golden rule of preferential measurement of those amplitudes with the highest modulus, or preferential decoherence of amplitudes with large moduli. The energy will be released into the now classical degree(s) of freedom.

Using our graph theoretical calculations, we can synthesize, or screen for by use of combinatorial chemistry means known in the art, molecules of any sort, eg without limitation, binding a known ligand, or catalyzing a known reaction, or binding to a stable analogue of a transition state, at known positions of the X axis for incorporation into Trans-Turing systems., for the behavior of molecules in Trans-Turing systems alone or coupled, or drug candidates. As we noted above, the failure of classical physics—"lock-key" ideas for combinatorial chemistry, where Kauffman has the founding international patents filed in 1985, to yield functional drugs, compared to the success in Japanese pharmaceutical companies which continue to use medicinal chemistry techniques, suggests that the medicinal chemistry techniques may well be, inadvertantly, probing in vivo Poised Realm behaviors, beyond classical lock-key concepts, in drug discovery. This bears on our uses of the Poised Realm for drug discovery as described above.

Link to Consciousness in the Human Brain, and coupled Trans-Turing Systems.

The human brain has about 10 to the 11 neurons, each with an average of 600 synapses. Each axon ends on one dendrite. Many dendrites, each with many synapses, feed into one downstream neuronal cell. With the arrival of an action potential at a synapse, neurotransmitter molecules are released, travel across the synaptic cleft and bind to neurotransmitter receptors. Often this results, via a complex of molecules including the receptor, in opening or closing a channel on the post synaptic dendrite, leading to tiny time/space alterations in the local transmembrane potential. These alterations travel to the axon hillock of the neural cell and are summed. If the transmembrane potential increases to less than about −20 mV, an action potential is likely to be initiated and travel down the axon to impinge on one or more downstream synapses.

Francis Crick, in the Astonishing Hypothesis, (10), points out that a vast amount of information is thrown away concerning the behaviors of vastly many molecules in synapses and tiny time space alterations in dendritic transmembrane potentials to achieve either firing or not firing of a classical physics action potential.

We believe it is a sensible hypothesis to "stand the brain on its head", and ask whether the synapses are the "business end" of the brain, whose behavior is partially driven by the sensory inputs and classical physics neural network among the 10 to the 11th neurons and 600 times as many synapses. If so, the synapse itself may be a Trans-Turing system operating in the Poised Realm, where decoherence, recoherence, and quantum measurements may occur.

We hypothesize that conscious experience is associated with quantum measurement in coherent or poised realm quantum systems. The resulting classical degrees of freedom, post measurement, allow the conscious mind via these classical variables to have classical physical consequences for the total mind-brain system, answering Descartes about how mind acts on matter. Measurement is NOT causal, so mind does not act causally on matter. In addition, decoherence to classicality FAPP may allow mind to have acausal consequences for brain.

The hypothesis that conscious experience, qualia, are associated with quantum measurement is testable in two ways at least: i. anesthetics bind to neurotransmitter receptors in hydrophobic pockets. If the "freeze" neurotransmitters into classical or classical FAPP behavior such that the neurotransmitters receptors cannot undergo measurement events, while in the absence of anesthetics neurotransmitter receptors do undergo measurement events, that is evidence that conscious experience, ie "qualia", IS associated with quantum measurement. In addition, fruit flies, Drosophila melaogaster, can be ether anesthetized. Selection of anesthetization with decreasing ether doses can yield mutant proteins that, with anesthesia for little or no ether, may reveal by standard genetics the protein and other molecules associated with consciousness. Then the mutant proteins or other molecules can be tested for "freezing" such that they cannot undergo measurement, while the unselected normal, or wild type versions of those proteins can undergo quantum measurement. These experiments can help identify the possibly synaptic molecules whose quantum and Poised Realm and classical behavior is related to consciousness. On this view, decoherence to classicality FAPP may be associated with unconscious actions of mind on brain.

If these results are obtained, we can construct living neural networks of controlled network "architecture" and dendritic synaptic interconnections, graft these to sensor inputs, say, without limitation, from the Box jelly fish eye and its downstream neurons as inputs to the above neural net, and effector neurons acting on artificial output devices, limbs, actuators and so forth. From these neural systems, or using non-neural general Trans-Turing systems alone or coupled, including coupled by entanglement, we can create devices that classify their worlds, solve the frame problem, and act on their worlds, see just below "Evolving Trans-Turing Systems."

More, by entanglement of diverse unconnected or connected quantum degrees of freedom in diverse synapses, or trans-turing systems, and quantum measurement of those entangled degrees of freedom, highly correlated, due to Einstein Podolski Rosen non local "EPR" quantum effects violating Bell's inequalities will arise, and the now highly correlated and also now classical degrees of freedom can be used to act causally on the classical world, as well as to modify the ongoing behavior of the single or coupled Trans-Turing systems. Finally, local alterations can alter which quantum degrees of freedom are entangled, thereby altering: i. which now classical degrees of freedom are correlated upon their quantum measurement; ii. if qualia are associated with quantum measurement, entangled quantum degrees of freedom may yield a unity of consciousness, that is, a solution to the qualia binding problem. Shifting patterns of entanglement in effect, shift the "focus of attention" of the coupled Trans-Turing systems.

A further feature of note in considering either neural systems with synapses, or more general networks of Trans Turing systems arises as follows. Consider a classical physics volume with a classical physics gas in it. Does measuring the position and momentum of one classical particle give any insight into the SHAPE of the volume, or "box"? No. By contrast, a quantum wave behavior in a classical potential well that serves as its BOUNDARY CONDITIONS, "feels" or "knows" its boundary conditions which show up, for example, and without limitation, in the spectrum of its energy levels. Thus the wave property of a quantum system knows the SHAPE of its boundary condition potential well.

Consider by analogy, a room filled with music. Now consider breaking the room into tiny 3 dimensional volumes and measuring pressure in each as a function of time, then analyzing these via a digital "propositional" computer. Compare this to an analogue in which 1000 differently shaped drum heads are placed around the music filled room. The spectral (eigenfunction) patterns of vibration of the diverse drum heads, each reflecting the boundary conditions arising due to the shape of its drum head, "know" in a non-propositional and analogue way the music in the room. Telephones used to work in this way.

Similarly, consider the tens of billions of synapses in the brain, where sensory inputs from the world, and classical physics firing of action potentials, TUNE the tiny time/space synaptic and local dendritic transmembrane potentials that serve as part of the potential well, or boundary condition on possible coherent or Poised Realm quantum wave behaviors among, say, neurotransmitter receptor molecules. Then the energy levels and other behaviors of those molecules, or any other relevant quantum or Poised Realm molecules or components, "Know", the shapes of their potential well boundary conditions. But this means that proper tuning of those boundary conditions allow the Poised Realm, hence probably Trans-Turing behaviors, in the synapsic region to know their external world. By entanglement of quantum degrees of freedom, coherent or Poised Realm, in properly tuned sets of potential wells, and quantum measurement of many entangled quantum degrees of freedom, tuned and highly correlated qualia are achieved, so a unity of consciousness is achieved, solving the neural binding problem. Thus, neural devices made as above may achieve this.

More generally, the same holds for a plurality of Trans-Turing systems whose potential wells are constituted in part by classical degrees of freedom, and which can be tuned, like the drum heads, to reflect in a coordinated way the "world" around the set of Trans-Turing systems. They collectively "Know" their embedding world, and do so in a non-propositional way. In turn, the lack of a propositional form, allows such evolving Trans Turing systems, see just below, to solve the Frame problem of computer science via Darwinian preadaptations and other means.

Evolving Trans-Turing Systems for Desired Behaviors.

Trans Turing systems can be studied either by simulation or by construction of embodied trans-turing systems. In either case, to "program" a trans-turing system to achieve a desired behavior, a preferred means is to use some analogue of the Holland Genetic Algorithm, or more generally an adaptive strategy using generations of populations of variant Trans-Turing systems, choosing the "best" subset of the members of each generation, keeping these unmodified and slightly modified to create a next generation of Trans-Turing systems, and selecting the fittest by some "figure of merit" or selection criterion.

In general, any combination of time constant or time varying classical, poised realm, and quantum coherent inputs and outputs can be used to define a figure of merit. As a non-limiting example, generalized "pattern recognition" on a set of quantum coherent, eg laser, poised realm, eg from another Trans-turing system, and classical inputs can be used as inputs, and output behavior that classifies these into alternative time constant or time varying patterns of quantum coherent, poised realm, and classical outputs can be the figure of merit that is the basis of selection on successive generations.

In general, any such mapping of inputs to desired outputs, classed in any way by the Trans-Turing system, creates a "fitness landscape" over the space of parameters used to vary the structure and coupling among the variables in the Trans-Turing system or set of interacting Trans-Turing Systems. It is well known in the art that the statistical features of this fitness landscape for any single figure of merit may be simple and single peaked, or "rugged" and multipeaked, and even "random" with many local peaks. It is known in the art that recombination works as an adaptive strategy on landscapes which are not too rugged (Kauffman, Origins of Order, Oxford Univ Press 1993 incorporated here by reference, (11)).

More generally, if there are multiple figures of merit and their relative importance is not definable, Global Pareto optimality is, as known in the art, the sensible solution concept.

It will be clear to those of ordinary skill in the art, that TransTuring system may be embodied in self reproducing "protocells" able to reproduce, and yield heritable variations, thus undergo adaptive evolution given a figure of merit, and undergo Darwinian preadaptations, also called Exaptations, (see Kauffman Investigations, Oxford University Press 2000, and Reinventing the Sacred, Basic Books, 2008 both incorporated here by reference, (12,13). Critically, exaptations allow NEW functions to emerge. As a concrete example, some fish have swim bladders, sacs filled with air and water, whose ratio determines neutral buoyancy in the water column. These evolved by preadaptations from the lungs of lung fish. Here a new function, neutral buoyancy, arose in the biosphere. This new function SOLVES the "FRAME PROBLEM" in computer science. The frame problem consists in the following: picture a robot with a standard digital computer on board. Many features of the robot and, say room it is in, are described FINITELY and given "affordances". Here, for example the arm of the robot has a finite number of described features, each with FINITE LIST of propositionally defined affordances: Is a, Does A, Needs A, . . . . The frame problem is this: Given a task, we are NOT guaranteed that the robot can deduce from the finite list propositionally defined affordances the solution to the task.

But preadaptations of Trans-Turing systems that are evolving or co-evolving, as in the case of the evolution by preadaptation swim bladders which confer neutral buoyancy in the water column by the ratio of air and water in the swim bladder, evolved from the lungs of lung fish, yield the novel function of the swim bladder: neutral buoyancy. This new function, in general, would never be represented a finite list of affordances propositionally concerning the lungs of lung fish. Preadaptations arise in evolving embodied systems that are Kantian wholes in which the whole where the part exist for and by means of the whole, and the whole exists for and by means of the parts. As a non-limiting example, collectively autocatalytic sets of polymers such as peptides, (14), are such Kantian wholes. Gonen Ashkenazi, (15), at Ben Gurion University in Beer Sheeba Israel has a nine peptide collectively autocatalytic set. Here no peptide catalyzes its own formation, but the formation of another peptide from smaller peptides that are "food" fed to the system, and are fragments of the "other" peptide in question. It is essential that in the collectively autocatalytic set, no peptide catalyzes its own formation. Calling catalysis of a specific reaction a catalytic "task", the nine peptide system achieves CATALYTIC TASK "CLO- SURE (11,14). All the reactions that must be catalyzed ARE catalyzed by some peptide in the collectively autocatalytic whole.

A collectively autocatalytic peptide system is an example of a Kantian whole. The parts exist in the universe by means of the whole, and the whole exists in the universe by means of the parts (16).

Now consider an evolving cell. It too achieves a closure in a set of tasks. But these are far wider than catalysis, and include making membranes, vectoring proteins to specific organelles in the cell, doing work cycles, and reproducing by mitosis.

The next essential point to realize about the evolution of Kantian wholes is that each part has consequences. For a Trans-Turing system these are quantum coherent, poised realm, and classical. But there is no orderable or finite list of the consequences of any part alone or with indefinitely many other parts. Further, for each consequence there is no orderable or finite list of potential USES of that consequence. Yet, for the ongoing evolution of the Kantian whole, by heritable variations and some form of selection, all that is needed is that at least ONE, or a plurality of consequences of one or a plurality of parts, FIND SOME USE among their consequences that enhances the fitness of the Kantian Trans-Turing whole with respect to any figure of merit. This allows, via quantum and/or poised realm/and or classical consequences, new functionalities to emerge that are not logically entailed by a finite list of propositional statements of affordances of parts of, eg a robot or standard computer. The embodied Trans-Turing system solves the frame problem, never solved in computer science.

In one preferred embodiment of this invention, Trans-Turing systems are part of evolving and coevolving protocells with an autocatalytic set of polymers, RNA or proteins or any other polymers, or merely an autocatalytic set of molecules, housed in a reproducing liposome. Here liposome reproduction has been achieved experimentally, (17). Collectively autocatalytic sets have been achieved experimentally. Recent work shows that such sets can undergo open ended evolution, (18), and if contained in a liposome that undergoes growth and budding, the autocatalytic set can typically synchronize its own reproduction with that of the liposome. (19). In short, Trans-Turing systems capable of evolving and co-evolving in protocells are now feasible and can evolve to adapt to a known figure of merit by adaptations or preadaptations, where the both solve the computer science Frame Problem.

Craig Ventner has recently created an "artificial cell" with DNA, RNA and encoded proteins, able to reproduce and create desired proteins, (20). It will be clear to those of ordinary skill in the art that such systems can be used to create populations of evolving Trans-turing systems, using encoded proteins and a metabolism of smaller organic molecules capable of Poised Realm and Trans-Turing behavior. The positions of these molecules on the X axis can be calculated using our graph theoretical procedures, and experimentally verified using power law versus exponential deocherence rates.

More, the artifical cell can embody a genetic regulatory net of transcription factors which activate and inhibit one another. This network, (see Kauffman, 1993, Origins of Order), can be dynamically ordered, critical or chaotic. The most controllable behavior occurs for critical networks. There is evidence that real cells are critical, (Nykter et al, (21). This classical critical behavior can be married to Trans-Turing behavior which is also critical, to achieve Trans-Turing systems that optimize the diversity of organized behaviors of the total system. Here the degree of organization of a causal process can be measured by its power efficiency per unit fuel, and the choice of which causal process to consider among a set of interwoven causal processes of each part of the system can be chosen to maximize Set Complexity, defined elsewhere in this patent application. This can be generalized to measure set complexity of the total quantum and classical aspects of the system, as specified in this patent application elsewhere.

In another embodiment of Trans-Turing systems, these can be constructed using nano-tube structures of arbitrary sizes and two or three dimensional structure, with chlorophyll and antenna proteins, or any other atoms of molecules, affixed at known or variable positions on the nanotube structure, and capable of quantum coherent, open quantum Poised Realm, and classical behaviors, to create one or any population of Trans-Turing systems. By fabrication or any other means, know or in the future known, a population of similar or increasingly diverse Trans Turing systems can be constructed, and in parallel with the discussion above, can be selected by evolution, or co-evolution of interacting identical or diverse Trans Turing systems, to increasing fitness with respect to single figures of merit, or, using global pareto optimality, for optimal solutions to a set of figures of merit where the relative importance of the plurality of success criteria are not specifiable.

REFERENCES

All of which are incorporated herein by reference in their entirety.

1. Frankenberg, N., Hager-Braun, C., Teiler, U. Fuhrmann, M., Rogl, H., Schneebauer, N., Nelson, N., and Hauska, G. (2008). P840-Reaction Centers from Chlorobium tepidum-Quinone Analysis and Functional Reconstitution into Lipid Vesicles. Photochemistry and Photobiology, 64:(1), 1-14.
2. Jones, M. R., McEwan, A. G., and jackson, J. B. (2010). The role of c-type cytochromes in the photosynthetic electron transport pathway of Rhodobacter capsulatus. Biochimica et Biophysica Acta—Bioenergetics, Vol 1019, issue 1, 59-66.
3. Gabellini, N. Gao, Z., Oesterhelt, D., Venturolli, G., and Melandri, B. A. (1989).
   Reconsititution of cyclic electron transport nd photophosphorylation by incorporation of the reaction center, bc1 complex and ATP synthase from Rhodobacter capsulatus into ubiquinone-10/phospholipid vesicles. Biochimica et Biophsica Acta—Bioenergetics, Vol 974, issue 2: 202-210.
4. Varga, A. R., and Staehelin, L. A. (1985). Pigment-Protein Complexes from Rhodopsuedomas palustris: Isolation, Characterization, and Reconstitution into Liposomes. Journal of Bactriology, vol 161 no 3: P 921-927.
5. Scholes, G. D., (2010). Quantum-Coherent Energy Transfer: Did Nature Think Of It First? The Journal of Physical Chemistry Letters, 1: 2-8.
6. Pascher, T., Polyutov, S. Yartsev, A., Pullerits, T., Lenngren, N. (2011), Photon echo spectroscopy, Wikipedia.
7. Hahn, E. L. (1950). "Spin Echoes". Phys. Rev. 80: 580-594.
8. Mezel, F. (ed) (1980) Neutron Spin Echo, Lecture Notes in Physics, vol 128, Springer
9. Science News Nov. 20, 2010. Inducing Entanglement.
10. Francis Crick, The Astonishing Hypothesis: The Scientific Search For the Soul, TOUCHSTONE, Simon an Schuster, N.Y. 1994.
11. Kauffman, S. A. Origins of Order, Oxford University Press, N.Y. (1993).
12. Kauffman, S. A. Investigations, Oxford University Press, N.Y. (2000).

13. Kauffman, S. A. Reinventing the Sacred. Basic Books, N.Y. (2008).
14. Kauffman S. A. (1986). Autocatalytic Sets of Proteins. J. Theor. Bio. 119: 1-24.
15. N. Wagner and Ashkenasy, G. (2009). Symmetry and order in systems chemistry. The Journal of Chemical Physics, 130: 164907-164911.
16. Kauffman, S. A. Origins of Order, Oxford University Press. N.Y. (1993).
17. P. L Luisi, Stano, P., Rasi, S., and Mavelli, F. (2004). A possible route to prebiotic vesicle reproduction, Artifical Life, 10: 297-308.
18. C. Fernando, Vasas, V., Santos, M., Kauffman, S., and Szathmary, E. (2011). Spontaneous Formation and Evolution of Autocatalytic Sets within Compartments. Submitted.
19. A. Filsetti, Serra, R., Carletti, T., Villiani, M., and Poli., I. (2010). Non-linear protocell models: synchronization and chaos. Eur. J. Phys. J. B 77: 249-256.
20. R. L. Hotz. (2010). Scientists Create Synthetic Organism. Wall Street Journal May 21.
21. Nykter, M., Price, N. D., Aldana, M., Ramsey, S. A., Kauffman, S. A., Hood, L., Yli-Harja, O. and Shmulevich, I. (2008). Gene Expression Dynamics in the Macrophage Exhibit Criticality. *Proc Natl Acad Sci USA* 105(6).: 1897-1900.

Unless otherwise indicated, all references disclosed herein are incorporated herein by reference in their entirety.

What is claimed is:

1. A quantum reservoir computer, comprising:
a plurality of nodes comprising chromophores, each node comprising at least one quantum degree of freedom that is coupled to at least one quantum degree of freedom in each other node, wherein the quantum degrees of freedom comprise electronic excitation states;
at least one input signal generator comprising a laser, wherein the input signal generator is configured to produce at least one time-varying input signal that couples to said quantum degree of freedom, the time-varying input signal selected from a time-varying change in laser pulse frequency, a time-varying change in laser light frequency, and a time-varying change in laser light intensity; and
a detector selected from a photodetector and a spectrometer, the detector configured to receive a plurality of time-varying output signals that couple to said quantum degree of freedom, the time-varying output signals selected from a time-varying change in light frequency and a time-varying change in light intensity.

2. The computer of claim 1, further comprising an algorithmic computer coupled to the detector and configured produce a computer output based on the time-varying output signals.

3. The computer of claim 2, wherein the computer output is based on a weighted combination of the plurality of time-varying output signals.

4. The computer of claim 3, wherein the weighted combination is a linear combination.

5. The computer of claim 1, wherein the chromophore comprises a photosynthetic unit.

6. The computer of claim 5, wherein the photosynthetic unit comprises chlorophyll.

7. The computer of claim 1, wherein the at least one input signal generator comprises a laser.

8. The computer of claim 1, wherein the detector comprises a photodetector.

9. The computer of claim 1, wherein the detector comprises a plurality of detecting regions distributed in space.

10. The computer of claim 9, wherein the detector comprises an array of sub-detectors.

* * * * *